(12) United States Patent
Nett et al.

(10) Patent No.: US 7,479,389 B2
(45) Date of Patent: Jan. 20, 2009

(54) ARG1, ARG2, ARG3, HIS1, HIS2, HIS5, HIS6 GENES AND METHODS FOR STABLE GENETIC INTEGRATION

(75) Inventors: Juergen Nett, Grantham, NH (US); Tillman Gerngross, Hanover, NH (US)

(73) Assignee: GlycoFi, Inc., Lebanon, NH (US)

( * ) Notice: Subject to any disclaimer, the term of this patent is extended or adjusted under 35 U.S.C. 154(b) by 433 days.

(21) Appl. No.: 11/071,690

(22) Filed: Mar. 2, 2005

(65) Prior Publication Data

US 2007/0072262 A1 Mar. 29, 2007

Related U.S. Application Data

(60) Provisional application No. 60/549,662, filed on Mar. 2, 2004.

(51) Int. Cl.
*C12N 15/74* (2006.01)
*C12N 15/00* (2006.01)
*C12P 21/00* (2006.01)
*C12N 1/19* (2006.01)
*C07K 14/00* (2006.01)
*C07H 21/00* (2006.01)

(52) U.S. Cl. .......... 435/471; 435/440; 435/69.1; 435/477; 435/483; 435/320.1; 435/254.23; 435/481; 530/350; 536/23.1; 536/23.2

(58) Field of Classification Search ........... 435/69.1, 435/320.1, 254.23, 254.2, 440, 471; 530/350; 536/23.1, 23.2
See application file for complete search history.

(56) References Cited

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Kimura et al., Mol. Gen. Genet., vol. 242 (1994), pp. 121-129, "Cloning of the balsticidin S deaminase gene (BSD) from *Aspergillus terreus* and its use as a selectable marker . . . ".
Waterham et al., Gene, vol. 186 (1997), pp. 37-44, "Isolation of the *Pichia pastoris* glyceraldehyde-3-phosphate dehydrogenase gene and regulation and use of its promoter".
Tuttle et al., J. of Cell Science, vol. 108 (1995), pp. 25-35, "Divergent modes of autophagy in the methylotrophic yeast *Pichia pastoris*".
Sakai et al., J. of Cell Biol., vol. 141 (1998), pp. 625-636, "Peroxisome degradation by microautophagy in *Pichia pastoris*: Identification of specific steps and morphological intermediates".
Rossanese et al., J. of Cell Biol., vol. 145 (1999), pp. 69-81, "Golgi structure correlates with transitional endoplasmic reticulum organization in *Pichia pastoris* and *Saccharomyces cerevisiae*".
Orr-Weaver et al., PNAS USA, vol. 78 (1981), pp. 6354-6358, "Yeast transformation: A model system for the study of recombination".
Nett et al., Yeast, vol. 20 (2003), pp. 1279-1290, "Cloning and disruption of the PpURA5 gene and construction of a set of integration vectors for the stable genetic modification of *Pichia pastoris*".
Szczebara et al., Nature Biotech., vol. 21 (2003), pp. 143-149, "Total biosynthesis of hydrocortisone from a simple carbon source in yeast".
Lin Cereghino et al., Curr. Opin. in Biotech., vol. 13 (2002), pp. 329-332, "Production of recombinant proteins in fermenter cultures of the yeast *Pichia pastoris*".
Lin Cereghino et al., FEMS Microbiol. Rev., vol. 24 (2000), pp. 45-66, "Heterologous protein expression in the methyloptrophic yeast *Pichia pastoris*".
Lin Cereghino et al., Gene, vol. 263 (2001), pp. 159-169, "New selectable marker/auxotrophic host strain combinations for molecular genetic manipulation of *Pichia pastoris*".
Hamilton et al., Science, vol. 301 (2003), pp. 1244-1246, "Production of complex human glycoproteins in yeast".
Gould et al., Yeast, vol. 8 (1992), pp. 613-628, "Development of yeast *Pichia pastoris* as a model organism for a genetic and molecular analysis of peroxisome assembly".
Alani et al., Genetics, vol. 116 (1987), pp. 541-545, "A method for gene disruption that allows repeated use of URA3 selection in the construction of multiply disrupted yeast strains".
Chiba et al., J. of Biol. Chem., vol. 273 (1998), pp. 26298-26304, "Production of human compatible high mannose-type (Man5GlcNAc2) sugar chains in *Saccharomyces cerevisiae*".
Choi et al., PNAS, vol. 100 (2003), pp. 5022-5027, "Use of combinatorial genetic libraries to humanize N-linked glycosylation in the yeast *Pichia pastoris*".
Cregg et al., Mol. & Cell. Biol., vol. 5 (1985), pp. 3376-3385, "*Pichia pastoris* as a host system for transformations".
Goldstein et al., Yeast, vol. 15 (1999), pp. 1541-1553, "Three new dominant drug resistance cassettes for gene disruption in *Saccharomyces cerevisiae*".
Higgins et al., Methods in Molecular Biol., vol. 103 (1998), pp. 41-53, "Small vectors for expression based on dominant drug resistance with direct multicopy selection".
Higgins et al., Methods in Molecular Biol., vol. 103 (1998), pp. 1-15, Introduction to *Pichia pastoris*.

* cited by examiner

*Primary Examiner*—Delia M Ramirez
(74) *Attorney, Agent, or Firm*—John David Reilly; Catherine D. Fitch; William Krovatin

(57) ABSTRACT

Novel genes encoding *P. pastoris* ARG1, ARG2, ARG3, HIS1, HIS2, HIS5 and HIS6 are disclosed. A method for inactivating alternately at least two biosynthetic pathways in a methylotrophic yeast is provided. A method for producing and selecting yeast strains characterized as being capable of genetic integration of heterologous sequences into the host genome using the genes involved in the biosynthetic pathways is also disclosed.

5 Claims, 16 Drawing Sheets

FIG 1A

```
   1 CAGTTGAGCCAGACCGCGCTAAACGCATACCAATTGCCAAATCAGGCAATTGTGAGACAGTGGTAAAAAAGATGCCTGCAAAGTTAGATTCACACAGTA
 100 AGAGAGATCCTACTCATAAATGAGGCGCTTATTTAGTAGCTAGTGATAGCCACTGCGGTTCTGCTTTATGCTATTTGTTGTATGCCTTACTATCTTTGT
 199 TTGGCTCCTTTTTCTTGACGTTTTCCGTTGGAGGGACTCCCTATTCTGAGTCATGAGCCGCACAGATTATCGCCCAAAATTGACAAAATCTTCTGGCGA
 298 AAAAAGTATAAAAGGAGAAAAAAGCTCACCCTTTTCCAGCGTAGAAAGTATATATCAGTCATTGAAGACTATTATTTAAATAACACAATGTCTAAAGGA
                                                                                                    1▶ M  S  K  G
 397 AAAGTTTGTTTGGCCTACTCCGGTGGTTTGGATACCTCCATCATCCTAGCTTGGTTGTTGGAGCAGGGATACGAAGTCGTTGCCTTTTTAGCCAACATT
   5▶ K  V  C  L  A  Y  S  G  G  L  D  T  S  I  I  L  A  W  L  L  E  Q  G  Y  E  V  V  A  F  L  A  N  I
 496 GGTCAAGAGGAAGACTTTGAGGCTGCTAGAGAGAAAGCTCTGAAGATCGGTGCTACCAAGTTTATCGTCAGTGACGTTAGGAAGGAATTTGTTGAGGAA
  38▶ G  Q  E  E  D  F  E  A  A  R  E  K  A  L  K  I  G  A  T  K  F  I  V  S  D  V  R  K  E  F  V  E  E
 595 GTTTTGTTCCCAGCAGTCCAAGTTAACGCTATCTACGAGAACGTCTACTTACTGGGTACCTCTTTGGCCAGACCAGTCATTGCCAAGGCCCAAATAGAG
  71▶ V  L  F  P  A  V  Q  V  N  A  I  Y  E  N  V  Y  L  L  G  T  S  L  A  R  P  V  I  A  K  A  Q  I  E
 694 GTTGCTGAACAAGAAGGTTGTTTTGCTGTTGCCCACGGTTGTACCGGAAAGGGTAACGATCAGGTTAGATTTGAGCTTTCCTTTTATGCTCTGAAGCCT
 104▶ V  A  E  Q  E  G  C  F  A  V  A  H  G  C  T  G  K  G  N  D  Q  V  R  F  E  L  S  F  Y  A  L  K  P
 793 GACGTTGTCTGTATCGCCCCATGGAGAGACCCAGAATTCTTCGAAAGATTCGCTGGTAGAAATGACTTGCTGAATTACGCTGCTGAGAAGGATATTCCA
 137▶ D  V  V  C  I  A  P  W  R  D  P  E  F  F  E  R  F  A  G  R  N  D  L  L  N  Y  A  A  E  K  D  I  P
 892 GTTGCTCAGACTAAAGCCAAGCCATGGTCTACTGATGAGAACATGGCTCACATCTCCTTCGAGGCTGGTATTCTAGAAGATCCAAACACTACTCCTCCA
 170▶ V  A  Q  T  K  A  K  P  W  S  T  D  E  N  M  A  H  I  S  F  E  A  G  I  L  E  D  P  N  T  T  P  P
 991 AAGGACATGTGGAAGCTCACTGTTGACCCAGAAGATGCACCAGACAAGCCAGAGTTCTTTGACGTCCACTTTGAGAAGGGTAAGCCAGTTAAATTAGTT
 203▶ K  D  M  W  K  L  T  V  D  P  E  D  A  P  D  K  P  E  F  F  D  V  H  F  E  K  G  K  P  V  K  L  V
1090 CTCGAGAACAAAACTGAGGTCACCGATCCGGTTGAGATCTTTTTGACTGCTAACGCCATTGCTAGAAGAAACGGTGTTGGTAGAATTGACATTGTCGAG
 236▶ L  E  N  K  T  E  V  T  D  P  V  E  I  F  L  T  A  N  A  I  A  R  R  N  G  V  G  R  I  D  I  V  E
1189 AACAGATTCATCGGAATCAAGTCCAGAGGTTGTTATGAAACTCCAGGTTTGACTCTACTGAGAACCACTCACATCGACTTGGAAGGTCTTACCGTTGAC
 269▶ N  R  F  I  G  I  K  S  R  G  C  Y  E  T  P  G  L  T  L  L  R  T  T  H  I  D  L  E  G  L  T  V  D
1288 CGTGAAGTTAGATCGATCAGAGACACTTTTGTTACCCCAACCTACTCTAAGTTGTTATACAACGGGTTGTACTTTACCCCAGAAGGTGAGTACGTCAGA
 302▶ R  E  V  R  S  I  R  D  T  F  V  T  P  T  Y  S  K  L  L  Y  N  G  L  Y  F  T  P  E  G  E  Y  V  R
1387 ACTATGATTCAGCCTTCTCAAAACACCGTCAACGGTGTTGTTAGAGCCAAGGCCTACAAAGGTAATGTGTATAACCTAGGAAGATACTCTGAAACCGAG
 335▶ T  M  I  Q  P  S  Q  N  T  V  N  G  V  V  R  A  K  A  Y  K  G  N  V  Y  N  L  G  R  Y  S  E  T  E
1486 AAATTGTACGATGCTACCGAATCTTCCATGGATGAGTTGACCGGATTCCACCCTCAAGAAGCTGGAGGATTTATCACAACACAAGCCATCAGAATCAAG
 368▶ K  L  Y  D  A  T  E  S  S  M  D  E  L  T  G  F  H  P  Q  E  A  G  G  F  I  T  T  Q  A  I  R  I  K
1585 AAGTACGGAGAAAGTGTCAGAGAGAAGGGAAAGTTTTTGGGACTTTAACTCAAGTAAAAGGATAGTTGTACAATTATATATACGAAGAATAAATCATTA
 401▶ K  Y  G  E  S  V  R  E  K  G  K  F  L  G  L
1684 CAAAAAGTATTCGTTTCTTTGATTCTTAACAGGATTCATTTTCTGGGTGTCATCAGGTACAGCGCTGAATATCTTGAAGTTAACATCGAGCTCATCATC
1783 GACGTTCATCACACTAGCCACGTTTCCGCAACGGTAGCAATAATTAGGAGCGGACCACACAGTGACGACATC
```

FIG 1B

```
1   M S K G K V C L A Y S G G L D T S I I L A W L L E Q G Y E V V A F L A N I G Q E   PpARG1
1   M S K G K V C L A Y S G G L D T S V I L A W L L D Q G Y E V V A F M A N V G Q E   ScARG1

41  E D F E A A R E K A L K I G A T K F I V S D V R K E F V E E V L F P A V Q V N A   PpARG1
41  E D F D A A K E K A L K I G A C K F V C V D C R E D F V K D I L F P A V Q V N A   ScARG1

81  I Y E N V Y L L G T S L A R P V I A K A Q I E V A E Q E G C F A V A H G C T G K   PpARG1
81  V Y E D V Y L L G T S L A R P V I A K A Q I D V A K Q E G C F A V S H G C T G K   ScARG1

121 G N D Q V R F E L S F Y A L K P D V V C I A P W R D P E F F E R F A G R N D L L   PpARG1
121 G N D Q I R F E L S F Y A L K P D V K C I T P W R M P E F F E R F A G R K D L L   ScARG1

161 N Y A A E K D I P V A Q T K A K P W S T D E N M A H I S F E A G I L E D P N T T   PpARG1
161 D Y A A Q K G I P V A Q T K A K P W S T D E N Q A H I S Y E A G I L E D P D T T   ScARG1

201 P P K D M W K L T V D P E D A P D K P E F F D V H F E K G K P V K L V L E N K T   PpARG1
201 P P K D M W K L I V D P M D A P D Q P Q D L T I D F E R G L P V K L T Y T D N K   ScARG1

241 E - - - - - V T D P V E I F L T A N A I A R R N G V G R I D I V E N R F I G I K   PpARG1
241 T S K E V S V T K P L D V F L A A S N L A R A N G V G R I D I V E D R Y I N L K   ScARG1

276 S R G C Y E T P G L T L L R T T H I D L E G L T V D R E V R S I R D T F V T P T   PpARG1
281 S R G C Y E Q A P L T V L R K A H V D L E G L T L D K E V R Q L R D S F V T P N   ScARG1

316 Y S K L L Y N G L Y F T P E G E Y V R T M I Q P S Q N T V N G V V R A K A Y K G   PpARG1
321 Y S R L I Y N G F L L H P E C E Y I R S M I Q P S Q N S V N G T V R V R L Y K G   ScARG1

356 N V Y N L G R Y S E T E K L Y D A T E S S M D E L T G F H P Q E A G G F I T T Q   PpARG1
361 N V I I L G R S T K T E K L Y D P T E S S M D E L T G F L P T D T T G F I A I Q   ScARG1

396 A I R I K K Y G E S V R E K G K F L G L   PpARG1
401 A I R I K K Y G E S K K T K G E E L T L   ScARG1
```

FIG 2A

```
   1 GTGAGCGATGAGGAGGGCCCACTGAGTTATGATATATGATATATATTTAGAAACGGTTCGCACAGAATAGTGGCCAGCAAAACATCATTTTTCGGTGGA
 100 GTTTTGACTGGTTTATGAAGCCCTTAATTGTGAAAAGGTGTAAGAAAGTGTGCATCTCGAATTTACTCCATAGTCCATTAGCCTCCACCTTCCCTTTAA
 199 CCGTGTATTTGTGAATGGTGTTCACTATGTTTCCTAGGGCATTACCATCCTGTCGCCGTCAGTCAGGCCGTATGTTCATAAGCGTAAGTAATTGAAACC
 298 TTTTGACACCGCAGCGATCTCCCACTAACCAGTAGTCCATGTTGAGTATCAAAGATTTCACCTCAAATCTCACAAGACATGCTAGAAACACCGAGGAGA
                                                         1▸  M   L   S   I   K   D   F   T   S   N   L   T   R   H   A   R   N   T   E   E
 397 AAAGGAACATGGTTCTAACTATCCTCAACTCCACTGCTACCAAGAGAGAAGTTCGAAACTACTTGAAGAAGTATCCTCTATTAAAGGATGTGGATATCT
  21▸ K   R   N   M   V   L   T   I   L   N   S   T   A   T   K   R   E   V   R   N   Y   L   K   K   Y   P   L   L   K   D   V   D   I
 496 ACAGTAAGGGCCAAATGGATCGGAGCTCCGTTAGCAAACGTAACAAGTACTCCAGCATGATTGACAATCTCATGTTGAAGCATTCGACCAATAATGAAA
  54▸ Y   S   K   G   Q   M   D   R   S   S   V   S   K   R   N   K   Y   S   S   M   I   D   N   L   M   L   K   H   S   T   N   N   E
 595 ACAACAAAATTGAAGACTTTCACTTGAATCGCCCAAGGTCTGATCTAATCAGTAAATCTAAGCTGGAGATCAAACTCACTGACACCCTTCGTATTGCTA
  87▸ N   N   K   I   E   D   F   H   L   N   R   P   R   S   D   L   I   S   K   S   K   L   E   I   K   L   T   D   T   L   R   I   A
 694 TTGTGAAGATCAGGCAGTTTAGGGATATATTGACCCCACAGCTTTGAAAGGTATCGCCTTTACTTTGTACAAACTAATAAAACTTGGGGTGAGTCCCATAG
 120▸ I   V   K   I   R   Q   F   R   D   I   D   P   T   A   L   K   G   I   A   F   T   L   Y   K   L   I   K   L   G   V   S   P   I
 793 TGTTATTGGATACAGATAAAGAAGTTCAGGCTTTGAATGGAGAATCGGACGCCATGGTACAAAAAAGCATTGCCAATTACCATCAGCAGGCCCTGAGTT
 153▸ V   L   L   D   T   D   K   E   V   Q   A   L   N   G   E   S   D   A   M   V   Q   K   S   I   A   N   Y   H   Q   Q   A   L   S
 892 TCATAAATATCATTGAAAAATGTTTCCATAAATATGAGGATGACAACGAGCTCTCCGCAAGGGCCATCAGAGGTTTGTTCGAACAAAAATTTGATGAAG
 186▸ F   I   N   I   I   E   K   C   F   H   K   Y   E   D   D   N   E   L   S   A   R   A   I   R   G   L   F   E   Q   K   F   D   E
 991 ACAGATTTTCAATGACCCTACCAGAGCTATTACTAATTCCTATATCTCAGGGTATAGTCCCTGTTGTTTATCCTGTGGGATATATGGATAAGGGCTCCA
 219▸ D   R   F   S   M   T   L   P   E   L   L   L   I   P   I   S   Q   G   I   V   P   V   V   Y   P   V   G   Y   M   D   K   G   S
1090 AAAATGTATTTCTATCCTCCGAGGCAGTCCTCCAATGTTTAGCTACTGACTTGAAATCCTTGAATGATAGACATAGATTGGACCATGACAAGGAGAACT
 252▸ K   N   V   F   L   S   S   E   A   V   L   Q   C   L   A   T   D   L   K   S   L   N   D   R   H   R   L   D   H   D   K   E   N
1189 TATTCACAATTGAAAAGTACATTTTCATTGACCCATTGGGAGGTATCCCATCTTTGGAGAGGTACAAAAGTGCACATGTATATATCAATCTATTACAAG
 285▸ L   F   T   I   E   K   Y   I   F   I   D   P   L   G   G   I   P   S   L   E   R   Y   K   S   A   H   V   Y   I   N   L   L   Q
1288 AGTATGAAGACATTGTGTCGGAGCTTTACATAGGGTTCTTAAAGACTGGAGAAAGGGACCAGCATTTGAAGAACTTAAACTTGCTTCAGAAATTGTTGC
 318▸ E   Y   E   D   I   V   S   E   L   Y   I   G   F   L   K   T   G   E   R   D   Q   H   L   K   N   L   N   L   L   Q   K   L   L
1387 AGGTAACCACAGATGCATCAGGAATAGTTACTACTCCTCAAATCGCCATGTTGAATCAGACCGACCGATTCACCAATCCAATAATTTACAATGTCTTAA
 351▸ Q   V   T   T   D   A   S   G   I   V   T   T   P   Q   I   A   M   L   N   Q   T   D   R   F   T   N   P   I   I   Y   N   V   L
1486 CCGATAGGCCGACAATATCATCGTCATTACCGGTTGATTTGAAAAAGACCCCTTTGCTAAACACTTCAATCATTAGGAGAGGCGTACCGGTTGAAGTTT
 384▸ T   D   R   P   T   I   S   S   S   L   P   V   D   L   K   K   T   P   L   L   N   T   S   I   I   R   R   G   V   P   V   E   V
1585 ATGTGGACGAATCATCTGACAAAAGTGGGCTGTGCCTAGACTCTCTTCTGAAACGAGGAGCTTTAGACTTAGAAAAGCTTAAGAATGTGATCGATTTGT
 417▸ Y   V   D   E   S   S   D   K   S   G   L   C   L   D   S   L   L   K   R   G   A   L   D   L   E   K   L   K   N   V   I   D   L
1684 CGTTTCGAAAGGACTTGAATATGAAAAAGTACCTAGCCAGAGTAAAGAACAATGTTGCAGCTATCTTAATCGCTGGAGATTACGAAGGCGTGATCATAG
 450▸ S   F   R   K   D   L   N   M   K   K   Y   L   A   R   V   K   N   N   V   A   A   I   L   I   A   G   D   Y   E   G   V   I   I
1783 TTACTTGGGAGGTAACGGATGAAGAAAAGCCGCAGAAAATAGCTTATTTAGATAAGTTTGCAGTGTCTCCTAAGGCCCAAGGATCGACAGGGGTTGCCG
 483▸ V   T   W   E   V   T   D   E   E   K   P   Q   K   I   A   Y   L   D   K   F   A   V   S   P   K   A   Q   G   S   T   G   V   A
1882 ATGTTCTTTTCAAGTCATTATTGTCCAATTTTGAGAACGAATTGTTCTGGAGATCTCGATCTAATAATCCAGTGAACAAATGGTACTTTGAACGGAGCA
 516▸ D   V   L   F   K   S   L   L   S   N   F   E   N   E   L   F   W   R   S   R   S   N   N   P   V   N   K   W   Y   F   E   R   S
1981 AAGGTTCTCTTACTGTTACTGGCACAAATTGGAAATGCTTCTACACCGGCAAGAACTATCCTTCATTGGATAGAATGAAGGGCTATTTCAACATCTGTG
 549▸ K   G   S   L   T   V   T   G   T   N   W   K   C   F   Y   T   G   K   N   Y   P   S   L   D   R   M   K   G   Y   F   N   I   C
2080 AGAGAATCCAACCTTCCTGGAATGGATAAAGACGAGATCAATTAGAACCTGTTTTGGCAATAACCGAGGATTAGGAACAAAGTCCGGGTAATTATGCGA
 582▸ E   R   I   Q   P   S   W   N   G
2179 CTCTCTCTTTTTCATATGCAGGTCGAGCAAGAATCTTGTTTTTCGTGGTGGGACTGGGCAGCAATTAACAACCAATCGGCACTTGCAATAAGTCGATTA
2278 GCGCATGGTGGGGACAGTAGATAGCTGCTGAAATTTTTGGGTGCGGACAATTTCAAGAGTCTGAGGCCCTGCTCTCACTAGCAGTCAGAATCATCTGC
2377 CTCACATACAGTCTCCTGATGCTGCTACTTACTTGGCAAGCGATGATGTTTACACAATTGCAGCTTTTTAGTTGCTGTCATGGCTCTAGAATTCCTTGG
2476 CC
```

FIG 2B

```
1   M L S I K D F T S N L T R H A R N T E E K R N M V L T I L N S T A T K R E V R N   PpARG2
1   M W R - R I F A H E L - K Y D Q P N A S S K N L I L S V L N T T A T K R E A K D   ScARG2

41  Y L K K Y P L L K D V D I Y S K G Q M D R S S V S K R N K Y S S M I D N L M L K   PpARG2
39  Y L S K Y T - - - - - - - N D S G Q H N H C - - - - - - - - - - - - - L F F -   ScARG2

81  H S T N N E N N K I E D F H L N R P R S D L I S K S K L E I K L T D T L R I A I   PpARG2
57  - - - - - - - - - - - - - - - - - - - - - - - - - - - - - - - - - - - - - -   ScARG2

121 V K I R Q F R D I D P T A L K G I A F T L Y K L I K L G V S P I V L L D T D K E   PpARG2
57  - - I R D L H K V A P A I L S Q F S S V I K R L G M L G L R P M F V I P P S P T   ScARG2

161 V Q A L N G E S D A M V Q K S I A N Y H Q Q A L S F I N I I E K C F H K Y E D D   PpARG2
95  H V N I Q A E - - - L L D S I V T E A D L K P L H L K E G L T K - - - - - - - -   ScARG2

201 N E L S A R A I R G L F E Q K F - D E D R F S M T L P E L L L I P I S Q G - I V   PpARG2
124 - - - - S R T - - G L Y H S V F S Q E S R F - - - - - - - - - F D I G N S N F I   ScARG2

239 P V V Y P V G Y M D K G S K N V F L S S E A V - - L Q C L A T D L K S L N D R H   PpARG2
149 P I V K P Y V Y N E E T A S E - F M T K D V V K F M D C L C - - - - - - - - - -   ScARG2

277 R L D H D K E N L F T I E K Y I F I D P L G G I P S L E R Y K S A H V Y I N L L   PpARG2
178 - - - - - Q G N I P H I D K F F I L N N A G G I P S G E R N D N A H V F I N L S   ScARG2

317 Q E Y E D I V S E L Y I G - - - - - - - - - - - - - - - - - - - F L K T G E R   PpARG2
213 Q E L E H L S S S L S H N I S T L T K R E P R S Q N L L H R M E V Y V K K D E I   ScARG2

337 - - - - - - - D Q H L K N L N L L Q K L L - Q V T T D A S G I V T T P Q I A M L   PpARG2
253 S S L E C E Y H D H L E N L L L M D K V L S N L A A T A T G L I T T V K A A A L   ScARG2

369 N Q T D R F T N P I I Y N V L T D R P T I S S S L P V D L K K T - - - - - - - -   PpARG2
293 S - S D R - K N P L V Y N L L T D R S L I S S S L P R F K K K D G E I D S P A N   ScARG2

401 - - - - - - - - - - - - - - - - - - - - - P L L N T S I I R R G V P V E V Y   PpARG2
331 M F D D H A W Y E L P S Q Q V N A A P S N S D A V L V T T V L K K G V H I K T Y   ScARG2

418 V D E S S D K - S G L C L D S L L K - - - R G A - - - - - - - - L D L E K L K N   PpARG2
371 D Y K T L T Q F N S I G L P K K F H V P E K G A K P S S N S P K L D I N K F K S   ScARG2

446 V I D L S F R K D L N M K K Y L A R V K N N V A A I L I A G D Y E G V I I V T W   PpARG2
411 I I D Q S F K R S L D L H D Y I K R I N G K I A T I I V I G D Y E G I A I L T Y   ScARG2

486 E V T D E E K P Q K I A Y L D K F A V S P K A Q G S T G V A D V L F K S L L S N   PpARG2
451 E G S E E N S - - - F V Y L D K F A V L P H L K G S L G I S D I I F N L M F K K   ScARG2

526 F E N E L F W R S R S N N P V N K W Y F E R S K G S L T V T - - - - - - - - - -   PpARG2
488 F P N E I L W R S R K D N V V N K W Y F Q R S V A V L D L S I D L D P E H C D E   ScARG2

556 - G T N W K C F Y T G K - N Y P S L D - - - - - R M K G Y F N I C E R I Q P S W   PpARG2
528 K Q S Q F K L F Y Y G N P Q Y A K R A L R D K K R L R E F M R S V R D I K P S W   ScARG2

589 N - - - - - G                                                                     PpARG2
568 E N E K N I S                                                                     ScARG2
```

FIG 3A

```
   1 GGGTGTTATTTTCAAGTAAGAGTCATTTGAGGTAAGCACCAAACCGAGTAGTGAATGAGCAAAGAATTTTATGCTTATGTAATTGTTTTATTTGTTCCA
 100 TTCGAACGTTATAAACTGTGATTAAAACGGGTATATTTCAATTCCACGCGGAAGCGTAGTCAGAATACAAACCCACAATTAAGATGGACAGCTTGGCCG
 199 CTAACAGTAACAAAAACTACCGCCAGTTTTTCCTTTTGTCTTTCAAGCCATCTTCCAATCATTAATCAGTGTCAAGTTCGCCTTGAAAGACAAAAAAAA
 298 CACAGAAAGTCCTAAAAGTGTGAGCAATGATCTAAAGATTTGGCTTCATGATAGATTACTTTAGAGTAGCTGGCAATGAATTGGGATCTGAACTTTTGT
 397 CGTCTTTCTTTCCCTTAATTTAGTATCCAGCTGCAAGTGACTGAAAAAGGAAATTTTTCCACCGCGGAAAACTAACGATGCTTGGATGAGTAAAAAGTG
 496 AACAATTACTCAAATACTTCTCCTCAACTGAAAAATGAGCATGTTTAAGATCCCTAAGTTAGTGTTATCTCAAGGATTTCCAAGCCTAAATAGAAAACT
                                          1▶ M  S  M  F  K  I  P  K  L  V  L  S  Q  G  F  P  S  L  N  R  K  L
 595 AGCTCAGACTACCAAACCTCCAAGGTCCTTAATCTCCATCTTGGAACTAAGTAACCAAGAACTAAGTTCATTGGTTGAAAGAGCAGCATACCACAAGAC
  22▶ A  Q  T  T  K  P  P  R  S  L  I  S  I  L  E  L  S  N  Q  E  L  S  S  L  V  E  R  A  A  Y  H  K  T
 694 ACAATATAAGTCAGGCAAAATCTCCTCTCAGGTATCACCGTCGCTGTTTGGAAAAGTTGCAGCCCTTCTTTTTACAAAAAGATCCACTAGAACAAGAAT
  55▶ Q  Y  K  S  G  K  I  S  S  Q  V  S  P  S  L  F  G  K  V  A  A  L  L  F  T  K  R  S  T  R  T  R  I
 793 ATCCAGCGAGGGAGCAGCAGTGTATTTCGGGGCACACCCCATGTTTCTAGGTAAGGATGATATTCAGCTTGGAGTCAACGAGTCCTTCTATGACACTAC
  88▶ S  S  E  G  A  A  V  Y  F  G  A  H  P  M  F  L  G  K  D  D  I  Q  L  G  V  N  E  S  F  Y  D  T  T
 892 GAAAGTGATCTCCTCTATGACGTCTTGTATCTTTGCCCGTGTTGATAAACATTCTCAAATCCAAGAACTTGCTCAACATTCCACAGTGCCTATCATAAA
 121▶ K  V  I  S  S  M  T  S  C  I  F  A  R  V  D  K  H  S  Q  I  Q  E  L  A  Q  H  S  T  V  P  I  I  N
 991 TTCTTTGTGTGATAGATTCCACCCATTGCAGGCTATTACAGATATTCTGACCATTCGTGAGGCATTCGGCTTCACCAAAGGTCTAAAGTTGGCTTGGGT
 154▶ S  L  C  D  R  F  H  P  L  Q  A  I  T  D  I  L  T  I  R  E  A  F  G  F  T  K  G  L  K  L  A  W  V
1090 AGGTGATTCCAACAATGTCATCAATGATCTTGCAATCGCAGCCATTCGTTCTGGAATTAACGTTTCAATTGCCATTCCTCAAGGAATAGAAATGGATGA
 187▶ G  D  S  N  N  V  I  N  D  L  A  I  A  A  I  R  S  G  I  N  V  S  I  A  I  P  Q  G  I  E  M  D  E
1189 GGAAATTATTTCCAAAGGCCAACAGATTGCACAGGAAACAGACACTGTTTTGGAAGTTACTCATGACCCAAAGAAGGCTGTCAAAGATGCCAATGTCCT
 220▶ E  I  I  S  K  G  Q  Q  I  A  Q  E  T  D  T  V  L  E  V  T  H  D  P  K  K  A  V  K  D  A  N  V  L
1288 TGTCACAGACACCTTTGTCTCTATGGGACAAGAAGCAGAATCCAAGGCAAAATTGGCTCAATTTCAAGGTTTTCAAATCTCTAGTGACTTGGCTTCAGG
 253▶ V  T  D  T  F  V  S  M  G  Q  E  A  E  S  K  A  K  L  A  Q  F  Q  G  F  Q  I  S  S  D  L  A  S  G
1387 TGCTGCCCCGGATTGGAAATTCATGCACTGCTTGCCGCGTCATAAAGAGGAAGTGACCGACGAAGTTTTCTACTCTGACCGTTCTTTGGTGTTCCCCGA
 286▶ A  A  P  D  W  K  F  M  H  C  L  P  R  H  K  E  E  V  T  D  E  V  F  Y  S  D  R  S  L  V  F  P  E
1486 GGCCGAGAACCGATTGTACGCTGCCATTGCTGCCCTTGAAGGATTCGTTATCAACGAAGGTCGTTTGGTATAAATAAATTACACGGATTTATGCTTGAT
 319▶ A  E  N  R  L  Y  A  A  I  A  A  L  E  G  F  V  I  N  E  G  R  L  V
1585 CACATGACCAATCATAACTAGGCGGACCATGCTGCCTCCTGCAAAGGTTCTCGTTCCCAATTTCTTAAAGTCTTATGTAATCAACCTGTATTTTCTTGC
1684 TTGACGCGCCCCAAAGAAATCAAAACAATCCCCTTCGAAACATTGTTAACTTTGAATTAACTCCTCAATAGTTCCTGAAAACAGCTTTCTCTGGTCGCA
1783 CGGTCTGGTTCCCCTTTGCATAATCATCTTTGACTTATGCTAGACAAAAATAGAATCTTGCGAATCCGCAAGAAGAAAGATGGCTCCG
```

FIG 3B

```
1    MSMFKIPKLVLSQGFPSLNRKLAQTTKPPRSLISILELSN  PpARG3
1    MS--------------------TTASTPSSLRHLISIKDLSD  ScARG3

41   QELSSLVERAAYHKTQYKSGKISSQVSP--SLFGKVAALL  PpARG3
23   EEFRILVQRAQHFKNVFKANKTNDFQSNHLKLLGRTIALI  ScARG3

79   FTKRSTRTRISSEGAAVYFGAHPMFLGKDDIQLGVNESFY  PpARG3
63   FTKRSTRTRISTEGAATFFGAQPMFLGKEDIQLGVNESFY  ScARG3

119  DTTKVISSMTSCIFARVDKHSQIQELAQHSTVPIINSLCD  PpARG3
103  DTTKVVSSMVSCIFARVNKHEDILAFCKDSSVPIINSLCD  ScARG3

159  RFHPLQAITDILTIREAF---------GFTKGLKLAWVGD  PpARG3
143  KFHPLQAICDLLTIIENFNISLDEVNKGINSKLKMAWIGD  ScARG3

190  SNNVINDLAIAAIRSGINVSIAIPQGIEMDEEISKGQQI  PpARG3
183  ANNVINDMCIACLKFGISVSISTPPGIEMDSDIVDEAKKV  ScARG3

230  AQETDTVLEVTHDPKKAVKDANVLVTDTFVSMGQEAESKA  PpARG3
223  AERNGATFELTHDSLKASTNANILVTDTFVSMGEEFAKQA  ScARG3

270  KLAQFQGFQISSDLASGAAPDWKFMHCLPRHKEEVTDEVF  PpARG3
263  KLKQFKGFQINQELVSVADPNYKFMHCLPRHQEEVSDDVF  ScARG3

310  YSDRSLVFPEAENRLYAAIAALEGFVINEGR---LV     PpARG3
303  YGEHSIVFEEAENRLYAAMSAIDIFVNNKGNFKDLK     ScARG3
```

FIG 4A

```
   1 CAAGTTGCGTCCGGTATACGTAACGTCTCACGATGATCAAAGATAATACTTAATCTTCATGGTCTACTGAATAACTCATTTAAACAATTGACTAATTGT
 100 ACATTATATTGAACTTATGCATCCTATTAACGTAATCTTCTGGCTTCTCTCTCAGACTCCATCAGACACAGAATATCGTTCTCTCTAACTGGTCCTTTG
 199 ACGTTTCTGACAATAGTTCTAGAGGAGTCGTCCAAAAACTCAACTCTGACTTGGGTGACACCACCACGGGATCCGGTTCTTCCGAGGACCTTGATGACC
 298 TTGGCTAATGTAACTGGAGTTTTAGTATCCATTTTAAGATGTGTGTTTCTGTAGGTTCTGGGTTGGAAAAAAATTTTAGACACCAGAAGAGAGGAGTGA
 397 ACTGGTTTGCGTGGGTTTAGACTGTGTAAGGCACTACTCTGTCGAAGTTTTAGATAGGGGTTACCCGCTCCGATGCATGGGAAGCGATTAGCCCGGCTG
 496 TTGCCCGTTTGGTTTTTGAAGGGTAATTTTCAATATCTCTGTTTGAGTCATCAATTTCATATTCAAAGATTCAAAAACAAAATCTGGTCCAAGGAGCGC
 595 ATTTAGGATTATGGAGTTGGCGAATCACTTGAACGATAGACTATTATTTGCTGTTCCTAAAAGTATGTAGCATGTCGTTTTTTTTTTAAAAGGGTTTTT
         1▶  M  E  L  A  N  H  L  N  D  R  L  L  F  A  V  P  K
 694 TCCCTATTCTCCACTCACTTTATACTAACAACTATTTTTTTCAGAGGGCAGATTGTATGAGAAATGCGTTGAATTACTTAGGGGATCAGATATTCAGTT
                        18▶  E  G  R  L  Y  E  K  C  V  E  L  L  R  G  S  D  I  Q  F
 793 TCGAAGATCCAGTAGATTGGATATAGCTTTGTGCACTAACCTGCCCCTGGCATTGGTTTTCCTTCCAGCTGCTGACATTCCCACGTTTGTAGGAGAGGG
      36▶  R  R  S  S  R  L  D  I  A  L  C  T  N  L  P  L  A  L  V  F  L  P  A  A  D  I  P  T  F  V  G  E  G
 892 TAAATGTGATTTGGGTATAACTGGTATTGACCAGGTTCAGGAAAGTGACGTAGATGTCATACCTTTATTAGACTTGAATTTCGGTAAGTGCAAGTTGCA
      69▶  K  C  D  L  G  I  T  G  I  D  Q  V  Q  E  S  D  V  D  V  I  P  L  L  D  L  N  F  G  K  C  K  L  Q
 991 GATTCAAGTTCCCGAGAATGGTGACTTGAAAGAACCTAAACAGCTAATTGGTAAAGAAATTGTTTCCTCCTTTACTAGCTTAACCACCAGGTACTTTGA
     102▶  I  Q  V  P  E  N  G  D  L  K  E  P  K  Q  L  I  G  K  E  I  V  S  S  F  T  S  L  T  T  R  Y  F  E
1090 ACAACTGGAAGGAGTTAAGCCTGGTGAGCCACTAAAGACAAAAATCAAATATGTTGGAGGGTCTGTTGAGGCCTCTTGTGCCCTAGGAGTTGCCGATGC
     135▶  Q  L  E  G  V  K  P  G  E  P  L  K  T  K  I  K  Y  V  G  G  S  V  E  A  S  C  A  L  G  V  A  D  A
1189 TATTGTGGATCTTGTTGAGAGTGGAGAAACCATGAAAGCGGCAGGGCTGATCGATATTGAAACTGTTCTTTCTACTTCCGCTTACCTGATCTCTTCAA
     168▶  I  V  D  L  V  E  S  G  E  T  M  K  A  A  G  L  I  D  I  E  T  V  L  S  T  S  A  Y  L  I  S  S  K
1288 GCATCCTCAACACCCAGAACTGATGGATACTATCAAGGAGAGAATTGAAGGTGTACTGACTGCTCAGAAGTATGTCTTGTGTAATTACAACGCACCTAG
     201▶  H  P  Q  H  P  E  L  M  D  T  I  K  E  R  I  E  G  V  L  T  A  Q  K  Y  V  L  C  N  Y  N  A  P  R
1387 AGGTAACCTTCCTCAGCTGCTAAAACTGACTCCAGGCAAGAGAGCTGCTACCGTTTCTCCATTAGATGAAGAAGATTGGGTGGGAGTGTCCTCGATGGT
     234▶  G  N  L  P  Q  L  L  K  L  T  P  G  K  R  A  A  T  V  S  P  L  D  E  E  D  W  V  G  V  S  S  M  V
1486 AGAGAAGAAAGATGTTGGAAGAATCATGGACGAATTAAAGAAACAAGGTGCCAGTGACATTCTTGTCTTTGAGATCAGTAATTGTAGAGCATAGATAGA
     267▶  E  K  K  D  V  G  R  I  M  D  E  L  K  K  Q  G  A  S  D  I  L  V  F  E  I  S  N  C  R  A
1585 ATAATATTCAAGACCAACGGCTTCTCTTCGGAAGCTCCAAGTAGCTTATAGTGATGAGTACCGGCATATATTTATAGGCTTAAAATTTCGAGGGTTCAC
1684 TATATTCGTTTAGTGGGAAGAGTTCCTTTCACTCTTGTTATCTATATTGTCAGCGTGGACTGTTTATAACTGTACCAACTTAGTTTCTTTCAACTCCAG
1783 GTTAAGAGACATAAATGTCCTTTGATGC
```

FIG 4B

```
1   M E L A N H L N D R L L F A V P K E G R L Y E K C V E L L R G S D I Q F R R S S   PpHIS1
1   M D L V N H L T D R L L F A I P K K G R L Y S K S V S I L N G A D I T F H R S Q   ScHIS1

41  R L D I A L C T N L P L A L V F L P A A D I P T F V G E G K C D L G I T G I D Q   PpHIS1
41  R L D I A L S T S L P V A L V F L P A A D I P T F V G E G K C D L G I T G V D Q   ScHIS1

81  V Q E S D V D V I P L L D L N F G K C K L Q I Q V P E N G D L K E P K Q L I G K   PpHIS1
81  V R E S N V D V D L A I D L Q F G N C K L Q V Q V P V N G E Y K K P E Q L I G K   ScHIS1

121 E I V S S F T S L T T R Y F E Q L E G V K P G E P L K T K I K Y V G G S V E A S   PpHIS1
121 T I V T S F V K L A E K Y F A D L E G T T V - E K M T T R I K F V S G S V E A S   ScHIS1

161 C A L G V A D A I V D L V E S G E T M K A A G L I D I E T V L S T S A Y L I S S   PpHIS1
160 C A L G I G D A I V D L V E S G E T M R A A G L V D I A T V L S T S A Y L I E S   ScHIS1

201 K H P Q - H P E L M D T I K E R I E G V L T A Q K Y V L C N Y N A P R G N L P Q   PpHIS1
200 K N P K S D K S L I A T I K S R I E G V M T A Q R F V S C I Y N A P E D K L P E   ScHIS1

240 L L K L T P G K R A A T V S P L D E E D W V G V S S M V E K K D V G R I M D E L   PpHIS1
240 L L K V T P G R R A P T I S K I D D E G W V A V S S M I E R K T K G V V L D E L   ScHIS1

280 K K Q G A S D I L V F E I S N C R A                                               PpHIS1
280 K R L G A S D I M V F E I S N C R V                                               ScHIS1
```

FIG 5A

```
   1 CGATTGCTCATCTTCAGAAGAAGTCTTCAAATGAGGAATTGAAGAGTTATCAAGTTAAGTGGCAAGAATAGAAACTTTAAAATTAAGGGTTTCCAGTTG
 100 TGCATTTATAGGGATATAAGAAATGAAAACAAAACATTTTCGGAATCGGAAACTCTTTCTTCCGAATTTCCGTTTCCGAAGACATAACATTGATTCTCC
 199 AGGTCTAAATTTAGGAAAAATGCCAAAAAAAAGCGACTGAGCATCTGCATCGATCGGAGTAGACAACTGGTTAGTTGCCGTGCCTCTCAGAACCAAAGT
 298 TGAGCTGGTTAACGTCTGACTTGACAGCGGAACTTGGAATCTTCGGAAGACTCTAGGATGCCTAAATTTTCGATGCCTCCAAAATCTCAATGTGGCTTA
 397 CGGGAATCTACGGCTCACCTTACAACGAAATTGGGACAATCAGCAAGCAGTCTATCGATCGTTGTTTACAAAATATTTCGCTACCAAGAAGAGACACCC
 496 CGTTTGTTGGGGAGTACGGATTGTTGATTACCAATCGCCAATTTCCGGGGCTTACCATGATTATGCATAACTTCTCGGAATTAGGTCTTGAACTGAAAT
 595 TACTCATGCTCAGTGCATACACTTATCCCTAGCCGCATTGACTCTGTGAGCTTCCGGAGTGTTAGTAGTTCCGACCGTTAGATAATCGTGCTTTCTTTC
 694 TTTTTTAGTGTTGTTGTATTATTAATACGATGCTGGTGGCTTAGAAATAGCGATCGTGACTGCGATGTCTAGTCGCCTGATGAGTTGACTTCTTCCTCC
 793 CTCCGGTTTCACCCACTACTAGGCTTAGCAGTTCTTGGCTTTTCTGTCCCCCTCGCGGAAATGTTCTCACGTCTTCCGCCTAACAGATTGTTCTGGCGG
 892 TTTTAGTCGTCTAGCTATTGATGCATTCCCATCATTCCCATAGTGGAAGTTACGTTTCTCATGCAACGGATACACTGGATGAAATCGTAGACAAAGCTA
     1► M  H  S  H  H  H  S  H  S  G  S  Y  V  S  H  A  T  D  T  L  D  E  I  V  D  K  A
 991 TTGAGCTCCATTTCCAAACATATTGTCTCACTGAACATATGCCCAGATATAAGGATGAAGATCTCTATCCTGAAGAAATTGAAAAGAGGTTTACCTATA
    27► I  E  L  H  F  Q  T  Y  C  L  T  E  H  M  P  R  Y  K  D  E  D  L  Y  P  E  E  I  E  K  R  F  T  Y
1090 AGTGTCTGGTCGAACAATTTGACCAGTTTTATAAGCATGCAAAAGTTATAAAAGAGACAAGGAACATTGATCCCCAGTGTGATACAAGATTTCTTATAG
    60► K  C  L  V  E  Q  F  D  Q  F  Y  K  H  A  K  V  I  K  E  T  R  N  I  D  P  Q  C  D  T  R  F  L  I
1189 GGTTTGAAACTGAAGGAGGTCTTGGTGATTATCAACTGGATCAATGTTTGAAATTACGCCTGACATATCCTGTTGACTTGACTTGTTGGATCGATACACC
    93► G  F  E  T  E  G  G  L  G  D  Y  Q  L  D  Q  C  L  K  L  R  L  T  Y  P  V  D  L  I  V  G  S  I  H
1288 ATTTAGACTCCATTCCTATTGATATCGATAGGGCAAACTGGCTAAAAGCCAAAGATGCAACAACTTCGAATGGTTCGATCAGAGACTTCTATTTTCTCT
   126► H  L  D  S  I  P  I  D  I  D  R  A  N  W  L  K  A  K  D  A  T  T  S  N  G  S  I  R  D  F  Y  F  L
1387 ACTTCAAAACTCAACAATTAATGATTCAAAAACTAAGGCCAGAAGTGATCGGGCATTTTGACCTCATAAGATTTTACAACGAAGATGGCCACCAATTAT
   159► Y  F  K  T  Q  Q  L  M  I  Q  K  L  R  P  E  V  I  G  H  F  D  L  I  R  F  Y  N  E  D  G  D  Q  L
1486 TTCAATGGCCAGAGGTAGTAGCCGTTAATTGAAGAGAATATAGACTTGATAAATTCGTATGATGGATTAATTGAGCTCAATTCAGCTGCTATTAGGAAAG
   192► F  Q  W  P  E  V  V  A  L  I  E  E  N  I  D  L  I  N  S  Y  D  G  L  I  E  L  N  S  A  A  I  R  K
1585 GTTGGCCGTCTCCATACCCAAAATCTGATGTCATCAATTTTATTTTTAGTAGAGGAGGAAAATTTTGCTTTAGCGATGACGCCCATAGTGTGGGACAAG
   225► G  W  P  S  P  Y  P  K  S  D  V  I  N  F  I  F  S  R  G  G  K  F  C  F  S  D  D  A  H  S  V  G  Q
1684 TTGGCTTAAACTACATGAAAATGCTAGAGTTTGTTGAACAATCGACAGAAATTGACAAGATCTGGTACTATGATTTGAGCAACACTGATAAACTTATTC
   258► V  G  L  N  Y  M  K  M  L  E  F  V  E  Q  S  T  E  I  D  K  I  W  Y  Y  D  L  S  N  T  D  K  L  I
1783 AAAAGAGTATTCCAGTTTCTAGATTAAGGGACCATGTATTCTGGAATTCAGGCTAAATAAATCTAATCACGTATTATAGGCGAGAGTATCAATTTTATC
   291► Q  K  S  I  P  V  S  R  L  R  D  H  V  F  W  N  S  G
1882 CCAGACGTTGTTATAATGAGTTAGCATTTCTTCGAATCCCACTAAGTTATAAGTTCTAAGTGTTTTCCATCTATTGTTCACTTGGCCTTCATCCAAAGA
1981 AAACAACTTTTGCAATCCGAGTTTAACATCTTTTTTAGCCTTTGCTTTATTTATTGGTACTCCATATTTGATGGAGATATCTTCAACC
```

FIG 5B

```
1   M H S H H S H S G S Y V S H A T D T L D E I V D K A I E L H F Q T Y C L T E H M   PpHIS2
1   M H S H H S H S G D Y S A H G T D P L D S V V D Q V V N L N F H T Y C L T E H I   ScHIS2

41  P R Y K D E D L Y P E E - - I E K R F T - - Y K C L V E Q F D Q F Y K H A K V I   PpHIS2
41  P R I E A K F I Y P E E Q S L G K N P E E V I T K L E T S F K N F M S H A Q E I   ScHIS2

77  K E T R N I D P Q C D T R F L I G F E T E G - G L G D Y Q L D Q C L K L R L T Y   PpHIS2
81  K T R Y A D R P D V R T K F I I G M E I E S C D M A H I E Y A K R L M K E N N D   ScHIS2

116 P V D L I V G S I H H L D S I P I D I D R A N W L K A K D A T T S N G S I R D F   PpHIS2
121 I L K F C V G S V H H V N G I P I D F D Q Q Q W Y N S L H S F - - N D N L K H F   ScHIS2

156 Y F L Y F K T Q Q L M I Q K L R P E V I G H F D L I R F Y - - - - - - - - - - -   PpHIS2
159 L L S Y F Q S Q Y E M L I N I K P L V V G H F D L Y K L F L P N D M L V N Q K S   ScHIS2

185 - - - - N E D G - - - - - - D Q L F Q W P E V V A L I E E N I D L I N S Y D G L   PpHIS2
199 G N C N E E T G V P V A S L D V I S E W P E I Y D A V V R N L Q F I D S Y G G A   ScHIS2

215 I E L N S A A I R K G W P S P Y P K S D V I N F I F S R - G G K F C F S D D A H   PpHIS2
239 I E I N T S A L R K R L E E P Y P S K T L C N L V K K H C G S R F V L S D D A H   ScHIS2

254 S V G Q V G L N Y M K M L E F V E Q S T E I D K I W Y Y D L S N T D K - - L I Q   PpHIS2
279 G V A Q V G V C Y D K V K K Y I V D V L Q L E Y I C Y L E E S Q S P E N L L T V   ScHIS2

292 K S I P V S R L R D H V F W N S G                                                 PpHIS2
319 K R L P I S Q F V N D P F W A N I                                                 ScHIS2
```

FIG 6A

```
   1 GCAAAATGCTTTCTGGAACTCAAGGGTCTTGTGGCTTCAATTCTGACAATATCTCCCTCTTTACAAATGTTACCCTCATCATGAACAAGATAGTTTTTC
 100 CTCTTGAACAAAGACTTGTGAATCTTTGTGTTATACGCCATTTGCTCTACGCGTACTTTGACAGTTTTATCCATCTTACCTTGTGAAACCACAAGGCCT
 199 ATAAAGTTCTGCCTGGCCATTTGTTCGATTTTTGGATATGTCTTTGAGTAAAATTTTGAAGCTCAACTAACATGTCCAATTTTCAGTAGAGATACACGA
 298 CCTATAATTTTCGCAGGCTCTCTGACGCTTAAGGAAGCACGGCAGGTCCAATTTAGAGATTGTGACTCAGATCTCTGAAGCCTCTACATACAACATACA
 397 ATTTGCAATTTTTTGAGCTAGTATCATGGTTTTTGACTACAAGAGACTGGTTAGACCTAACATCTTGAGTTTGGAGCCTTACAGATGCGCCCGTGACG
       1▶ M  V  F  D  Y  K  R  L  V  R  P  N  I  L  S  L  E  P  Y  R  C  A  R  D
 496 ATTTTAAGGAAGGAATTCTGCTTGATGCTAATGAAAATACTCATGGACCTAGTATATCTGACCTTAGCACCTCAGAGGATGACTTGCAACTTAACAGAT
      25▶D  F  K  E  G  I  L  L  D  A  N  E  N  T  H  G  P  S  I  S  D  L  S  T  S  E  D  D  L  Q  L  N  R
 595 ATCCTGATCCTCATCAGTTGGAGCTAAAGCAACAAATCTGTAATATTAGAAATCAAGAAACCCCCATCGAAGGGGAGAAAGTTGAGGTGGAGAACTTAT
      58▶Y  P  D  P  H  Q  L  E  L  K  Q  Q  I  C  N  I  R  N  Q  E  T  P  I  E  G  E  K  V  E  V  E  N  L
 694 GCCTGGGTGTGGGTTCTGACGAAAGTATTGACGCCTTGATGAGATGTTTTTTGACCCCTTCAAAAGATAAACTATTGATTTGTACACCTACTTATGGGA
      91▶C  L  G  V  G  S  D  E  S  I  D  A  L  M  R  C  F  L  T  P  S  K  D  K  L  L  I  C  T  P  T  Y  G
 793 TGTATGGAATCTGTGCTACGATTAATGACATTGAAATTGTGAAATGTCCTTTGAACTTGCAGAGCTTCCAGATACAACCGGAAGAAATCTTGAAAGTTG
     124▶M  Y  G  I  C  A  T  I  N  D  I  E  I  V  K  C  P  L  N  L  Q  S  F  Q  I  Q  P  E  E  I  L  K  V
 892 TTCAAAATGATCCTACTATCAAGTTACTTTATCTCACTTCTCCTGGTAATCCAACAGGCCAATTAATTGACTTCAGTCTGGTAGAGACAATTTTAAACG
     157▶V  Q  N  D  P  T  I  K  L  L  Y  L  T  S  P  G  N  P  T  G  Q  L  I  D  F  S  L  V  E  T  I  L  N
 991 CGTGGGAAGGTGGTATCGTCATACTGGATGAGGCATATATATTGATTTTTCACCCGTGGGATCGTCTAGAAGCACCCTGGTCAACAAATATCCGAACTTGA
     190▶A  W  E  G  I  V  I  L  D  E  A  Y  I  D  F  S  P  V  G  S  S  R  S  T  L  V  N  K  Y  P  N  L
1090 TCGTACTTCAGACTCTTTCTAAAGCATTTGGTCTAGCGGGTATAAGACTTGGTATCACATTTGCCAGCAAACCAATTTCCGCGTTGCTGAATGCGTTAA
     223▶I  V  L  Q  T  L  S  K  A  F  G  L  A  G  I  R  L  G  I  T  F  A  S  K  P  I  S  A  L  L  N  A  L
1189 AGTACCCTTACAATATTTCCAATCTGACTTCTAATATTGCTTTGAGAGCTACGTTGCCTGAGAACGTCCAAGAAATGAGAAGCAAATGCAAAGCAATCT
     256▶K  Y  P  Y  N  I  S  N  L  T  S  N  I  A  L  R  A  T  L  P  E  N  V  Q  E  M  R  S  K  C  K  A  I
1288 GCAATGAAAGGGAGTTTGTCATAGATTCCCTGACAAAACTACCAAACGTCGGCCGCGTCATTGGCGGCCTAGATGCCAACTTCATTCTTTTGCAATTTC
     289▶C  N  E  R  E  F  V  I  D  S  L  T  K  L  P  N  V  G  R  V  I  G  G  L  D  A  N  F  I  L  L  Q  F
1387 TTGATACAAATGGAAAACCCTCTAATGAGGTTGCCAAGAAGCTTTACACTACATTGGCCACCGAGAATAAGGTAGTTATTCGATACAGAGGAAGTGAAC
     322▶L  D  T  N  G  K  P  S  N  E  V  A  K  K  L  Y  T  T  L  A  T  E  N  K  V  V  I  R  Y  R  G  S  E
1486 TTGGATGCGAAGGTTGTTTGAGAATTAGTATTGGAACCAGAGAGGAAAACAATACTTTGATAGACCAAATGTCAAAAGTACTACCACAGGTTATCAAAT
     355▶L  G  C  E  G  C  L  R  I  S  I  G  T  R  E  E  N  N  T  L  I  D  Q  M  S  K  V  L  P  Q  V  I  K
1585 CATCTACATAGATAATCTTCATAATATAAATATACAGTTTTGTGGTCACGATGTCTTATCTCATCGTCTCATTTCTATTTAAACAGTTGCTCAACCAAT
     388▶S  S  T
1684 GCATTCAGCTTTCCGCTATAAAAGTCACCATGTTGAGGTCCGCTACCTTGGACGTTTTCTTCGTCGTTCAGATGCTTCTTGAGCTTATCTAATGACTCC
1783 AAATCCTTTTTGATACGATACCTTGGATCAAGTATATCAGAAAGACCAATTTCCACATCCTCTCCAGTGTTGGAAATTGCGGTGACACTAATTGCGCAA
1882 GATTCTAAAGCCAGAAGCTCACTTGGATGACCGCTGTCATCCTTGGG
```

FIG 6B

```
1   M V F D Y K R L V R P N I L S L E P Y R C A R D D F K E G I L L D A N E N T H G   PpHIS5
1   M V F D L K R I V R P K I Y N L E P Y R C A R D D F T E G I L L D A N E N A H G   ScHIS5

41  P S I S D L S T S E D D L Q L N R Y P D P H Q L E L K Q Q I C N I R N Q E T P I   PpHIS5
41  P T P V E L S K T N - - - - L H R Y P D P H Q L E F K T A M T K Y R N K T S S Y   ScHIS5

81  E G E K - - - - V E V E N L C L G V G S D E S I D A L M R C F L T P S K D K L L   PpHIS5
77  A N D P E V K P L T A D N L C L G V G S D E S I D A I I R A C C V P G K E K I L   ScHIS5

117 I C T P T Y G M Y G I C A T I N D I E I V K C P L N L Q - - S F Q I Q P E E I L   PpHIS5
117 V L P P T Y S M Y S V C A N I N D I E V V Q C P L T V S D G S F Q M D T E A V L   ScHIS5

155 K V V Q N D P T I K L L Y L T S P G N P T G Q L I D F S L V E T I L N A W E G G   PpHIS5
157 T I L K N D S L I K L M F V T S P G N P T G A K I K T S L I E K V L Q N W D N G   ScHIS5

195 I V I L D E A Y I D F S P V G S S R S T L V N K Y P N L I V L Q T L S K A F G L   PpHIS5
197 L V V D E A Y V D F C - - G G S T A P L V T K Y P N L V T L Q T L S K S F G L   ScHIS5

235 A G I R L G I T F A S K P I S A L L N A L K Y P Y N I S N L T S N I A L R A T L   PpHIS5
235 A G I R L G M T Y A T A E L A R I L N A M K A P Y N I S S L A S E Y A L K A V Q   ScHIS5

275 P E N V Q E M R S K C K A I C N E R E F V I D S L T K L P N V G - R V I G G L D   PpHIS5
275 D S N L K K M E A T S K I I N E E K M R L L K E L T A L D Y V D D Q Y V G G L D   ScHIS5

314 A N F I L L Q F L D T N G K P S N E V A K K L Y T T L A T E N K V V I R Y R G S   PpHIS5
315 A N F L L I R I N G G D - - - - N V L A K K L Y Q L A T Q S G V V V R F R G N   ScHIS5

354 E L G C E G C L R I S I G T R E E N N T L I D Q M S K V L P Q V I K S S T         PpHIS5
351 E L G C S G C L R I T V G T H E E N T H L I K Y F K E T L Y K L - - A N E         ScHIS5
```

FIG 7A

```
   1 CCGTTGGCAACATAAGGTTGCAGCTGGTAATTGTTATAGCGAGGGAATCTTGTAGTTCTCAGGACCTTTAGCTCTTTGTCGTAATATGTCTCAGTGTCT
 100 TCATCGACAAAATAAGTGGCTCCTGAACTGAGACCTTCAGAGATATTAGCTCTGGTGAAGTTGTGACTCAGAAGATTCCTAATCTGCAAGGAATCACTT
 199 GAAGTGCCAACAGGAAAGGTTGTAACCAAGTGAAAGAAAACCACACAAGAAAGGGCAACCAACAACACTCTATTCAGCATTTCTCTAGTCTGAGAGGTG
 298 GGAGGAGGTTTCTTTGGTATTCTGCTATTATATATGGATCCATACGGCATTGCCCTAATCTAGTGAAGTAAAAGCCAAATGTTCCGCATCGGTCCACGG
 397 AGAAATTTGATTGCTCTATCTGGCACCTGAAAGTTTGCGAGTTCCTAAATTAGAAATTTAGGTGCATTAAACATGGGGAATGTATGACTTTTTTTTTTC
 496 CGTCTTTGGGATCTTGCTCGCCAGATCGAGAGGTTTTGGAGTAAGTGCTCCACCATAGAAAAATAGTCCGTATGACTGTCTTCAGAGGTTGCATCGATA
                                                                                      1▶ M  T  V  F  R  G  C  I  D
 595 TCCATTCCGGCAAAGTCAAACAGATTGTAGGCGGCAAGCTGGTGAAGGATGACACTGAATCTGATGAAGTAGAAACAAATTTTGTCAGTGAACAGCCCT
  10▶ I  H  S  G  K  V  K  Q  I  V  G  G  K  L  V  K  D  D  T  E  S  D  E  V  E  T  N  F  V  S  E  Q  P
 694 CGTCCTATTATGCACAGTTATATAAGCAGAACCAGGTTCATGGAACACATGTCATCAAATTGGGCTCTTTAAAGGCTAATGACGACGCTGCAAGAGAAG
  43▶ S  S  Y  Y  A  Q  L  Y  K  Q  N  Q  V  H  G  T  H  V  I  K  L  G  S  L  K  A  N  D  D  A  A  R  E
 793 CTCTGGGTGCGTGGAGAGGGGGTTTGCAGATTGGCGGTGGAATAACGGATTCCAATGCTCAAGAATGGATAGATCAAGGTGCATCGCATGTCATAGTCA
  76▶ A  L  G  A  W  R  G  G  L  Q  I  G  G  I  T  D  S  N  A  Q  E  W  I  D  Q  G  A  S  H  V  I  V
 892 CTTCATGGTTATTCCCTGAGGGTCAGTTTTCTATAGAAAGACTTCAACACCTGTCCAGCCTTATTGGAAAAGAGAAACTGGTAGTGGACTTGAGTTGTC
 109▶ T  S  W  L  F  P  E  G  Q  F  S  I  E  R  L  Q  H  L  S  S  L  I  G  K  E  K  L  V  V  D  L  S  C
 991 GTAGACAAGAGATAGATGGAAGTCCCCAATGGGTGGTTGCTATGAACAAATGGCAAACATTGACCTCATCCGTGCTAGATAGAGAGTTTTTCCAACTGC
 142▶ R  R  Q  E  I  D  G  S  P  Q  W  V  V  A  M  N  K  W  Q  T  L  T  S  S  V  L  D  R  E  F  F  Q  L
1090 TGTCCCAGTATTGCGATGAGTTCTTAGTGCATGCTGCAGATGTGGAGGGACTTTGTCAAGGAATTGACCAAGAGCTGGTACGGAAATTAAGTGAATGGA
 175▶ L  S  Q  Y  C  D  E  F  L  V  H  A  A  D  V  E  G  L  C  Q  G  I  D  Q  E  L  V  R  K  L  S  E  W
1189 GTGATCTTCCAGTTACATATGCTGGTGGGGCTAGAAGTATACAAGATCTAGAAACTGTCAAACATTTAAGCAACGGAAAGGTCGATCTCACGTTTGGAA
 208▶ S  D  L  P  V  T  Y  A  G  G  A  R  S  I  Q  D  L  E  T  V  K  H  L  S  N  G  K  V  D  L  T  F  G
1288 GTGCACTGAATATTTTTGGCGGAAACCTAGTAAAGTTTGAAGACTGTGTTAAGTGGAATAAAACTCAGTAGATGCTACCTTAGTTTATAGTTAATAGT
 241▶ S  A  L  N  I  F  G  G  N  L  V  K  F  E  D  C  V  K  W  N  K  T  Q
1387 AGAGGGTCTGGTCAGCCCTAGGCTTCCAAAAATCCGTATACCTGCGTTTCTTCCGCTTGCGAATATCTTTCTCAATGCTGGTCTTAGTATGTACAAAAG
1486 CTCTGCCCACAAGAAGCCTTGGATAAATGGTTTGATAACATGGTCAATTGCAATTGTATAAGCGACAACTTTGGCGGTTACCTGGGCTTAGCGGAGGA
1585 AATGCGAACTGAATTTGCATTAAGAGTCCTCCAAAATGATTGCTCGTAACGGAGATCGGGGATGACTAATGTGTTCATGATGGTCGATGAGCCAAGAGG
1684 GGGGTTGGACTGGGTCAACCTTGGATAAGCTAAAAAAGGGAGCCCCGCGAAGGGTCTCCCTGAAGCAAACCCTTGCACGGAAGGAAGAGGTTTTCGCTT
1783 TGGGCGCGGTAGTTCAATTCAACG
```

FIG 7B

```
1   M T V F R G C I D I H S G K V K Q I V G G K L V K D D T E S D E V E T N F V S E   PpHIS6
1   M T K F I G C I D L H N G E V K Q I V G G T L T S K K E D V P K - - T N F V S Q   ScHIS6

41  Q P S S Y Y A Q L Y K Q N Q V H G T H V I K L G S L K A N D D A A R E A L G A W   PpHIS6
39  H P S S Y Y A K L Y K D R D V Q G C H V I K L G P - - N N D D A A R E A L Q E S   ScHIS6

81  R G G L Q I G G G I T D S N A Q E W I D Q G A S H V I V T S W L F P - E G Q F S   PpHIS6
77  P Q F L Q V G G G I N D T N C L E W L K W - A S K V I V T S W L F T K E G H F Q   ScHIS6

120 I E R L Q H L S S L I G K E K L V V D L S C R R Q E I D G S P Q W V V A M N K W   PpHIS6
116 L K R L E R L T E L C G K D R I V V D L S C R K T Q D G - - - R W I V A M N K W   ScHIS6

160 Q T L T S S V L D R E F F Q L L S Q Y C D E F L V H A A D V E G L C Q G I D Q E   PpHIS6
153 Q T L T D L E L N A D T F R E L R K Y T N E F L I H A A D V E G L C G G I D E L   ScHIS6

200 L V R K L S E W S - - - - D L P V T Y A G G A R S I Q D L E T V K H L S N G K V   PpHIS6
193 L V S K L F E W T K D Y D D L K I V Y A G G A K S V D D L K L V D E L S H G K V   ScHIS6

236 D L T F G S A L N I F G G N L V K F E D C V K W N K T Q                         PpHIS6
233 D L T F G S S L D I F G G N L V K F E D C C R W N E K Q G                       ScHIS6
```

FIG 8
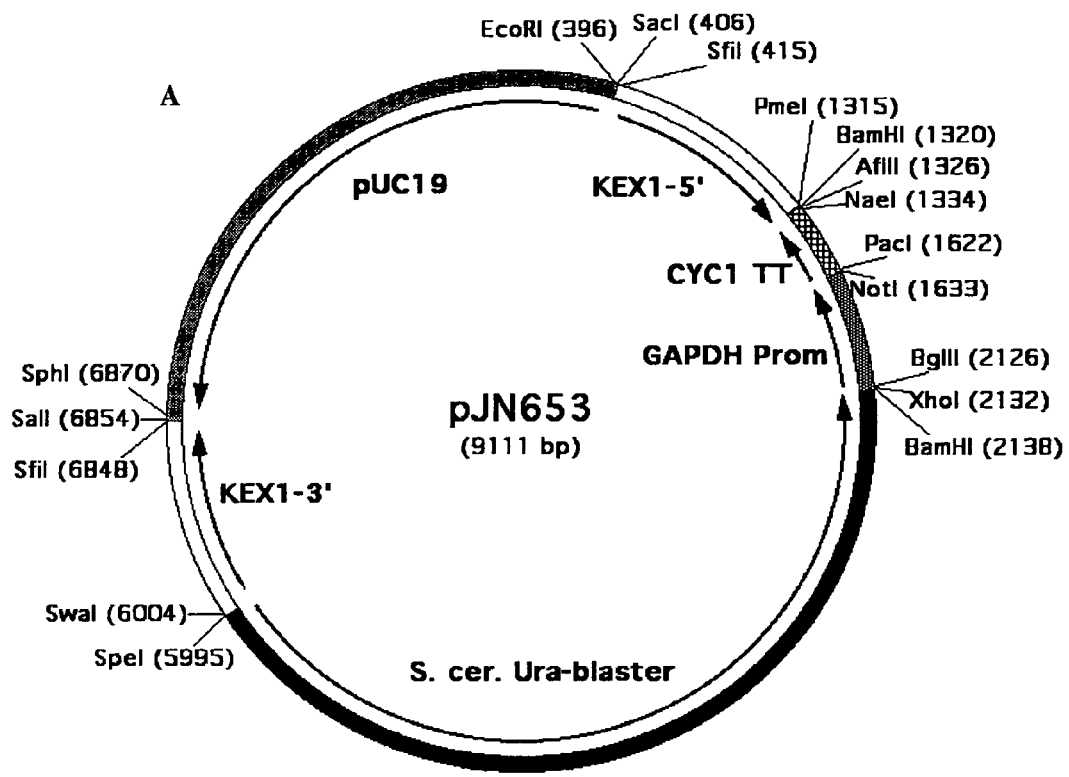
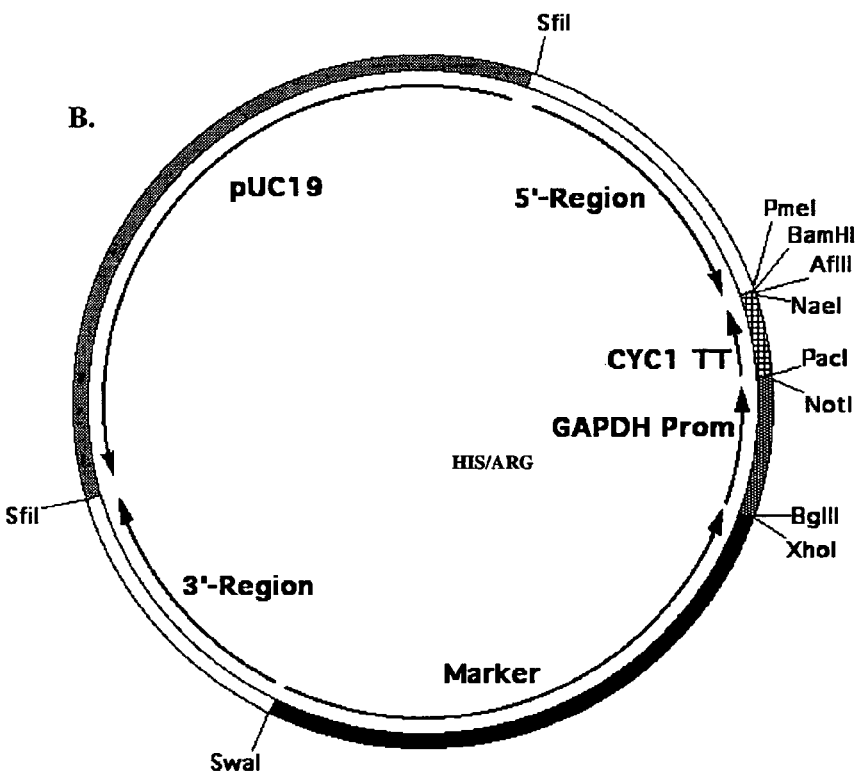

SEQUENCE LISTING

<160> NUMBER OF SEQ ID NOS: 81

<210> SEQ ID NO 1
<211> LENGTH: 1854
<212> TYPE: DNA
<213> ORGANISM: Pichia pastoris
<220> FEATURE:
<221> NAME/KEY: CDS
<222> LOCATION: (385)..(1629)

<400> SEQUENCE: 1

```
cagttgagcc agaccgcgct aaacgcatac caattgccaa atcaggcaat tgtgagacag      60
tggtaaaaaa gatgcctgca aagttagatt cacacagtaa gagagatcct actcataaat     120
gaggcgctta tttagtagct agtgatagcc actgcggttc tgctttatgc tatttgttgt     180
atgccttact atctttgttt ggctcctttt tcttgacgtt ttccgttgga gggactccct     240
attctgagtc atgagccgca cagattatcg cccaaaattg acaaaatctt ctggcgaaaa     300
aagtataaaa ggagaaaaaa gctcacccct ttccagcgta gaaagtatat atcagtcatt     360
gaagactatt atttaaataa caca atg tct aaa gga aaa gtt tgt ttg gcc        411
                            Met Ser Lys Gly Lys Val Cys Leu Ala
                              1               5 tac tcc ggt ggt ttg gat acc tcc atc atc cta gct tgg ttg ttg gag       459
Tyr Ser Gly Gly Leu Asp Thr Ser Ile Ile Leu Ala Trp Leu Leu Glu
 10                  15                  20                  25 cag gga tac gaa gtc gtt gcc ttt tta gcc aac att ggt caa gag gaa       507
Gln Gly Tyr Glu Val Val Ala Phe Leu Ala Asn Ile Gly Gln Glu Glu
                30                  35                  40 gac ttt gag gct gct aga gag aaa gct ctg aag atc ggt gct acc aag       555
Asp Phe Glu Ala Ala Arg Glu Lys Ala Leu Lys Ile Gly Ala Thr Lys
             45                  50                  55 ttt atc gtc agt gac gtt agg aag gaa ttt gtt gag gaa gtt ttg ttc       603
Phe Ile Val Ser Asp Val Arg Lys Glu Phe Val Glu Glu Val Leu Phe
         60                  65                  70 cca gca gtc caa gtt aac gct atc tac gag aac gtc tac tta ctg ggt       651
Pro Ala Val Gln Val Asn Ala Ile Tyr Glu Asn Val Tyr Leu Leu Gly
     75                  80                  85 acc tct ttg gcc aga cca gtc att gcc aag gcc caa ata gag gtt gct       699
Thr Ser Leu Ala Arg Pro Val Ile Ala Lys Ala Gln Ile Glu Val Ala
 90                  95                 100                 105 gaa caa gaa ggt tgt ttt gct gtt gcc cac ggt tgt acc gga aag ggt       747
Glu Gln Glu Gly Cys Phe Ala Val Ala His Gly Cys Thr Gly Lys Gly
```

```
                   110                115                120
aac gat cag gtt aga ttt gag ctt tcc ttt tat gct ctg aag cct gac    795
Asn Asp Gln Val Arg Phe Glu Leu Ser Phe Tyr Ala Leu Lys Pro Asp
            125                 130                 135 gtt gtc tgt atc gcc cca tgg aga gac cca gaa ttc ttc gaa aga ttc    843
Val Val Cys Ile Ala Pro Trp Arg Asp Pro Glu Phe Phe Glu Arg Phe
        140                 145                 150 gct ggt aga aat gac ttg ctg aat tac gct gct gag aag gat att cca    891
Ala Gly Arg Asn Asp Leu Leu Asn Tyr Ala Ala Glu Lys Asp Ile Pro
    155                 160                 165 gtt gct cag act aaa gcc aag cca tgg tct act gat gag aac atg gct    939
Val Ala Gln Thr Lys Ala Lys Pro Trp Ser Thr Asp Glu Asn Met Ala
170                 175                 180                 185 cac atc tcc ttc gag gct ggt att cta gaa gat cca aac act act cct    987
His Ile Ser Phe Glu Ala Gly Ile Leu Glu Asp Pro Asn Thr Thr Pro
                190                 195                 200 cca aag gac atg tgg aag ctc act gtt gac cca gaa gat gca cca gac   1035
Pro Lys Asp Met Trp Lys Leu Thr Val Asp Pro Glu Asp Ala Pro Asp
            205                 210                 215 aag cca gag ttc ttt gac gtc cac ttt gag aag ggt aag cca gtt aaa   1083
Lys Pro Glu Phe Phe Asp Val His Phe Glu Lys Gly Lys Pro Val Lys
        220                 225                 230 tta gtt ctc gag aac aaa act gag gtc acc gat ccg gtt gag atc ttt   1131
Leu Val Leu Glu Asn Lys Thr Glu Val Thr Asp Pro Val Glu Ile Phe
    235                 240                 245 ttg act gct aac gcc att gct aga aga aac ggt gtt ggt aga att gac   1179
Leu Thr Ala Asn Ala Ile Ala Arg Arg Asn Gly Val Gly Arg Ile Asp
250                 255                 260                 265 att gtc gag aac aga ttc atc gga atc aag tcc aga ggt tgt tat gaa   1227
Ile Val Glu Asn Arg Phe Ile Gly Ile Lys Ser Arg Gly Cys Tyr Glu
                270                 275                 280 act cca ggt ttg act cta ctg aga acc act cac atc gac ttg gaa ggt   1275
Thr Pro Gly Leu Thr Leu Leu Arg Thr Thr His Ile Asp Leu Glu Gly
            285                 290                 295 ctt acc gtt gac cgt gaa gtt aga tcg atc aga gac act ttt gtt acc   1323
Leu Thr Val Asp Arg Glu Val Arg Ser Ile Arg Asp Thr Phe Val Thr
        300                 305                 310 cca acc tac tct aag ttg tta tac aac ggg ttg tac ttt acc cca gaa   1371
Pro Thr Tyr Ser Lys Leu Leu Tyr Asn Gly Leu Tyr Phe Thr Pro Glu
    315                 320                 325 ggt gag tac gtc aga act atg att cag cct tct caa aac acc gtc aac   1419
Gly Glu Tyr Val Arg Thr Met Ile Gln Pro Ser Gln Asn Thr Val Asn
330                 335                 340                 345 ggt gtt gtt aga gcc aag gcc tac aaa ggt aat gtg tat aac cta gga   1467
Gly Val Val Arg Ala Lys Ala Tyr Lys Gly Asn Val Tyr Asn Leu Gly
                350                 355                 360 aga tac tct gaa acc gag aaa ttg tac gat gct acc gaa tct tcc atg   1515
Arg Tyr Ser Glu Thr Glu Lys Leu Tyr Asp Ala Thr Glu Ser Ser Met
            365                 370                 375 gat gag ttg acc gga ttc cac cct caa gaa gct gga gga ttt atc aca   1563
Asp Glu Leu Thr Gly Phe His Pro Gln Glu Ala Gly Gly Phe Ile Thr
        380                 385                 390 aca caa gcc atc aga atc aag aag tac gga gaa agt gtc aga gag aag   1611
Thr Gln Ala Ile Arg Ile Lys Lys Tyr Gly Glu Ser Val Arg Glu Lys
    395                 400                 405 gga aag ttt ttg gga ctt taactcaagt aaaaggatag ttgtacaatt         1659
Gly Lys Phe Leu Gly Leu
410                 415 atatatacga agaataaatc attacaaaaa gtattcgttt ctttgattct taacaggatt 1719
```

-continued

```
cattttctgg gtgtcatcag gtacagcgct gaatatcttg aagttaacat cgagctcatc    1779
atcgacgttc atcacactag ccacgtttcc gcaacggtag caataattag gagcggacca    1839
cacagtgacg acatc                                                     1854
```

<210> SEQ ID NO 2
<211> LENGTH: 415
<212> TYPE: PRT
<213> ORGANISM: Pichia pastoris

<400> SEQUENCE: 2

```
Met Ser Lys Gly Lys Val Cys Leu Ala Tyr Ser Gly Gly Leu Asp Thr
 1               5                  10                  15

Ser Ile Ile Leu Ala Trp Leu Leu Glu Gln Gly Tyr Glu Val Val Ala
             20                  25                  30

Phe Leu Ala Asn Ile Gly Gln Glu Asp Phe Glu Ala Ala Arg Glu
         35                  40                  45

Lys Ala Leu Lys Ile Gly Ala Thr Lys Phe Ile Val Ser Asp Val Arg
     50                  55                  60

Lys Glu Phe Val Glu Val Leu Phe Pro Ala Val Gln Val Asn Ala
 65                  70                  75                  80

Ile Tyr Glu Asn Val Tyr Leu Leu Gly Thr Ser Leu Ala Arg Pro Val
                 85                  90                  95

Ile Ala Lys Ala Gln Ile Glu Val Ala Glu Gln Gly Cys Phe Ala
            100                 105                 110

Val Ala His Gly Cys Thr Gly Lys Gly Asn Asp Gln Val Arg Phe Glu
        115                 120                 125

Leu Ser Phe Tyr Ala Leu Lys Pro Asp Val Val Cys Ile Ala Pro Trp
    130                 135                 140

Arg Asp Pro Glu Phe Phe Glu Arg Phe Ala Gly Arg Asn Asp Leu Leu
145                 150                 155                 160

Asn Tyr Ala Ala Glu Lys Asp Ile Pro Val Ala Gln Thr Lys Ala Lys
                165                 170                 175

Pro Trp Ser Thr Asp Glu Asn Met Ala His Ile Ser Phe Glu Ala Gly
            180                 185                 190

Ile Leu Glu Asp Pro Asn Thr Thr Pro Pro Lys Asp Met Trp Lys Leu
        195                 200                 205

Thr Val Asp Pro Glu Asp Ala Pro Asp Lys Pro Glu Phe Phe Asp Val
    210                 215                 220

His Phe Glu Lys Gly Lys Pro Val Lys Leu Val Leu Glu Asn Lys Thr
225                 230                 235                 240

Glu Val Thr Asp Pro Val Glu Ile Phe Leu Thr Ala Asn Ala Ile Ala
                245                 250                 255

Arg Arg Asn Gly Val Gly Arg Ile Asp Ile Val Glu Asn Arg Phe Ile
            260                 265                 270

Gly Ile Lys Ser Arg Gly Cys Tyr Glu Thr Pro Gly Leu Thr Leu Leu
        275                 280                 285

Arg Thr Thr His Ile Asp Leu Glu Gly Leu Thr Val Asp Arg Glu Val
    290                 295                 300

Arg Ser Ile Arg Asp Thr Phe Val Thr Pro Thr Tyr Ser Lys Leu Leu
305                 310                 315                 320

Tyr Asn Gly Leu Tyr Phe Thr Pro Glu Gly Glu Tyr Val Arg Thr Met
                325                 330                 335

Ile Gln Pro Ser Gln Asn Thr Val Asn Gly Val Val Arg Ala Lys Ala
```

-continued

```
                    340                 345                 350
Tyr Lys Gly Asn Val Tyr Asn Leu Gly Arg Tyr Ser Glu Thr Glu Lys
            355                 360                 365

Leu Tyr Asp Ala Thr Glu Ser Ser Met Asp Glu Leu Thr Gly Phe His
        370                 375                 380

Pro Gln Glu Ala Gly Gly Phe Ile Thr Thr Gln Ala Ile Arg Ile Lys
385                 390                 395                 400

Lys Tyr Gly Glu Ser Val Arg Glu Lys Gly Lys Phe Leu Gly Leu
                405                 410                 415

<210> SEQ ID NO 3
<211> LENGTH: 420
<212> TYPE: PRT
<213> ORGANISM: Saccharomyces cerevisiae

<400> SEQUENCE: 3

Met Ser Lys Gly Lys Val Cys Leu Ala Tyr Ser Gly Gly Leu Asp Thr
1               5                   10                  15

Ser Val Ile Leu Ala Trp Leu Leu Asp Gln Gly Tyr Glu Val Val Ala
            20                  25                  30

Phe Met Ala Asn Val Gly Gln Glu Glu Asp Phe Asp Ala Ala Lys Glu
        35                  40                  45

Lys Ala Leu Lys Ile Gly Ala Cys Lys Phe Val Cys Val Asp Cys Arg
    50                  55                  60

Glu Asp Phe Val Lys Asp Ile Leu Phe Pro Ala Val Gln Val Asn Ala
65                  70                  75                  80

Val Tyr Glu Asp Val Tyr Leu Leu Gly Thr Ser Leu Ala Arg Pro Val
                85                  90                  95

Ile Ala Lys Ala Gln Ile Asp Val Ala Lys Gln Glu Gly Cys Phe Ala
            100                 105                 110

Val Ser His Gly Cys Thr Gly Lys Gly Asn Asp Gln Ile Arg Phe Glu
        115                 120                 125

Leu Ser Phe Tyr Ala Leu Lys Pro Asp Val Lys Cys Ile Thr Pro Trp
    130                 135                 140

Arg Met Pro Glu Phe Phe Glu Arg Phe Ala Gly Arg Lys Asp Leu Leu
145                 150                 155                 160

Asp Tyr Ala Ala Gln Lys Gly Ile Pro Val Ala Gln Thr Lys Ala Lys
                165                 170                 175

Pro Trp Ser Thr Asp Glu Asn Gln Ala His Ile Ser Tyr Glu Ala Gly
            180                 185                 190

Ile Leu Glu Asp Pro Asp Thr Thr Pro Pro Lys Asp Met Trp Lys Leu
        195                 200                 205

Ile Val Asp Pro Met Asp Ala Pro Asp Gln Pro Gln Asp Leu Thr Ile
    210                 215                 220

Asp Phe Glu Arg Gly Leu Pro Val Lys Leu Thr Tyr Thr Asp Asn Lys
225                 230                 235                 240

Thr Ser Lys Glu Val Ser Val Thr Lys Pro Leu Asp Val Phe Leu Ala
                245                 250                 255

Ala Ser Asn Leu Ala Arg Ala Asn Gly Val Gly Arg Ile Asp Ile Val
            260                 265                 270

Glu Asp Arg Tyr Ile Asn Leu Lys Ser Arg Gly Cys Tyr Glu Gln Ala
        275                 280                 285

Pro Leu Thr Val Leu Arg Lys Ala His Val Asp Leu Glu Gly Leu Thr
    290                 295                 300
```

-continued

```
Leu Asp Lys Glu Val Arg Gln Leu Arg Asp Ser Phe Val Thr Pro Asn
305                 310                 315                 320

Tyr Ser Arg Leu Ile Tyr Asn Gly Phe Leu Leu His Pro Glu Cys Glu
                325                 330                 335

Tyr Ile Arg Ser Met Ile Gln Pro Ser Gln Asn Ser Val Asn Gly Thr
            340                 345                 350

Val Arg Val Arg Leu Tyr Lys Gly Asn Val Ile Ile Leu Gly Arg Ser
        355                 360                 365

Thr Lys Thr Glu Lys Leu Tyr Asp Pro Thr Glu Ser Ser Met Asp Glu
    370                 375                 380

Leu Thr Gly Phe Leu Pro Thr Asp Thr Thr Gly Phe Ile Ala Ile Gln
385                 390                 395                 400

Ala Ile Arg Ile Lys Lys Tyr Gly Glu Ser Lys Lys Thr Lys Gly Glu
                405                 410                 415

Glu Leu Thr Leu
            420
```

<210> SEQ ID NO 4
<211> LENGTH: 2477
<212> TYPE: DNA
<213> ORGANISM: Pichia pastoris
<220> FEATURE:
<221> NAME/KEY: CDS
<222> LOCATION: (336)..(2105)

<400> SEQUENCE: 4

```
gtgagcgatg aggagggccc actgagttat gatatatgat atatatttag aaacggttcg      60
cacagaatag tggccagcaa acatcattt ttcggtggag ttttgactgg tttatgaagc      120
ccttaattgt gaaaaggtgt aagaaagtgt gcatctcgaa tttactccat agtccattag     180
cctccacctt cccttaacc gtgtatttgt gaatggtgtt cactatgttt cctagggcat      240
taccatcctg tcgccgtcag tcaggccgta tgttcataag cgtaagtaat tgaaaccttt     300
tgacaccgca gcgatctccc actaaccagt agtcc atg ttg agt atc aaa gat       353
                                        Met Leu Ser Ile Lys Asp
                                          1               5 ttc acc tca aat ctc aca aga cat gct aga aac acc gag gag aaa agg      401
Phe Thr Ser Asn Leu Thr Arg His Ala Arg Asn Thr Glu Glu Lys Arg
        10                  15                  20 aac atg gtt cta act atc ctc aac tcc act gct acc aag aga gaa gtt      449
Asn Met Val Leu Thr Ile Leu Asn Ser Thr Ala Thr Lys Arg Glu Val
    25                  30                  35 cga aac tac ttg aag aag tat cct cta tta aag gat gtg gat atc tac      497
Arg Asn Tyr Leu Lys Lys Tyr Pro Leu Leu Lys Asp Val Asp Ile Tyr
40                  45                  50 agt aag ggc caa atg gat cgg agc tcc gtt agc aaa cgt aac aag tac      545
Ser Lys Gly Gln Met Asp Arg Ser Ser Val Ser Lys Arg Asn Lys Tyr
 55                  60                  65                  70 tcc agc atg att gac aat ctc atg ttg aag cat tcg acc aat aat gaa      593
Ser Ser Met Ile Asp Asn Leu Met Leu Lys His Ser Thr Asn Asn Glu
                75                  80                  85 aac aac aaa att gaa gac ttt cac ttg aat cgc cca agg tct gat cta      641
Asn Asn Lys Ile Glu Asp Phe His Leu Asn Arg Pro Arg Ser Asp Leu
            90                  95                 100 atc agt aaa tct aag ctg gag atc aaa ctc act gac acc ctt cgt att      689
Ile Ser Lys Ser Lys Leu Glu Ile Lys Leu Thr Asp Thr Leu Arg Ile
        105                 110                 115 gct att gtg aag atc agg cag ttt agg gat att gac ccc aca gct ttg      737
Ala Ile Val Lys Ile Arg Gln Phe Arg Asp Ile Asp Pro Thr Ala Leu
```

-continued

```
                  120                     125                     130
aaa ggt atc gcc ttt act ttg tac aaa cta ata aaa ctt ggg gtg agt      785
Lys Gly Ile Ala Phe Thr Leu Tyr Lys Leu Ile Lys Leu Gly Val Ser
135                 140                 145                 150 ccc ata gtg tta ttg gat aca gat aaa gaa gtt cag gct ttg aat gga      833
Pro Ile Val Leu Leu Asp Thr Asp Lys Glu Val Gln Ala Leu Asn Gly
                155                 160                 165 gaa tcg gac gcc atg gta caa aaa agc att gcc aat tac cat cag cag      881
Glu Ser Asp Ala Met Val Gln Lys Ser Ile Ala Asn Tyr His Gln Gln
            170                 175                 180 gcc ctg agt ttc ata aat atc att gaa aaa tgt ttc cat aaa tat gag      929
Ala Leu Ser Phe Ile Asn Ile Ile Glu Lys Cys Phe His Lys Tyr Glu
        185                 190                 195 gat gac aac gag ctc tcc gca agg gcc atc aga ggt ttg ttc gaa caa      977
Asp Asp Asn Glu Leu Ser Ala Arg Ala Ile Arg Gly Leu Phe Glu Gln
    200                 205                 210 aaa ttt gat gaa gac aga ttt tca atg acc cta cca gag cta tta cta     1025
Lys Phe Asp Glu Asp Arg Phe Ser Met Thr Leu Pro Glu Leu Leu Leu
215                 220                 225                 230 att cct ata tct cag ggt ata gtc cct gtt gtt tat cct gtg gga tat     1073
Ile Pro Ile Ser Gln Gly Ile Val Pro Val Val Tyr Pro Val Gly Tyr
                235                 240                 245 atg gat aag ggc tcc aaa aat gta ttt cta tcc tcc gag gca gtc ctc     1121
Met Asp Lys Gly Ser Lys Asn Val Phe Leu Ser Ser Glu Ala Val Leu
            250                 255                 260 caa tgt tta gct act gac ttg aaa tcc ttg aat gat aga cat aga ttg     1169
Gln Cys Leu Ala Thr Asp Leu Lys Ser Leu Asn Asp Arg His Arg Leu
        265                 270                 275 gac cat gac aag gag aac tta ttc aca att gaa aag tac att ttc att     1217
Asp His Asp Lys Glu Asn Leu Phe Thr Ile Glu Lys Tyr Ile Phe Ile
    280                 285                 290 gac cca ttg gga ggt atc cca tct ttg gag agg tac aaa agt gca cat     1265
Asp Pro Leu Gly Gly Ile Pro Ser Leu Glu Arg Tyr Lys Ser Ala His
295                 300                 305                 310 gta tat atc aat cta tta caa gag tat gaa gac att gtg tcg gag ctt     1313
Val Tyr Ile Asn Leu Leu Gln Glu Tyr Glu Asp Ile Val Ser Glu Leu
                315                 320                 325 tac ata ggg ttc tta aag act gga gaa agg gac cag cat ttg aag aac     1361
Tyr Ile Gly Phe Leu Lys Thr Gly Glu Arg Asp Gln His Leu Lys Asn
            330                 335                 340 tta aac ttg ctt cag aaa ttg ttg cag gta acc aca gat gca tca gga     1409
Leu Asn Leu Leu Gln Lys Leu Leu Gln Val Thr Thr Asp Ala Ser Gly
        345                 350                 355 ata gtt act act cct caa atc gcc atg ttg aat cag acc gac cga ttc     1457
Ile Val Thr Thr Pro Gln Ile Ala Met Leu Asn Gln Thr Asp Arg Phe
    360                 365                 370 acc aat cca ata att tac aat gtc tta acc gat agg ccg aca ata tca     1505
Thr Asn Pro Ile Ile Tyr Asn Val Leu Thr Asp Arg Pro Thr Ile Ser
375                 380                 385                 390 tcg tca tta ccg gtt gat ttg aaa aag acc cct ttg cta aac act tca     1553
Ser Ser Leu Pro Val Asp Leu Lys Lys Thr Pro Leu Leu Asn Thr Ser
                395                 400                 405 atc att agg aga ggc gta ccg gtt gaa gtt tat gtg gac gaa tca tct     1601
Ile Ile Arg Arg Gly Val Pro Val Glu Val Tyr Val Asp Glu Ser Ser
            410                 415                 420 gac aaa agt ggg ctg tgc cta gac tct ctt ctg aaa cga gga gct tta     1649
Asp Lys Ser Gly Leu Cys Leu Asp Ser Leu Leu Lys Arg Gly Ala Leu
        425                 430                 435 gac tta gaa aag ctt aag aat gtg atc gat ttg tcg ttt cga aag gac     1697
```

```
Asp Leu Glu Lys Leu Lys Asn Val Ile Asp Leu Ser Phe Arg Lys Asp
    440                 445                 450 ttg aat atg aaa aag tac cta gcc aga gta aag aac aat gtt gca gct      1745
Leu Asn Met Lys Lys Tyr Leu Ala Arg Val Lys Asn Asn Val Ala Ala
455                 460                 465                 470 atc tta atc gct gga gat tac gaa ggc gtg atc ata gtt act tgg gag      1793
Ile Leu Ile Ala Gly Asp Tyr Glu Gly Val Ile Ile Val Thr Trp Glu
                475                 480                 485 gta acg gat gaa gaa aag ccg cag aaa ata gct tat tta gat aag ttt      1841
Val Thr Asp Glu Glu Lys Pro Gln Lys Ile Ala Tyr Leu Asp Lys Phe
            490                 495                 500 gca gtg tct cct aag gcc caa gga tcg aca ggg gtt gcc gat gtt ctt      1889
Ala Val Ser Pro Lys Ala Gln Gly Ser Thr Gly Val Ala Asp Val Leu
        505                 510                 515 ttc aag tca tta ttg tcc aat ttt gag aac gaa ttg ttc tgg aga tct      1937
Phe Lys Ser Leu Leu Ser Asn Phe Glu Asn Glu Leu Phe Trp Arg Ser
    520                 525                 530 cga tct aat aat cca gtg aac aaa tgg tac ttt gaa cgg agc aaa ggt      1985
Arg Ser Asn Asn Pro Val Asn Lys Trp Tyr Phe Glu Arg Ser Lys Gly
535                 540                 545                 550 tct ctt act gtt act ggc aca aat tgg aaa tgc ttc tac acc ggc aag      2033
Ser Leu Thr Val Thr Gly Thr Asn Trp Lys Cys Phe Tyr Thr Gly Lys
                555                 560                 565 aac tat cct tca ttg gat aga atg aag ggc tat ttc aac atc tgt gag      2081
Asn Tyr Pro Ser Leu Asp Arg Met Lys Gly Tyr Phe Asn Ile Cys Glu
            570                 575                 580 aga atc caa cct tcc tgg aat gga taaagacgag atcaattaga acctgttttg     2135
Arg Ile Gln Pro Ser Trp Asn Gly
        585                 590 gcaataaccg aggattagga acaaagtccg ggtaattatg cgactctctc tttttcatat    2195
gcaggtcgag caagaatctt gttttcgtg gtgggactgg gcagcaatta acaaccaatc     2255
ggcacttgca ataagtcgat tagcgcatgg tgggggacag tagatagctg ctgaaatttt    2315
tgggtgcgga caatttcaag agtctgaggc cctgctctca ctagcagtca gaatcatctg    2375
cctcacatac agtctcctga tgctgctact tacttggcaa gcgatgatgt ttacacaatt    2435
gcagcttttt agttgctgtc atggctctag aattccttgg cc                      2477

<210> SEQ ID NO 5
<211> LENGTH: 590
<212> TYPE: PRT
<213> ORGANISM: Pichia pastoris

<400> SEQUENCE: 5

Met Leu Ser Ile Lys Asp Phe Thr Ser Asn Leu Thr Arg His Ala Arg
  1               5                  10                  15

Asn Thr Glu Glu Lys Arg Asn Met Val Leu Thr Ile Leu Asn Ser Thr
                 20                  25                  30

Ala Thr Lys Arg Glu Val Arg Asn Tyr Leu Lys Lys Tyr Pro Leu Leu
             35                  40                  45

Lys Asp Val Asp Ile Tyr Ser Lys Gly Gln Met Asp Arg Ser Ser Val
         50                  55                  60

Ser Lys Arg Asn Lys Tyr Ser Ser Met Ile Asp Asn Leu Met Leu Lys
 65                  70                  75                  80

His Ser Thr Asn Asn Glu Asn Asn Lys Ile Glu Asp Phe His Leu Asn
                 85                  90                  95

Arg Pro Arg Ser Asp Leu Ile Ser Lys Ser Lys Leu Glu Ile Lys Leu
            100                 105                 110
```

-continued

```
Thr Asp Thr Leu Arg Ile Ala Ile Val Lys Ile Arg Gln Phe Arg Asp
        115                 120                 125
Ile Asp Pro Thr Ala Leu Lys Gly Ile Ala Phe Thr Leu Tyr Lys Leu
    130                 135                 140
Ile Lys Leu Gly Val Ser Pro Ile Val Leu Leu Asp Thr Asp Lys Glu
145                 150                 155                 160
Val Gln Ala Leu Asn Gly Glu Ser Asp Ala Met Val Gln Lys Ser Ile
                165                 170                 175
Ala Asn Tyr His Gln Gln Ala Leu Ser Phe Ile Asn Ile Ile Glu Lys
                180                 185                 190
Cys Phe His Lys Tyr Glu Asp Asp Asn Glu Leu Ser Ala Arg Ala Ile
            195                 200                 205
Arg Gly Leu Phe Glu Gln Lys Phe Asp Glu Asp Arg Phe Ser Met Thr
        210                 215                 220
Leu Pro Glu Leu Leu Leu Ile Pro Ile Ser Gln Gly Ile Val Pro Val
225                 230                 235                 240
Val Tyr Pro Val Gly Tyr Met Asp Lys Gly Ser Lys Asn Val Phe Leu
                245                 250                 255
Ser Ser Glu Ala Val Leu Gln Cys Leu Ala Thr Asp Leu Lys Ser Leu
                260                 265                 270
Asn Asp Arg His Arg Leu Asp His Asp Lys Glu Asn Leu Phe Thr Ile
            275                 280                 285
Glu Lys Tyr Ile Phe Ile Asp Pro Leu Gly Gly Ile Pro Ser Leu Glu
        290                 295                 300
Arg Tyr Lys Ser Ala His Val Tyr Ile Asn Leu Leu Gln Glu Tyr Glu
305                 310                 315                 320
Asp Ile Val Ser Glu Leu Tyr Ile Gly Phe Leu Lys Thr Gly Glu Arg
                325                 330                 335
Asp Gln His Leu Lys Asn Leu Asn Leu Leu Gln Lys Leu Leu Gln Val
                340                 345                 350
Thr Thr Asp Ala Ser Gly Ile Val Thr Thr Pro Gln Ile Ala Met Leu
            355                 360                 365
Asn Gln Thr Asp Arg Phe Thr Asn Pro Ile Ile Tyr Asn Val Leu Thr
        370                 375                 380
Asp Arg Pro Thr Ile Ser Ser Leu Pro Val Asp Leu Lys Lys Thr
385                 390                 395                 400
Pro Leu Leu Asn Thr Ser Ile Ile Arg Arg Gly Val Pro Val Glu Val
                405                 410                 415
Tyr Val Asp Glu Ser Ser Asp Lys Ser Gly Leu Cys Leu Asp Ser Leu
                420                 425                 430
Leu Lys Arg Gly Ala Leu Asp Leu Glu Lys Leu Lys Asn Val Ile Asp
            435                 440                 445
Leu Ser Phe Arg Lys Asp Leu Asn Met Lys Lys Tyr Leu Ala Arg Val
        450                 455                 460
Lys Asn Asn Val Ala Ala Ile Leu Ile Ala Gly Asp Tyr Glu Gly Val
465                 470                 475                 480
Ile Ile Val Thr Trp Glu Val Thr Asp Glu Glu Lys Pro Gln Lys Ile
                485                 490                 495
Ala Tyr Leu Asp Lys Phe Ala Val Ser Pro Lys Ala Gln Gly Ser Thr
                500                 505                 510
Gly Val Ala Asp Val Leu Phe Lys Ser Leu Leu Ser Asn Phe Glu Asn
            515                 520                 525
```

```
Glu Leu Phe Trp Arg Ser Arg Ser Asn Asn Pro Val Asn Lys Trp Tyr
    530                 535                 540

Phe Glu Arg Ser Lys Gly Ser Leu Thr Val Thr Gly Thr Asn Trp Lys
545                 550                 555                 560

Cys Phe Tyr Thr Gly Lys Asn Tyr Pro Ser Leu Asp Arg Met Lys Gly
                565                 570                 575

Tyr Phe Asn Ile Cys Glu Arg Ile Gln Pro Ser Trp Asn Gly
            580                 585                 590

<210> SEQ ID NO 6
<211> LENGTH: 574
<212> TYPE: PRT
<213> ORGANISM: Saccharomyces cerevisiae

<400> SEQUENCE: 6

Met Trp Arg Arg Ile Phe Ala His Glu Leu Lys Tyr Asp Gln Pro Asn
1               5                   10                  15

Ala Ser Ser Lys Asn Leu Ile Leu Ser Val Leu Asn Thr Thr Ala Thr
                20                  25                  30

Lys Arg Glu Ala Lys Asp Tyr Leu Ser Lys Tyr Thr Asn Asp Ser Gly
            35                  40                  45

Gln His Asn His Cys Leu Phe Phe Ile Arg Asp Leu His Lys Val Ala
        50                  55                  60

Pro Ala Ile Leu Ser Gln Phe Ser Val Ile Lys Arg Leu Gly Met
65                  70                  75                  80

Leu Gly Leu Arg Pro Met Phe Val Ile Pro Pro Ser Pro Thr His Val
                85                  90                  95

Asn Ile Gln Ala Glu Leu Leu Asp Ser Ile Val Thr Glu Ala Asp Leu
            100                 105                 110

Lys Pro Leu His Leu Lys Glu Gly Leu Thr Lys Ser Arg Thr Gly Leu
        115                 120                 125

Tyr His Ser Val Phe Ser Gln Glu Ser Arg Phe Phe Asp Ile Gly Asn
    130                 135                 140

Ser Asn Phe Ile Pro Ile Val Lys Pro Tyr Val Tyr Asn Glu Glu Thr
145                 150                 155                 160

Ala Ser Glu Phe Met Thr Lys Asp Val Val Lys Phe Met Asp Cys Leu
                165                 170                 175

Cys Gln Gly Asn Ile Pro His Ile Asp Lys Phe Phe Ile Leu Asn Asn
            180                 185                 190

Ala Gly Gly Ile Pro Ser Gly Glu Arg Asn Asp Asn Ala His Val Phe
        195                 200                 205

Ile Asn Leu Ser Gln Glu Leu Glu His Leu Ser Ser Ser Leu Ser His
    210                 215                 220

Asn Ile Ser Thr Leu Thr Lys Arg Glu Pro Arg Ser Gln Asn Leu Leu
225                 230                 235                 240

His Arg Met Glu Val Tyr Val Lys Lys Asp Glu Ile Ser Ser Leu Glu
                245                 250                 255

Cys Glu Tyr His Asp His Leu Glu Asn Leu Leu Leu Met Asp Lys Val
            260                 265                 270

Leu Ser Asn Leu Ala Ala Thr Ala Thr Gly Leu Ile Thr Thr Val Lys
        275                 280                 285

Ala Ala Ala Leu Ser Ser Asp Arg Lys Asn Pro Leu Val Tyr Asn Leu
    290                 295                 300

Leu Thr Asp Arg Ser Leu Ile Ser Ser Ser Leu Pro Arg Phe Lys Lys
305                 310                 315                 320
```

| | | | | | | | | | | | |
|---|---|---|---|---|---|---|---|---|---|---|---|
|Lys|Asp|Gly|Glu|Ile|Asp|Ser|Pro|Ala|Asn|Met|Phe|Asp|His|Ala|
| | | |325| | |330| | | |335| |

Lys Asp Gly Glu Ile Asp Ser Pro Ala Asn Met Phe Asp His Ala
             325          330          335

Trp Tyr Glu Leu Pro Ser Gln Gln Val Asn Ala Ala Pro Ser Asn Ser
         340            345           350

Asp Ala Val Leu Val Thr Thr Val Leu Lys Lys Gly Val His Ile Lys
       355            360           365

Thr Tyr Asp Tyr Lys Thr Leu Thr Gln Phe Asn Ser Ile Gly Leu Pro
    370           375           380

Lys Lys Phe His Val Pro Glu Lys Gly Ala Lys Pro Ser Ser Asn Ser
385             390           395          400

Pro Lys Leu Asp Ile Asn Lys Phe Lys Ser Ile Ile Asp Gln Ser Phe
         405            410           415

Lys Arg Ser Leu Asp Leu His Asp Tyr Ile Lys Arg Ile Asn Gly Lys
       420            425           430

Ile Ala Thr Ile Ile Val Ile Gly Asp Tyr Glu Gly Ile Ala Ile Leu
         435            440           445

Thr Tyr Glu Gly Ser Glu Glu Asn Ser Phe Val Tyr Leu Asp Lys Phe
    450           455           460

Ala Val Leu Pro His Leu Lys Gly Ser Leu Gly Ile Ser Asp Ile Ile
465             470           475          480

Phe Asn Leu Met Phe Lys Lys Phe Pro Asn Glu Ile Leu Trp Arg Ser
         485            490           495

Arg Lys Asp Asn Val Val Asn Lys Trp Tyr Phe Gln Arg Ser Val Ala
       500            505           510

Val Leu Asp Leu Ser Ile Asp Leu Asp Pro Glu His Cys Asp Glu Lys
         515            520           525

Gln Ser Gln Phe Lys Leu Phe Tyr Tyr Gly Asn Pro Gln Tyr Ala Lys
    530           535           540

Arg Ala Leu Arg Asp Lys Lys Arg Leu Arg Glu Phe Met Arg Ser Val
545             550           555          560

Arg Asp Ile Lys Pro Ser Trp Glu Asn Glu Lys Asn Ile Ser
       565            570

<210> SEQ ID NO 7
<211> LENGTH: 1870
<212> TYPE: DNA
<213> ORGANISM: Pichia pastoris
<220> FEATURE:
<221> NAME/KEY: CDS
<222> LOCATION: (530)..(1555)

<400> SEQUENCE: 7

| | |
|---|---|
|gggtgttatt ttcaagtaag agtcatttga ggtaagcacc aaaccgagta gtgaatgagc | 60 |
|aaagaatttt atgcttatgt aattgtttta tttgttccat tcgaacgtta taaactgtga | 120 |
|ttaaaacggg tatatttcaa ttccacgcgg aagcgtagtc agaatacaaa cccacaatta | 180 |
|agatggacag cttggccgct aacagtaaca aaaactaccg ccagttttc cttttgtctt | 240 |
|tcaagccatc ttccaatcat taatcagtgt caagttcgcc ttgaaagaca aaaaaaacac | 300 |
|agaaagtcct aaaagtgtga gcaatgatct aaagatttgg cttcatgata gattacttta | 360 |
|gagtagctgg caatgaattg ggatctgaac ttttgtcgtc tttctttccc ttaatttagt | 420 |
|atccagctgc aagtgactga aaaaggaaat ttttccaccg cggaaaacta acgatgcttg | 480 |
|gatgagtaaa aagtgaacaa ttactcaaat acttctcctc aactgaaaa atg agc atg    538<br>                                                                          Met Ser Met<br>                                                                           1 |

-continued

| | | |
|---|---|---|
| ttt aag atc cct aag tta gtg tta tct caa gga ttt cca agc cta aat<br>Phe Lys Ile Pro Lys Leu Val Leu Ser Gln Gly Phe Pro Ser Leu Asn<br>5                             10                        15 | 586 |
| aga aaa cta gct cag act acc aaa cct cca agg tcc tta atc tcc atc<br>Arg Lys Leu Ala Gln Thr Thr Lys Pro Pro Arg Ser Leu Ile Ser Ile<br>20                       25                        30                       35 | 634 |
| ttg gaa cta agt aac caa gaa cta agt tca ttg gtt gaa aga gca gca<br>Leu Glu Leu Ser Asn Gln Glu Leu Ser Ser Leu Val Glu Arg Ala Ala<br>                40                       45                       50 | 682 |
| tac cac aag aca caa tat aag tca ggc aaa atc tcc tct cag gta tca<br>Tyr His Lys Thr Gln Tyr Lys Ser Gly Lys Ile Ser Ser Gln Val Ser<br>             55                      60                     65 | 730 |
| ccg tcg ctg ttt gga aaa gtt gca gcc ctt ctt ttt aca aaa aga tcc<br>Pro Ser Leu Phe Gly Lys Val Ala Ala Leu Leu Phe Thr Lys Arg Ser<br>         70                    75                       80 | 778 |
| act aga aca aga ata tcc agc gag gga gca gca gtg tat ttc ggg gca<br>Thr Arg Thr Arg Ile Ser Ser Glu Gly Ala Ala Val Tyr Phe Gly Ala<br>          85                    90                       95 | 826 |
| cac ccc atg ttt cta ggt aag gat gat att cag ctt gga gtc aac gag<br>His Pro Met Phe Leu Gly Lys Asp Asp Ile Gln Leu Gly Val Asn Glu<br>100                     105                    110               115 | 874 |
| tcc ttc tat gac act acg aaa gtg atc tcc tct atg acg tct tgt atc<br>Ser Phe Tyr Asp Thr Thr Lys Val Ile Ser Ser Met Thr Ser Cys Ile<br>                120                    125                   130 | 922 |
| ttt gcc cgt gtt gat aaa cat tct caa atc caa gaa ctt gct caa cat<br>Phe Ala Arg Val Asp Lys His Ser Gln Ile Gln Glu Leu Ala Gln His<br>          135                    140                    145 | 970 |
| tcc aca gtg cct atc ata aat tct ttg tgt gat aga ttc cac cca ttg<br>Ser Thr Val Pro Ile Ile Asn Ser Leu Cys Asp Arg Phe His Pro Leu<br>                150                    155                   160 | 1018 |
| cag gct att aca gat att ctg acc att cgt gag gca ttc ggc ttc acc<br>Gln Ala Ile Thr Asp Ile Leu Thr Ile Arg Glu Ala Phe Gly Phe Thr<br>165                     170                    175 | 1066 |
| aaa ggt cta aag ttg gct tgg gta ggt gat tcc aac aat gtc atc aat<br>Lys Gly Leu Lys Leu Ala Trp Val Gly Asp Ser Asn Asn Val Ile Asn<br>180                     185                    190               195 | 1114 |
| gat ctt gca atc gca gcc att cgt tct gga att aac gtt tca att gcc<br>Asp Leu Ala Ile Ala Ala Ile Arg Ser Gly Ile Asn Val Ser Ile Ala<br>                200                    205                   210 | 1162 |
| att cct caa gga ata gaa atg gat gag gaa att att tcc aaa ggc caa<br>Ile Pro Gln Gly Ile Glu Met Asp Glu Glu Ile Ile Ser Lys Gly Gln<br>          215                    220                    225 | 1210 |
| cag att gca cag gaa aca gac act gtt ttg gaa gtt act cat gac cca<br>Gln Ile Ala Gln Glu Thr Asp Thr Val Leu Glu Val Thr His Asp Pro<br>                230                    235                   240 | 1258 |
| aag aag gct gtc aaa gat gcc aat gtc ctt gtc aca gac acc ttt gtc<br>Lys Lys Ala Val Lys Asp Ala Asn Val Leu Val Thr Asp Thr Phe Val<br>245                     250                    255 | 1306 |
| tct atg gga caa gaa gca gaa tcc aag gca aaa ttg gct caa ttt caa<br>Ser Met Gly Gln Glu Ala Glu Ser Lys Ala Lys Leu Ala Gln Phe Gln<br>260                     265                    270               275 | 1354 |
| ggt ttt caa atc tct agt gac ttg gct tca ggt gct gcc ccg gat tgg<br>Gly Phe Gln Ile Ser Ser Asp Leu Ala Ser Gly Ala Ala Pro Asp Trp<br>                280                    285                   290 | 1402 |
| aaa ttc atg cac tgc ttg ccg cgt cat aaa gag gaa gtg acc gac gaa<br>Lys Phe Met His Cys Leu Pro Arg His Lys Glu Glu Val Thr Asp Glu<br>          295                    300                    305 | 1450 |
| gtt ttc tac tct gac cgt tct ttg gtg ttc ccc gag gcc gag aac cga<br>Val Phe Tyr Ser Asp Arg Ser Leu Val Phe Pro Glu Ala Glu Asn Arg | 1498 |

-continued

```
                310                 315                 320
ttg tac gct gcc att gct gcc ctt gaa gga ttc gtt atc aac gaa ggt    1546
Leu Tyr Ala Ala Ile Ala Ala Leu Glu Gly Phe Val Ile Asn Glu Gly
    325                 330                 335 cgt ttg gta taaataaatt acacggattt atgcttgatc acatgaccaa            1595
Arg Leu Val
340 tcataactag gcggaccatg ctgcctcctg caaaggttct cgttcccaat ttcttaaagt  1655 cttatgtaat caacctgtat tttcttgctt gacgcgcccc aaagaaatca aaacaatccc  1715 cttcgaaaca ttgttaactt tgaattaact cctcaatagt tcctgaaaac agctttctct  1775 ggtcgcacgg tctggttccc ctttgcataa tcatctttga cttatgctag acaaaaatag  1835 aatcttgcga atccgcaaga agaaagatgg ctccg                             1870

<210> SEQ ID NO 8
<211> LENGTH: 342
<212> TYPE: PRT
<213> ORGANISM: Pichia pastoris

<400> SEQUENCE: 8

Met Ser Met Phe Lys Ile Pro Lys Leu Val Leu Ser Gln Gly Phe Pro
1               5                   10                  15

Ser Leu Asn Arg Lys Leu Ala Gln Thr Thr Lys Pro Pro Arg Ser Leu
            20                  25                  30

Ile Ser Ile Leu Glu Leu Ser Asn Gln Glu Leu Ser Ser Leu Val Glu
        35                  40                  45

Arg Ala Ala Tyr His Lys Thr Gln Tyr Lys Ser Gly Lys Ile Ser Ser
    50                  55                  60

Gln Val Ser Pro Ser Leu Phe Gly Lys Val Ala Leu Leu Phe Thr
65                  70                  75                  80

Lys Arg Ser Thr Arg Thr Arg Ile Ser Ser Glu Gly Ala Ala Val Tyr
                85                  90                  95

Phe Gly Ala His Pro Met Phe Leu Gly Lys Asp Asp Ile Gln Leu Gly
            100                 105                 110

Val Asn Glu Ser Phe Tyr Asp Thr Thr Lys Val Ile Ser Ser Met Thr
        115                 120                 125

Ser Cys Ile Phe Ala Arg Val Asp Lys His Ser Gln Ile Gln Glu Leu
    130                 135                 140

Ala Gln His Ser Thr Val Pro Ile Ile Asn Ser Leu Cys Asp Arg Phe
145                 150                 155                 160

His Pro Leu Gln Ala Ile Thr Asp Ile Leu Thr Ile Arg Glu Ala Phe
                165                 170                 175

Gly Phe Thr Lys Gly Leu Lys Leu Ala Trp Val Gly Asp Ser Asn Asn
            180                 185                 190

Val Ile Asn Asp Leu Ala Ile Ala Ala Ile Arg Ser Gly Ile Asn Val
        195                 200                 205

Ser Ile Ala Ile Pro Gln Gly Ile Glu Met Asp Glu Glu Ile Ile Ser
    210                 215                 220

Lys Gly Gln Gln Ile Ala Gln Glu Thr Asp Thr Val Leu Glu Val Thr
225                 230                 235                 240

His Asp Pro Lys Lys Ala Val Lys Asp Ala Asn Val Leu Val Thr Asp
                245                 250                 255

Thr Phe Val Ser Met Gly Gln Glu Ala Glu Ser Lys Ala Lys Leu Ala
            260                 265                 270
```

```
Gln Phe Gln Gly Phe Gln Ile Ser Ser Asp Leu Ala Ser Gly Ala Ala
        275                 280                 285

Pro Asp Trp Lys Phe Met His Cys Leu Pro Arg His Lys Glu Glu Val
        290                 295                 300

Thr Asp Glu Val Phe Tyr Ser Asp Arg Ser Leu Val Phe Pro Glu Ala
305                 310                 315                 320

Glu Asn Arg Leu Tyr Ala Ala Ile Ala Ala Leu Glu Gly Phe Val Ile
                325                 330                 335

Asn Glu Gly Arg Leu Val
            340

<210> SEQ ID NO 9
<211> LENGTH: 338
<212> TYPE: PRT
<213> ORGANISM: Saccharomyces cerevisiae

<400> SEQUENCE: 9

Met Ser Thr Thr Ala Ser Thr Pro Ser Ser Leu Arg His Leu Ile Ser
  1               5                  10                  15

Ile Lys Asp Leu Ser Asp Glu Glu Phe Arg Ile Leu Val Gln Arg Ala
             20                  25                  30

Gln His Phe Lys Asn Val Phe Lys Ala Asn Lys Thr Asn Asp Phe Gln
         35                  40                  45

Ser Asn His Leu Lys Leu Leu Gly Arg Thr Ile Ala Leu Ile Phe Thr
     50                  55                  60

Lys Arg Ser Thr Arg Thr Arg Ile Ser Thr Glu Gly Ala Ala Thr Phe
 65                  70                  75                  80

Phe Gly Ala Gln Pro Met Phe Leu Gly Lys Glu Asp Ile Gln Leu Gly
                 85                  90                  95

Val Asn Glu Ser Phe Tyr Asp Thr Thr Lys Val Val Ser Ser Met Val
            100                 105                 110

Ser Cys Ile Phe Ala Arg Val Asn Lys His Glu Asp Ile Leu Ala Phe
        115                 120                 125

Cys Lys Asp Ser Ser Val Pro Ile Ile Asn Ser Leu Cys Asp Lys Phe
    130                 135                 140

His Pro Leu Gln Ala Ile Cys Asp Leu Leu Thr Ile Ile Glu Asn Phe
145                 150                 155                 160

Asn Ile Ser Leu Asp Glu Val Asn Lys Gly Ile Asn Ser Lys Leu Lys
                165                 170                 175

Met Ala Trp Ile Gly Asp Ala Asn Asn Val Ile Asn Asp Met Cys Ile
            180                 185                 190

Ala Cys Leu Lys Phe Gly Ile Ser Val Ser Ile Ser Thr Pro Pro Gly
        195                 200                 205

Ile Glu Met Asp Ser Asp Ile Val Asp Glu Ala Lys Lys Val Ala Glu
    210                 215                 220

Arg Asn Gly Ala Thr Phe Glu Leu Thr His Asp Ser Leu Lys Ala Ser
225                 230                 235                 240

Thr Asn Ala Asn Ile Leu Val Thr Asp Thr Phe Val Ser Met Gly Glu
                245                 250                 255

Glu Phe Ala Lys Gln Ala Lys Leu Lys Gln Phe Lys Gly Phe Gln Ile
            260                 265                 270

Asn Gln Glu Leu Val Ser Val Ala Asp Pro Asn Tyr Lys Phe Met His
        275                 280                 285

Cys Leu Pro Arg His Gln Glu Glu Val Ser Asp Asp Val Phe Tyr Gly
    290                 295                 300
```

```
Glu His Ser Ile Val Phe Glu Glu Ala Glu Asn Arg Leu Tyr Ala Ala
305                 310                 315                 320

Met Ser Ala Ile Asp Ile Phe Val Asn Asn Lys Gly Asn Phe Lys Asp
                325                 330                 335

Leu Lys

<210> SEQ ID NO 10
<211> LENGTH: 1810
<212> TYPE: DNA
<213> ORGANISM: Pichia pastoris
<220> FEATURE:
<221> NAME/KEY: CDS
<222> LOCATION: (605)..(655)
<220> FEATURE:
<221> NAME/KEY: CDS
<222> LOCATION: (737)..(1576)

<400> SEQUENCE: 10
caagttgcgt ccggtatacg taacgtctca cgatgatcaa agataatact taatcttcat      60
ggtctactga ataactcatt taaacaattg actaattgta cattatattg aacttatgca     120
tcctattaac gtaatcttct ggcttctctc tcagactcca tcagacacag aatatcgttc     180
tctctaactg gtcctttgac gtttctgaca atagttctag aggagtcgtc caaaaactca     240
actctgactt gggtgacacc accacgggat ccggttcttc cgaggacctt gatgaccttg     300
gctaatgtaa ctggagtttt agtatccatt ttaagatgtg tgtttctgta ggttctgggt     360
tggaaaaaaa ttttagacac cagaagagag gagtgaactg gtttgcgtgg gtttagactg     420
tgtaaggcac tactctgtcg aagttttaga taggggttac ccgctccgat gcatgggaag     480
cgattagccc ggctgttgcc cgtttggttt ttgaagggta attttcaata tctctgtttg     540
agtcatcaat ttcatattca aagattcaaa aacaaaatct ggtccaagga gcgcatttag     600 gatt atg gag ttg gcg aat cac ttg aac gat aga cta tta ttt gct gtt        649
     Met Glu Leu Ala Asn His Leu Asn Asp Arg Leu Leu Phe Ala Val
       1               5                  10                  15 cct aaa agtatgtagc atgtcgtttt tttttaaaa gggttttttc cctattctcc          705
Pro Lys actcacttta tactaacaac tatttttttc a gag ggc aga ttg tat gag aaa         757
                                  Glu Gly Arg Leu Tyr Glu Lys
                                                       20 tgc gtt gaa tta ctt agg gga tca gat att cag ttt cga aga tcc agt        805
Cys Val Glu Leu Leu Arg Gly Ser Asp Ile Gln Phe Arg Arg Ser Ser
 25                  30                  35                  40 aga ttg gat ata gct ttg tgc act aac ctg ccc ctg gca ttg gtt ttc        853
Arg Leu Asp Ile Ala Leu Cys Thr Asn Leu Pro Leu Ala Leu Val Phe
                 45                  50                  55 ctt cca gct gct gac att ccc acg ttt gta gga gag ggt aaa tgt gat        901
Leu Pro Ala Ala Asp Ile Pro Thr Phe Val Gly Glu Gly Lys Cys Asp
             60                  65                  70 ttg ggt ata act ggt att gac cag gtt cag gaa agt gac gta gat gtc        949
Leu Gly Ile Thr Gly Ile Asp Gln Val Gln Glu Ser Asp Val Asp Val
         75                  80                  85 ata cct tta tta gac ttg aat ttc ggt aag tgc aag ttg cag att caa        997
Ile Pro Leu Leu Asp Leu Asn Phe Gly Lys Cys Lys Leu Gln Ile Gln
         90                  95                 100 gtt ccc gag aat ggt gac ttg aaa gaa cct aaa cag cta att ggt aaa       1045
Val Pro Glu Asn Gly Asp Leu Lys Glu Pro Lys Gln Leu Ile Gly Lys
105                 110                 115                 120 gaa att gtt tcc tcc ttt act agc tta acc acc agg tac ttt gaa caa       1093
```

```
Glu Ile Val Ser Ser Phe Thr Ser Leu Thr Thr Arg Tyr Phe Glu Gln
            125                 130                 135 ctg gaa gga gtt aag cct ggt gag cca cta aag aca aaa atc aaa tat      1141
Leu Glu Gly Val Lys Pro Gly Glu Pro Leu Lys Thr Lys Ile Lys Tyr
                140                 145                 150 gtt gga ggg tct gtt gag gcc tct tgt gcc cta gga gtt gcc gat gct      1189
Val Gly Gly Ser Val Glu Ala Ser Cys Ala Leu Gly Val Ala Asp Ala
            155                 160                 165 att gtg gat ctt gtt gag agt gga gaa acc atg aaa gcg gca ggg ctg      1237
Ile Val Asp Leu Val Glu Ser Gly Glu Thr Met Lys Ala Ala Gly Leu
        170                 175                 180 atc gat att gaa act gtt ctt tct act tcc gct tac ctg atc tct tcg      1285
Ile Asp Ile Glu Thr Val Leu Ser Thr Ser Ala Tyr Leu Ile Ser Ser
185                 190                 195                 200 aag cat cct caa cac cca gaa ctg atg gat act atc aag gag aga att      1333
Lys His Pro Gln His Pro Glu Leu Met Asp Thr Ile Lys Glu Arg Ile
                205                 210                 215 gaa ggt gta ctg act gct cag aag tat gtc ttg tgt aat tac aac gca      1381
Glu Gly Val Leu Thr Ala Gln Lys Tyr Val Leu Cys Asn Tyr Asn Ala
            220                 225                 230 cct aga ggt aac ctt cct cag ctg cta aaa ctg act cca ggc aag aga      1429
Pro Arg Gly Asn Leu Pro Gln Leu Leu Lys Leu Thr Pro Gly Lys Arg
        235                 240                 245 gct gct acc gtt tct cca tta gat gaa gaa gat tgg gtg gga gtg tcc      1477
Ala Ala Thr Val Ser Pro Leu Asp Glu Glu Asp Trp Val Gly Val Ser
    250                 255                 260 tcg atg gta gag aag aaa gat gtt gga aga atc atg gac gaa tta aag      1525
Ser Met Val Glu Lys Lys Asp Val Gly Arg Ile Met Asp Glu Leu Lys
265                 270                 275                 280 aaa caa ggt gcc agt gac att ctt gtc ttt gag atc agt aat tgt aga      1573
Lys Gln Gly Ala Ser Asp Ile Leu Val Phe Glu Ile Ser Asn Cys Arg
                285                 290                 295 gca tagataaat aatattcaag accaacggct tctcttcgga agctccaagt             1626
Ala agcttatagt gatgagtacc ggcatatatt tataggctta aaatttcgag ggttcactat     1686
attcgtttag tgggaagagt tcctttcact cttgttatct atattgtcag cgtggactgt     1746
ttataactgt accaacttag tttctttcaa ctccaggtta agagacataa atgtcctttg     1806
atgc                                                                  1810

<210> SEQ ID NO 11
<211> LENGTH: 297
<212> TYPE: PRT
<213> ORGANISM: Pichia pastoris

<400> SEQUENCE: 11

Met Glu Leu Ala Asn His Leu Asn Asp Arg Leu Leu Phe Ala Val Pro
1               5                   10                  15

Lys Glu Gly Arg Leu Tyr Glu Lys Cys Val Glu Leu Leu Arg Gly Ser
            20                  25                  30

Asp Ile Gln Phe Arg Arg Ser Ser Arg Leu Asp Ile Ala Leu Cys Thr
        35                  40                  45

Asn Leu Pro Leu Ala Leu Val Phe Leu Pro Ala Ala Asp Ile Pro Thr
    50                  55                  60

Phe Val Gly Glu Gly Lys Cys Asp Leu Gly Ile Thr Gly Ile Asp Gln
65                  70                  75                  80

Val Gln Glu Ser Asp Val Asp Val Ile Pro Leu Leu Asp Leu Asn Phe
                85                  90                  95
```

-continued

```
Gly Lys Cys Lys Leu Gln Ile Gln Val Pro Glu Asn Gly Asp Leu Lys
            100                 105                 110

Glu Pro Lys Gln Leu Ile Gly Lys Glu Ile Val Ser Ser Phe Thr Ser
        115                 120                 125

Leu Thr Thr Arg Tyr Phe Glu Gln Leu Glu Gly Val Lys Pro Gly Glu
    130                 135                 140

Pro Leu Lys Thr Lys Ile Lys Tyr Val Gly Gly Ser Val Glu Ala Ser
145                 150                 155                 160

Cys Ala Leu Gly Val Ala Asp Ala Ile Val Asp Leu Val Glu Ser Gly
                165                 170                 175

Glu Thr Met Lys Ala Ala Gly Leu Ile Asp Ile Glu Thr Val Leu Ser
            180                 185                 190

Thr Ser Ala Tyr Leu Ile Ser Ser Lys His Pro Gln His Pro Glu Leu
        195                 200                 205

Met Asp Thr Ile Lys Glu Arg Ile Glu Gly Val Leu Thr Ala Gln Lys
    210                 215                 220

Tyr Val Leu Cys Asn Tyr Asn Ala Pro Arg Gly Asn Leu Pro Gln Leu
225                 230                 235                 240

Leu Lys Leu Thr Pro Gly Lys Arg Ala Ala Thr Val Ser Pro Leu Asp
                245                 250                 255

Glu Glu Asp Trp Val Gly Val Ser Ser Met Val Glu Lys Lys Asp Val
            260                 265                 270

Gly Arg Ile Met Asp Glu Leu Lys Lys Gln Gly Ala Ser Asp Ile Leu
        275                 280                 285

Val Phe Glu Ile Ser Asn Cys Arg Ala
    290                 295

<210> SEQ ID NO 12
<211> LENGTH: 297
<212> TYPE: PRT
<213> ORGANISM: Saccharomyces cerevisiae

<400> SEQUENCE: 12

Met Asp Leu Val Asn His Leu Thr Asp Arg Leu Leu Phe Ala Ile Pro
  1               5                  10                  15

Lys Lys Gly Arg Leu Tyr Ser Lys Ser Val Ser Ile Leu Asn Gly Ala
                 20                  25                  30

Asp Ile Thr Phe His Arg Ser Gln Arg Leu Asp Ile Ala Leu Ser Thr
             35                  40                  45

Ser Leu Pro Val Ala Leu Val Phe Leu Pro Ala Ala Asp Ile Pro Thr
     50                  55                  60

Phe Val Gly Glu Gly Lys Cys Asp Leu Gly Ile Thr Gly Val Asp Gln
 65                  70                  75                  80

Val Arg Glu Ser Asn Val Asp Val Asp Leu Ala Ile Asp Leu Gln Phe
                 85                  90                  95

Gly Asn Cys Lys Leu Gln Val Gln Val Pro Val Asn Gly Glu Tyr Lys
            100                 105                 110

Lys Pro Glu Gln Leu Ile Gly Lys Thr Ile Val Thr Ser Phe Val Lys
        115                 120                 125

Leu Ala Glu Lys Tyr Phe Ala Asp Leu Glu Gly Thr Thr Val Glu Lys
    130                 135                 140

Met Thr Thr Arg Ile Lys Phe Val Ser Gly Ser Val Glu Ala Ser Cys
145                 150                 155                 160

Ala Leu Gly Ile Gly Asp Ala Ile Val Asp Leu Val Glu Ser Gly Glu
```

```
                           165                 170                 175
Thr Met Arg Ala Ala Gly Leu Val Asp Ile Ala Thr Val Leu Ser Thr
            180                 185                 190

Ser Ala Tyr Leu Ile Glu Ser Lys Asn Pro Lys Ser Asp Lys Ser Leu
        195                 200                 205

Ile Ala Thr Ile Lys Ser Arg Ile Glu Gly Val Met Thr Ala Gln Arg
    210                 215                 220

Phe Val Ser Cys Ile Tyr Asn Ala Pro Glu Asp Lys Leu Pro Glu Leu
225                 230                 235                 240

Leu Lys Val Thr Pro Gly Arg Arg Ala Pro Thr Ile Ser Lys Ile Asp
            245                 250                 255

Asp Glu Gly Trp Val Ala Val Ser Ser Met Ile Glu Arg Lys Thr Lys
        260                 265                 270

Gly Val Val Leu Asp Glu Leu Lys Arg Leu Gly Ala Ser Asp Ile Met
    275                 280                 285

Val Phe Glu Ile Ser Asn Cys Arg Val
    290                 295

<210> SEQ ID NO 13
<211> LENGTH: 2068
<212> TYPE: DNA
<213> ORGANISM: Pichia pastoris
<220> FEATURE:
<221> NAME/KEY: CDS
<222> LOCATION: (912)..(1835)

<400> SEQUENCE: 13
cgattgctca tcttcagaag aagtcttcaa atgaggaatt gaagagttat caagttaagt      60
ggcaagaata gaaactttaa aattaagggt ttccagttgt gcatttatag ggatataaga     120
aatgaaaaca aaacattttc ggaatcggaa actctttctt ccgaatttcc gtttccgaag     180
acataacatt gattctccag gtctaaattt aggaaaaatg ccaaaaaaaa gcgactgagc     240
atctgcatcg atcggagtag acaactggtt agttgccgtg cctctcagaa ccaaagttga     300
gctggttaac gtctgacttg acagcggaac ttggaatctt cggaagactc taggatgcct     360 aaatttttcga tgcctccaaa atctcaatgt ggcttacggg aatctacggc tcaccttaca     420
acgaaattgg acaatcagc aagcagtcta tcgatcgttg tttacaaaat atttcgctac     480
caagaagaga caccccgttt gttggggagt acggattgtt gattaccaat cgccaatttc     540
cggggcttac catgattatg cataacttct cggaattagg tcttgaactg aaattactca     600
tgctcagtgc atacacttat ccctagccgc attgactctg tgagcttccg gagtgttagt     660
agttccgacc gttagataat cgtgctttct ttctttttta gtgttgttgt attattaata     720
cgatgctggt ggcttagaaa tagcgatcgt gactgcgatg tctagtcgcc tgatgagttg     780
acttcttcct ccctccggtt tcacccacta ctaggcttag cagttcttgg cttttctgtc     840
cccctcgcgg aaatgttctc acgtcttccg cctaacagat tgttctggcg gttttagtcg     900
tctagctatt g atg cat tcc cat cat tcc cat agt gga agt tac gtt tct    950
              Met His Ser His His Ser His Ser Gly Ser Tyr Val Ser
                 1               5                  10 cat gca acg gat aca ctg gat gaa atc gta gac aaa gct att gag ctc      998
His Ala Thr Asp Thr Leu Asp Glu Ile Val Asp Lys Ala Ile Glu Leu
        15                  20                  25 cat ttc caa aca tat tgt ctc act gaa cat atg ccc aga tat aag gat     1046
His Phe Gln Thr Tyr Cys Leu Thr Glu His Met Pro Arg Tyr Lys Asp
 30                  35                  40                  45
```

```
gaa gat ctc tat cct gaa gaa att gaa aag agg ttt acc tat aag tgt    1094
Glu Asp Leu Tyr Pro Glu Glu Ile Glu Lys Arg Phe Thr Tyr Lys Cys
         50                  55                  60 ctg gtc gaa caa ttt gac cag ttt tat aag cat gca aaa gtt ata aaa    1142
Leu Val Glu Gln Phe Asp Gln Phe Tyr Lys His Ala Lys Val Ile Lys
 65                  70                  75 gag aca agg aac att gat ccc cag tgt gat aca aga ttt ctt ata ggg    1190
Glu Thr Arg Asn Ile Asp Pro Gln Cys Asp Thr Arg Phe Leu Ile Gly
         80                  85                  90 ttt gaa act gaa gga ggt ctt ggt gat tat caa ctg gat caa tgt ttg    1238
Phe Glu Thr Glu Gly Gly Leu Gly Asp Tyr Gln Leu Asp Gln Cys Leu
     95                 100                 105 aaa tta cgc ctg aca tat cct gtt gac ttg att gtt gga tcg ata cac    1286
Lys Leu Arg Leu Thr Tyr Pro Val Asp Leu Ile Val Gly Ser Ile His
110                 115                 120                 125 cat tta gac tcc att cct att gat atc gat agg gca aac tgg cta aaa    1334
His Leu Asp Ser Ile Pro Ile Asp Ile Asp Arg Ala Asn Trp Leu Lys
                130                 135                 140 gcc aaa gat gca aca act tcg aat ggt tcg atc aga gac ttc tat ttt    1382
Ala Lys Asp Ala Thr Thr Ser Asn Gly Ser Ile Arg Asp Phe Tyr Phe
            145                 150                 155 ctc tac ttc aaa act caa caa tta atg att caa aaa cta agg cca gaa    1430
Leu Tyr Phe Lys Thr Gln Gln Leu Met Ile Gln Lys Leu Arg Pro Glu
        160                 165                 170 gtg atc ggg cat ttt gac ctc ata aga ttt tac aac gaa gat ggc gac    1478
Val Ile Gly His Phe Asp Leu Ile Arg Phe Tyr Asn Glu Asp Gly Asp
    175                 180                 185 caa tta ttt caa tgg cca gag gta gta gcg tta att gaa gag aat ata    1526
Gln Leu Phe Gln Trp Pro Glu Val Val Ala Leu Ile Glu Glu Asn Ile
190                 195                 200                 205 gac ttg ata aat tcg tat gat gga tta att gag ctc aat tca gct gct    1574
Asp Leu Ile Asn Ser Tyr Asp Gly Leu Ile Glu Leu Asn Ser Ala Ala
                210                 215                 220 att agg aaa ggt tgg ccg tct cca tac cca aaa tct gat gtc atc aat    1622
Ile Arg Lys Gly Trp Pro Ser Pro Tyr Pro Lys Ser Asp Val Ile Asn
            225                 230                 235 ttt att ttt agt aga gga gga aaa ttt tgc ttt agc gat gac gcc cat    1670
Phe Ile Phe Ser Arg Gly Gly Lys Phe Cys Phe Ser Asp Asp Ala His
        240                 245                 250 agt gtg gga caa gtt ggc tta aac tac atg aaa atg cta gag ttt gtt    1718
Ser Val Gly Gln Val Gly Leu Asn Tyr Met Lys Met Leu Glu Phe Val
    255                 260                 265 gaa caa tcg aca gaa att gac aag atc tgg tac tat gat ttg agc aac    1766
Glu Gln Ser Thr Glu Ile Asp Lys Ile Trp Tyr Tyr Asp Leu Ser Asn
270                 275                 280                 285 act gat aaa ctt att caa aag agt att cca gtt tct aga tta agg gac    1814
Thr Asp Lys Leu Ile Gln Lys Ser Ile Pro Val Ser Arg Leu Arg Asp
                290                 295                 300 cat gta ttc tgg aat tca ggc taaataaatc taatcacgta ttataggcga       1865
His Val Phe Trp Asn Ser Gly
            305 gagtatcaat tttatcccag acgttgttat aatgagttag catttcttcg aatcccacta  1925 agttataagt tctaagtgtt ttccatctat tgttcacttg gccttcatcc aaagaaaaca  1985 acttttgcaa tccgagttta acatcttttt tagcctttgc tttatttatt ggtactccat  2045 atttgatgga gatatcttca acc                                          2068

<210> SEQ ID NO 14
<211> LENGTH: 308
```

```
<212> TYPE: PRT
<213> ORGANISM: Pichia pastoris

<400> SEQUENCE: 14

Met His Ser His His Ser His Ser Gly Ser Tyr Val Ser His Ala Thr
 1               5                  10                  15

Asp Thr Leu Asp Glu Ile Val Asp Lys Ala Ile Glu Leu His Phe Gln
            20                  25                  30

Thr Tyr Cys Leu Thr Glu His Met Pro Arg Tyr Lys Asp Glu Asp Leu
        35                  40                  45

Tyr Pro Glu Glu Ile Glu Lys Arg Phe Thr Tyr Lys Cys Leu Val Glu
    50                  55                  60

Gln Phe Asp Gln Phe Tyr Lys His Ala Lys Val Ile Lys Glu Thr Arg
65                  70                  75                  80

Asn Ile Asp Pro Gln Cys Asp Thr Arg Phe Leu Ile Gly Phe Glu Thr
                85                  90                  95

Glu Gly Gly Leu Gly Asp Tyr Gln Leu Asp Gln Cys Leu Lys Leu Arg
            100                 105                 110

Leu Thr Tyr Pro Val Asp Leu Ile Val Gly Ser Ile His His Leu Asp
        115                 120                 125

Ser Ile Pro Ile Asp Ile Asp Arg Ala Asn Trp Leu Lys Ala Lys Asp
    130                 135                 140

Ala Thr Thr Ser Asn Gly Ser Ile Arg Asp Phe Tyr Phe Leu Tyr Phe
145                 150                 155                 160

Lys Thr Gln Gln Leu Met Ile Gln Lys Leu Arg Pro Glu Val Ile Gly
                165                 170                 175

His Phe Asp Leu Ile Arg Phe Tyr Asn Glu Asp Gly Asp Gln Leu Phe
            180                 185                 190

Gln Trp Pro Glu Val Val Ala Leu Ile Glu Glu Asn Ile Asp Leu Ile
        195                 200                 205

Asn Ser Tyr Asp Gly Leu Ile Glu Leu Asn Ser Ala Ala Ile Arg Lys
    210                 215                 220

Gly Trp Pro Ser Pro Tyr Pro Lys Ser Asp Val Ile Asn Phe Ile Phe
225                 230                 235                 240

Ser Arg Gly Gly Lys Phe Cys Phe Ser Asp Asp Ala His Ser Val Gly
                245                 250                 255

Gln Val Gly Leu Asn Tyr Met Lys Met Leu Glu Phe Val Glu Gln Ser
            260                 265                 270

Thr Glu Ile Asp Lys Ile Trp Tyr Tyr Asp Leu Ser Asn Thr Asp Lys
        275                 280                 285

Leu Ile Gln Lys Ser Ile Pro Val Ser Arg Leu Arg Asp His Val Phe
    290                 295                 300

Trp Asn Ser Gly
305

<210> SEQ ID NO 15
<211> LENGTH: 335
<212> TYPE: PRT
<213> ORGANISM: Saccharomyces cerevisiae

<400> SEQUENCE: 15

Met His Ser His His Ser His Ser Gly Asp Tyr Ser Ala His Gly Thr
 1               5                  10                  15

Asp Pro Leu Asp Ser Val Val Asp Gln Val Val Asn Leu Asn Phe His
            20                  25                  30
```

```
Thr Tyr Cys Leu Thr Glu His Ile Pro Arg Ile Glu Ala Lys Phe Ile
         35                  40                  45

Tyr Pro Glu Glu Gln Ser Leu Gly Lys Asn Pro Glu Glu Val Ile Thr
 50                  55                  60

Lys Leu Glu Thr Ser Phe Lys Asn Phe Met Ser His Ala Gln Glu Ile
 65                  70                  75                  80

Lys Thr Arg Tyr Ala Asp Arg Pro Asp Val Arg Thr Lys Phe Ile Ile
             85                  90                  95

Gly Met Glu Ile Glu Ser Cys Asp Met Ala His Ile Glu Tyr Ala Lys
            100                 105                 110

Arg Leu Met Lys Glu Asn Asn Asp Ile Leu Lys Phe Cys Val Gly Ser
            115                 120                 125

Val His His Val Asn Gly Ile Pro Ile Asp Phe Asp Gln Gln Gln Trp
        130                 135                 140

Tyr Asn Ser Leu His Ser Phe Asn Asp Asn Leu Lys His Phe Leu Leu
145                 150                 155                 160

Ser Tyr Phe Gln Ser Gln Tyr Glu Met Leu Ile Asn Ile Lys Pro Leu
                165                 170                 175

Val Val Gly His Phe Asp Leu Tyr Lys Leu Phe Leu Pro Asn Asp Met
            180                 185                 190

Leu Val Asn Gln Lys Ser Gly Asn Cys Asn Glu Glu Thr Gly Val Pro
        195                 200                 205

Val Ala Ser Leu Asp Val Ile Ser Glu Trp Pro Glu Ile Tyr Asp Ala
    210                 215                 220

Val Val Arg Asn Leu Gln Phe Ile Asp Ser Tyr Gly Gly Ala Ile Glu
225                 230                 235                 240

Ile Asn Thr Ser Ala Leu Arg Lys Arg Leu Glu Glu Pro Tyr Pro Ser
                245                 250                 255

Lys Thr Leu Cys Asn Leu Val Lys Lys His Cys Gly Ser Arg Phe Val
            260                 265                 270

Leu Ser Asp Asp Ala His Gly Val Ala Gln Val Gly Val Cys Tyr Asp
        275                 280                 285

Lys Val Lys Lys Tyr Ile Val Asp Val Leu Gln Leu Tyr Ile Cys
    290                 295                 300

Tyr Leu Glu Glu Ser Gln Ser Pro Glu Asn Leu Leu Thr Val Lys Arg
305                 310                 315                 320

Leu Pro Ile Ser Gln Phe Val Asn Asp Pro Phe Trp Ala Asn Ile
                325                 330                 335

<210> SEQ ID NO 16
<211> LENGTH: 1928
<212> TYPE: DNA
<213> ORGANISM: Pichia pastoris
<220> FEATURE:
<221> NAME/KEY: CDS
<222> LOCATION: (423)..(1592)

<400> SEQUENCE: 16
gcaaaatgct ttctggaact caagggtctt gtggcttcaa ttctgacaat atctccctct      60
ttacaaatgt taccctcatc atgaacaaga tagttttttcc tcttgaacaa agacttgtga    120
atctttgtgt tatacgccat tgctctacg cgtactttga cagtttttatc catcttacct    180 tgtgaaacca caaggcctat aaagttctgc ctggccattt gttcgatttt tggatatgtc    240
tttgagtaaa atttttgaagc tcaactaaca tgtccaattt tcagtagaga tacacgacct    300 ataatttttcg caggctctct gacgcttaag gaagcacggc aggtccaatt tagagattgt    360
```

```
gactcagatc tctgaagcct ctacatacaa catacaattt gcaatttttt tgagctagta    420 tc atg gtt ttt gac tac aag aga ctg gtt aga cct aac atc ttg agt        467
   Met Val Phe Asp Tyr Lys Arg Leu Val Arg Pro Asn Ile Leu Ser
   1               5                  10                  15 ttg gag cct tac aga tgc gcc cgt gac gat ttt aag gaa gga att ctg       515
Leu Glu Pro Tyr Arg Cys Ala Arg Asp Asp Phe Lys Glu Gly Ile Leu
                20                  25                  30 ctt gat gct aat gaa aat act cat gga cct agt ata tct gac ctt agc      563
Leu Asp Ala Asn Glu Asn Thr His Gly Pro Ser Ile Ser Asp Leu Ser
                    35                  40                  45 acc tca gag gat gac ttg caa ctt aac aga tat cct gat cct cat cag      611
Thr Ser Glu Asp Asp Leu Gln Leu Asn Arg Tyr Pro Asp Pro His Gln
            50                  55                  60 ttg gag cta aag caa caa atc tgt aat att aga aat caa gaa acc ccc      659
Leu Glu Leu Lys Gln Gln Ile Cys Asn Ile Arg Asn Gln Glu Thr Pro
        65                  70                  75 atc gaa ggg gag aaa gtt gag gtg gag aac tta tgc ctg ggt gtg ggt      707
Ile Glu Gly Glu Lys Val Glu Val Glu Asn Leu Cys Leu Gly Val Gly
80                  85                  90                  95 tct gac gaa agt att gac gcc ttg atg aga tgt ttt ttg acc cct tca      755
Ser Asp Glu Ser Ile Asp Ala Leu Met Arg Cys Phe Leu Thr Pro Ser
                100                 105                 110 aaa gat aaa cta ttg att tgt aca cct act tat ggg atg tat gga atc      803
Lys Asp Lys Leu Leu Ile Cys Thr Pro Thr Tyr Gly Met Tyr Gly Ile
            115                 120                 125 tgt gct acg att aat gac att gaa att gtg aaa tgt cct ttg aac ttg      851
Cys Ala Thr Ile Asn Asp Ile Glu Ile Val Lys Cys Pro Leu Asn Leu
        130                 135                 140 cag agc ttc cag ata caa ccg gaa gaa atc ttg aaa gtt gtt caa aat      899
Gln Ser Phe Gln Ile Gln Pro Glu Glu Ile Leu Lys Val Val Gln Asn
    145                 150                 155 gat cct act atc aag tta ctt tat ctc act tct cct ggt aat cca aca      947
Asp Pro Thr Ile Lys Leu Leu Tyr Leu Thr Ser Pro Gly Asn Pro Thr
160                 165                 170                 175 ggc caa tta att gac ttc agt ctg gta gag aca att tta aac gcg tgg      995
Gly Gln Leu Ile Asp Phe Ser Leu Val Glu Thr Ile Leu Asn Ala Trp
                180                 185                 190 gaa ggt ggt atc gtc ata ctg gat gag gca tat att gat ttt tca ccc     1043
Glu Gly Gly Ile Val Ile Leu Asp Glu Ala Tyr Ile Asp Phe Ser Pro
            195                 200                 205 gtg gga tcg tct aga agc acc ctg gtc aac aaa tat ccg aac ttg atc     1091
Val Gly Ser Ser Arg Ser Thr Leu Val Asn Lys Tyr Pro Asn Leu Ile
        210                 215                 220 gta ctt cag act ctt tct aaa gca ttt ggt cta gcg ggt ata aga ctt     1139
Val Leu Gln Thr Leu Ser Lys Ala Phe Gly Leu Ala Gly Ile Arg Leu
    225                 230                 235 ggt atc aca ttt gcc agc aaa cca att tcc gcg ttg ctg aat gcg tta     1187
Gly Ile Thr Phe Ala Ser Lys Pro Ile Ser Ala Leu Leu Asn Ala Leu
240                 245                 250                 255 aag tac cct tac aat att tcc aat ctg act tct aat att gct ttg aga     1235
Lys Tyr Pro Tyr Asn Ile Ser Asn Leu Thr Ser Asn Ile Ala Leu Arg
                260                 265                 270 gct acg ttg cct gag aac gtc caa gaa atg aga agc aaa tgc aaa gca     1283
Ala Thr Leu Pro Glu Asn Val Gln Glu Met Arg Ser Lys Cys Lys Ala
            275                 280                 285 atc tgc aat gaa agg gag ttt gtc ata gat tcc ctg aca aaa cta cca     1331
Ile Cys Asn Glu Arg Glu Phe Val Ile Asp Ser Leu Thr Lys Leu Pro
        290                 295                 300
```

```
aac gtc ggc cgc gtc att ggc ggc cta gat gcc aac ttc att ctt ttg    1379
Asn Val Gly Arg Val Ile Gly Gly Leu Asp Ala Asn Phe Ile Leu Leu
305                 310                 315 caa ttt ctt gat aca aat gga aaa ccc tct aat gag gtt gcc aag aag    1427
Gln Phe Leu Asp Thr Asn Gly Lys Pro Ser Asn Glu Val Ala Lys Lys
320                 325                 330                 335 ctt tac act aca ttg gcc acc gag aat aag gta gtt att cga tac aga    1475
Leu Tyr Thr Thr Leu Ala Thr Glu Asn Lys Val Val Ile Arg Tyr Arg
            340                 345                 350 gga agt gaa ctt gga tgc gaa ggt tgt ttg aga att agt att gga acc    1523
Gly Ser Glu Leu Gly Cys Glu Gly Cys Leu Arg Ile Ser Ile Gly Thr
        355                 360                 365 aga gag gaa aac aat act ttg ata gac caa atg tca aaa gta cta cca    1571
Arg Glu Glu Asn Asn Thr Leu Ile Asp Gln Met Ser Lys Val Leu Pro
    370                 375                 380 cag gtt atc aaa tca tct aca tagataatct tcataatata aatatacagt       1622
Gln Val Ile Lys Ser Ser Thr
385                 390 tttgtggtca cgatgtctta tctcatcgtc tcatttctat ttaaacagtt gctcaaccaa  1682
tgcattcagc tttccgctat aaaagtcacc atgttgaggt ccgctacctt ggacgttttc  1742
ttcgtcgttc agatgcttct tgagcttatc taatgactcc aaatcctttt tgatacgata  1802
ccttggatca agtatatcag aaagaccaat ttccacatcc tctccagtgt tggaaattgc  1862
ggtgacacta attgcgcaag attctaaagc cagaagctca cttggatgac cgctgtcatc  1922
cttggg                                                              1928

<210> SEQ ID NO 17
<211> LENGTH: 390
<212> TYPE: PRT
<213> ORGANISM: Pichia pastoris

<400> SEQUENCE: 17

Met Val Phe Asp Tyr Lys Arg Leu Val Arg Pro Asn Ile Leu Ser Leu
1               5                   10                  15

Glu Pro Tyr Arg Cys Ala Arg Asp Asp Phe Lys Glu Gly Ile Leu Leu
            20                  25                  30

Asp Ala Asn Glu Asn Thr His Gly Pro Ser Ile Ser Asp Leu Ser Thr
        35                  40                  45

Ser Glu Asp Asp Leu Gln Leu Asn Arg Tyr Pro Asp Pro His Gln Leu
    50                  55                  60

Glu Leu Lys Gln Gln Ile Cys Asn Ile Arg Asn Gln Glu Thr Pro Ile
65                  70                  75                  80

Glu Gly Glu Lys Val Glu Val Glu Asn Leu Cys Leu Gly Val Gly Ser
                85                  90                  95

Asp Glu Ser Ile Asp Ala Leu Met Arg Cys Phe Leu Thr Pro Ser Lys
            100                 105                 110

Asp Lys Leu Leu Ile Cys Thr Pro Thr Tyr Gly Met Tyr Gly Ile Cys
        115                 120                 125

Ala Thr Ile Asn Asp Ile Glu Ile Val Lys Cys Pro Leu Asn Leu Gln
    130                 135                 140

Ser Phe Gln Ile Gln Pro Glu Glu Ile Leu Lys Val Val Gln Asn Asp
145                 150                 155                 160

Pro Thr Ile Lys Leu Leu Tyr Leu Thr Ser Pro Gly Asn Pro Thr Gly
                165                 170                 175

Gln Leu Ile Asp Phe Ser Leu Val Glu Thr Ile Leu Asn Ala Trp Glu
            180                 185                 190
```

-continued

Gly Gly Ile Val Ile Leu Asp Glu Ala Tyr Ile Asp Phe Ser Pro Val
        195                 200                 205

Gly Ser Ser Arg Ser Thr Leu Val Asn Lys Tyr Pro Asn Leu Ile Val
210                 215                 220

Leu Gln Thr Leu Ser Lys Ala Phe Gly Leu Ala Gly Ile Arg Leu Gly
225                 230                 235                 240

Ile Thr Phe Ala Ser Lys Pro Ile Ser Ala Leu Leu Asn Ala Leu Lys
                245                 250                 255

Tyr Pro Tyr Asn Ile Ser Asn Leu Thr Ser Asn Ile Ala Leu Arg Ala
            260                 265                 270

Thr Leu Pro Glu Asn Val Gln Glu Met Arg Ser Lys Cys Lys Ala Ile
        275                 280                 285

Cys Asn Glu Arg Glu Phe Val Ile Asp Ser Leu Thr Lys Leu Pro Asn
    290                 295                 300

Val Gly Arg Val Ile Gly Gly Leu Asp Ala Asn Phe Ile Leu Leu Gln
305                 310                 315                 320

Phe Leu Asp Thr Asn Gly Lys Pro Ser Asn Glu Val Ala Lys Lys Leu
                325                 330                 335

Tyr Thr Thr Leu Ala Thr Glu Asn Lys Val Val Ile Arg Tyr Arg Gly
            340                 345                 350

Ser Glu Leu Gly Cys Glu Gly Cys Leu Arg Ile Ser Ile Gly Thr Arg
        355                 360                 365

Glu Glu Asn Asn Thr Leu Ile Asp Gln Met Ser Lys Val Leu Pro Gln
    370                 375                 380

Val Ile Lys Ser Ser Thr
385                 390

<210> SEQ ID NO 18
<211> LENGTH: 385
<212> TYPE: PRT
<213> ORGANISM: Saccharomyces cerevisiae

<400> SEQUENCE: 18

Met Val Phe Asp Leu Lys Arg Ile Val Arg Pro Lys Ile Tyr Asn Leu
1               5                   10                  15

Glu Pro Tyr Arg Cys Ala Arg Asp Asp Phe Thr Glu Gly Ile Leu Leu
            20                  25                  30

Asp Ala Asn Glu Asn Ala His Gly Pro Thr Pro Val Glu Leu Ser Lys
        35                  40                  45

Thr Asn Leu His Arg Tyr Pro Asp Pro His Gln Leu Glu Phe Lys Thr
    50                  55                  60

Ala Met Thr Lys Tyr Arg Asn Lys Thr Ser Ser Tyr Ala Asn Asp Pro
65                  70                  75                  80

Glu Val Lys Pro Leu Thr Ala Asp Asn Leu Cys Leu Gly Val Gly Ser
                85                  90                  95

Asp Glu Ser Ile Asp Ala Ile Ile Arg Ala Cys Cys Val Pro Gly Lys
            100                 105                 110

Glu Lys Ile Leu Val Leu Pro Pro Thr Tyr Ser Met Tyr Ser Val Cys
        115                 120                 125

Ala Asn Ile Asn Asp Ile Glu Val Val Gln Cys Pro Leu Thr Val Ser
    130                 135                 140

Asp Gly Ser Phe Gln Met Asp Thr Glu Ala Val Leu Thr Ile Leu Lys
145                 150                 155                 160

Asn Asp Ser Leu Ile Lys Leu Met Phe Val Thr Ser Pro Gly Asn Pro

```
                165                 170                 175
Thr Gly Ala Lys Ile Lys Thr Ser Leu Ile Glu Lys Val Leu Gln Asn
            180                 185                 190

Trp Asp Asn Gly Leu Val Val Asp Glu Ala Tyr Val Asp Phe Cys
        195                 200                 205

Gly Gly Ser Thr Ala Pro Leu Val Thr Lys Tyr Pro Asn Leu Val Thr
    210                 215                 220

Leu Gln Thr Leu Ser Lys Ser Phe Gly Leu Ala Gly Ile Arg Leu Gly
225                 230                 235                 240

Met Thr Tyr Ala Thr Ala Glu Leu Ala Arg Ile Leu Asn Ala Met Lys
                245                 250                 255

Ala Pro Tyr Asn Ile Ser Ser Leu Ala Ser Glu Tyr Ala Leu Lys Ala
            260                 265                 270

Val Gln Asp Ser Asn Leu Lys Lys Met Glu Ala Thr Ser Lys Ile Ile
        275                 280                 285

Asn Glu Glu Lys Met Arg Leu Leu Lys Glu Leu Thr Ala Leu Asp Tyr
    290                 295                 300

Val Asp Asp Gln Tyr Val Gly Gly Leu Asp Ala Asn Phe Leu Leu Ile
305                 310                 315                 320

Arg Ile Asn Gly Gly Asp Asn Val Leu Ala Lys Lys Leu Tyr Tyr Gln
                325                 330                 335

Leu Ala Thr Gln Ser Gly Val Val Arg Phe Arg Gly Asn Glu Leu
            340                 345                 350

Gly Cys Ser Gly Cys Leu Arg Ile Thr Val Gly Thr His Glu Glu Asn
        355                 360                 365

Thr His Leu Ile Lys Tyr Phe Lys Glu Thr Leu Tyr Lys Leu Ala Asn
    370                 375                 380

Glu
385

<210> SEQ ID NO 19
<211> LENGTH: 1806
<212> TYPE: DNA
<213> ORGANISM: Pichia pastoris
<220> FEATURE:
<221> NAME/KEY: CDS
<222> LOCATION: (567)..(1355)

<400> SEQUENCE: 19
ccgttggcaa cataaggttg cagctggtaa ttgttatagc gagggaatct tgtagttctc      60
aggaccttta gctctttgtc gtaatatgtc tcagtgtctt catcgacaaa ataagtggct     120
cctgaactga gaccttcaga gatattagct ctggtgaagt tgtgactcag aagattccta     180
atctgcaagg aatcacttga agtgccaaca ggaaaggttg taaccaagtg aaagaaaacc     240
acacaagaaa gggcaaccaa caacactcta ttcagcattt ctctagtctg agaggtggga     300
ggaggtttct ttggtattct gctattatat atggatccat acggcattgc cctaatctag     360
tgaagtaaaa gccaaatgtt ccgcatcggt ccacggagaa atttgattgc tctatctggc     420
acctgaaagt ttgcgagttc ctaaattaga aatttaggtg cattaaacat ggggaatgta     480
tgactttttt ttttccgtct ttgggatctt gctcgccaga tcgagaggtt ttggagtaag     540
tgctccacca tagaaaaata gtccgt atg act gtc ttc aga ggt tgc atc gat     593
                         Met Thr Val Phe Arg Gly Cys Ile Asp
                           1               5 atc cat tcc ggc aaa gtc aaa cag att gta ggc ggc aag ctg gtg aag     641
Ile His Ser Gly Lys Val Lys Gln Ile Val Gly Gly Lys Leu Val Lys
```

```
                  10                  15                  20                  25
gat gac act gaa tct gat gaa gta gaa aca aat ttt gtc agt gaa cag         689
Asp Asp Thr Glu Ser Asp Glu Val Glu Thr Asn Phe Val Ser Glu Gln
                30                          35                  40 ccc tcg tcc tat tat gca cag tta tat aag cag aac cag gtt cat gga         737
Pro Ser Ser Tyr Tyr Ala Gln Leu Tyr Lys Gln Asn Gln Val His Gly
                45                          50                  55 aca cat gtc atc aaa ttg ggc tct tta aag gct aat gac gac gct gca         785
Thr His Val Ile Lys Leu Gly Ser Leu Lys Ala Asn Asp Asp Ala Ala
                60                          65                  70 aga gaa gct ctg ggt gcg tgg aga ggg ggt ttg cag att ggc ggt gga         833
Arg Glu Ala Leu Gly Ala Trp Arg Gly Gly Leu Gln Ile Gly Gly Gly
        75                          80                  85 ata acg gat tcc aat gct caa gaa tgg ata gat caa ggt gca tcg cat         881
Ile Thr Asp Ser Asn Ala Gln Glu Trp Ile Asp Gln Gly Ala Ser His
    90                          95                  100                 105 gtc ata gtc act tca tgg tta ttc cct gag ggt cag ttt tct ata gaa         929
Val Ile Val Thr Ser Trp Leu Phe Pro Glu Gly Gln Phe Ser Ile Glu
                    110                         115                 120 aga ctt caa cac ctg tcc agc ctt att gga aaa gag aaa ctg gta gtg         977
Arg Leu Gln His Leu Ser Ser Leu Ile Gly Lys Glu Lys Leu Val Val
                125                         130                 135 gac ttg agt tgt cgt aga caa gag ata gat gga agt ccc caa tgg gtg        1025
Asp Leu Ser Cys Arg Arg Gln Glu Ile Asp Gly Ser Pro Gln Trp Val
            140                         145                 150 gtt gct atg aac aaa tgg caa aca ttg acc tca tcc gtg cta gat aga        1073
Val Ala Met Asn Lys Trp Gln Thr Leu Thr Ser Ser Val Leu Asp Arg
        155                         160                 165 gag ttt ttc caa ctg ctg tcc cag tat tgc gat gag ttc tta gtg cat        1121
Glu Phe Phe Gln Leu Leu Ser Gln Tyr Cys Asp Glu Phe Leu Val His
170                         175                 180                 185 gct gca gat gtg gag gga ctt tgt caa gga att gac caa gag ctg gta        1169
Ala Ala Asp Val Glu Gly Leu Cys Gln Gly Ile Asp Gln Glu Leu Val
                    190                         195                 200 cgg aaa tta agt gaa tgg agt gat ctt cca gtt aca tat gct ggt ggg        1217
Arg Lys Leu Ser Glu Trp Ser Asp Leu Pro Val Thr Tyr Ala Gly Gly
                205                         210                 215 gct aga agt ata caa gat cta gaa act gtc aaa cat tta agc aac gga        1265
Ala Arg Ser Ile Gln Asp Leu Glu Thr Val Lys His Leu Ser Asn Gly
            220                         225                 230 aag gtc gat ctc acg ttt gga agt gca ctg aat att ttt ggc gga aac        1313
Lys Val Asp Leu Thr Phe Gly Ser Ala Leu Asn Ile Phe Gly Gly Asn
        235                         240                 245 cta gta aag ttt gaa gac tgt gtt aag tgg aat aaa act cag                1355
Leu Val Lys Phe Glu Asp Cys Val Lys Trp Asn Lys Thr Gln
250                         255                 260 tagattgcta ccttagttta tagttaatag tagagggtct ggtcagccct aggcttccaa      1415
aaatccgtat acctgcgttt cttccgcttg cgaatatctt tctcaatgct ggtcttagta     1475
tgtacaaaag ctctgcccac aagaagcctt ggataaatgg tttgataaca tggtcaattg     1535
caattgtata agcgacaact ttggcggtta cctggggctt agcggaggaa atgcgaactg     1595
aatttgcatt aagagtcctc caaaatgatt gctcgtaacg gagatcgggg atgactaatg     1655
tgttcatgat ggtcgatgag ccaagagggg ggttggactg gtcaaccctt ggataagcta     1715
aaaaagggag ccccgcgaag ggtctccctg aagcaaaccc ttgcacggaa ggaagaggtt     1775
ttcgctttgg gcgcggtagt tcaattcaac g                                    1806
```

<210> SEQ ID NO 20
<211> LENGTH: 263
<212> TYPE: PRT
<213> ORGANISM: Pichia pastoris

<400> SEQUENCE: 20

Met Thr Val Phe Arg Gly Cys Ile Asp Ile His Ser Gly Lys Val Lys
1               5                   10                  15

Gln Ile Val Gly Gly Lys Leu Val Lys Asp Asp Thr Glu Ser Asp Glu
            20                  25                  30

Val Glu Thr Asn Phe Val Ser Glu Gln Pro Ser Ser Tyr Tyr Ala Gln
        35                  40                  45

Leu Tyr Lys Gln Asn Gln Val His Gly Thr His Val Ile Lys Leu Gly
    50                  55                  60

Ser Leu Lys Ala Asn Asp Asp Ala Ala Arg Glu Ala Leu Gly Ala Trp
65                  70                  75                  80

Arg Gly Gly Leu Gln Ile Gly Gly Ile Thr Asp Ser Asn Ala Gln
                85                  90                  95

Glu Trp Ile Asp Gln Gly Ala Ser His Val Ile Val Thr Ser Trp Leu
            100                 105                 110

Phe Pro Glu Gly Gln Phe Ser Ile Glu Arg Leu Gln His Leu Ser Ser
        115                 120                 125

Leu Ile Gly Lys Glu Lys Leu Val Val Asp Leu Ser Cys Arg Arg Gln
    130                 135                 140

Glu Ile Asp Gly Ser Pro Gln Trp Val Ala Met Asn Lys Trp Gln
145                 150                 155                 160

Thr Leu Thr Ser Ser Val Leu Asp Arg Glu Phe Phe Gln Leu Leu Ser
                165                 170                 175

Gln Tyr Cys Asp Glu Phe Leu Val His Ala Ala Asp Val Glu Gly Leu
            180                 185                 190

Cys Gln Gly Ile Asp Gln Glu Leu Val Arg Lys Leu Ser Glu Trp Ser
        195                 200                 205

Asp Leu Pro Val Thr Tyr Ala Gly Gly Ala Arg Ser Ile Gln Asp Leu
    210                 215                 220

Glu Thr Val Lys His Leu Ser Asn Gly Lys Val Asp Leu Thr Phe Gly
225                 230                 235                 240

Ser Ala Leu Asn Ile Phe Gly Gly Asn Leu Val Lys Phe Glu Asp Cys
                245                 250                 255

Val Lys Trp Asn Lys Thr Gln
            260

<210> SEQ ID NO 21
<211> LENGTH: 261
<212> TYPE: PRT
<213> ORGANISM: Saccharomyces cerevisiae

<400> SEQUENCE: 21

Met Thr Lys Phe Ile Gly Cys Ile Asp Leu His Asn Gly Glu Val Lys
1               5                   10                  15

Gln Ile Val Gly Gly Thr Leu Thr Ser Lys Lys Glu Asp Val Pro Lys
            20                  25                  30

Thr Asn Phe Val Ser Gln His Pro Ser Ser Tyr Tyr Ala Lys Leu Tyr
        35                  40                  45

Lys Asp Arg Asp Val Gln Gly Cys His Val Ile Lys Leu Gly Pro Asn
    50                  55                  60

Asn Asp Asp Ala Ala Arg Glu Ala Leu Gln Glu Ser Pro Gln Phe Leu

| | | 65 | | | 70 | | | 75 | | | 80 | |
|---|---|---|---|---|---|---|---|---|---|---|---|---|

Gln Val Gly Gly Gly Ile Asn Asp Thr Asn Cys Leu Glu Trp Leu Lys
                     85                          90                     95

Trp Ala Ser Lys Val Ile Val Thr Ser Trp Leu Phe Thr Lys Glu Gly
              100                     105                     110

His Phe Gln Leu Lys Arg Leu Glu Arg Leu Thr Glu Leu Cys Gly Lys
              115                     120                     125

Asp Arg Ile Val Val Asp Leu Ser Cys Arg Lys Thr Gln Asp Gly Arg
    130                        135                     140

Trp Ile Val Ala Met Asn Lys Trp Gln Thr Leu Thr Asp Leu Glu Leu
145                   150                     155                     160

Asn Ala Asp Thr Phe Arg Glu Leu Arg Lys Tyr Thr Asn Glu Phe Leu
              165                     170                     175

Ile His Ala Ala Asp Val Glu Gly Leu Cys Gly Gly Ile Asp Glu Leu
                 180                     185                     190

Leu Val Ser Lys Leu Phe Glu Trp Thr Lys Asp Tyr Asp Asp Leu Lys
              195                     200                     205

Ile Val Tyr Ala Gly Gly Ala Lys Ser Val Asp Asp Leu Lys Leu Val
    210                        215                     220

Asp Glu Leu Ser His Gly Lys Val Asp Leu Thr Phe Gly Ser Ser Leu
225                   230                     235                     240

Asp Ile Phe Gly Gly Asn Leu Val Lys Phe Glu Asp Cys Cys Arg Trp
                 245                     250                     255

Asn Glu Lys Gln Gly
              260

<210> SEQ ID NO 22
<211> LENGTH: 49
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 22
ggatccctcg agagatcttt tttgtagaaa tgtcttggtg tcctcgtcc              49

<210> SEQ ID NO 23
<211> LENGTH: 58
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 23
gcatgcacta gtgcggccgc tgtgttttga tagttgttca attgattgaa atagggac      58

<210> SEQ ID NO 24
<211> LENGTH: 44
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 24
gctagcttaa ttaaacaggc ccctttttcct ttgtcgatat catg                    44

<210> SEQ ID NO 25

```
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcatgcggat cccttaagag ccggcagctt gcaaattaaa gccttcgagc gtccc            55

<210> SEQ ID NO 26
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gaattcggcc gatctggcct tccctgaatt tttacgtcca gc                         42

<210> SEQ ID NO 27
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gtttaaacgt cttcaatgac tgatatatac tttctacgct gg                         42

<210> SEQ ID NO 28
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gaattcggcc atctaggcca tgactggctt tgatgtcttg gac                        43

<210> SEQ ID NO 29
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gtttaaacgg actactggtt agtgggagat cgctgcgg                              38

<210> SEQ ID NO 30
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gagctcggcc agcttggccg ctaacagtaa caaaaactac cgccag                     46

<210> SEQ ID NO 31
<211> LENGTH: 43
```

```
<210> SEQ ID NO 31
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gtttaaacga cagccttctt tgggtcatga gtaacttcca aac                43

<210> SEQ ID NO 32
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gagctcggcc taactggccc tttgacgttt ctgacaatag ttc                43

<210> SEQ ID NO 33
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gtttaaacgc aaataatagt ctatcgttca agtgattcgc c                  41

<210> SEQ ID NO 34
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gaattcggcc aaaacggcct tcctcactgg tattatttct taggag             46

<210> SEQ ID NO 35
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gtttaaacgc atcaatagct agacgactaa aaccgccaga ac                 42

<210> SEQ ID NO 36
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gagctcggcc cgcaaggcca ttcacacttg aactagctac taacgg             46

<210> SEQ ID NO 37
<211> LENGTH: 47
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 37
gtttaaacga tactagctca aaaaaattgc aaattgtatg ttgtatg                47

<210> SEQ ID NO 38
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gaattcggcc gtattggcca tcaagtggta aatgcttgaa tcggaagc               48

<210> SEQ ID NO 39
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gtttaaaccg gactattttt ctatggtgga gcacttactc c                      41

<210> SEQ ID NO 40
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
atttaaatgg gactttaact caagtaaaag gatagttgta c                      41

<210> SEQ ID NO 41
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gcatgcggcc tatcaggcca ttccatccat ggataacagg aatg                   44

<210> SEQ ID NO 42
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
atttaaatga cgagatcaat tagaacctgt tttggcaata ac                     42

<210> SEQ ID NO 43
<211> LENGTH: 45
<212> TYPE: DNA
<213> ORGANISM: Artificial Sequence
```

<220> FEATURE:
<223> OTHER INFORMATION: Description of Artificial Sequence: Synthetic primer

<400> SEQUENCE: 43
gtcgacggcc tctgaggccg aagctgacct cgtagctgta tttcg            45

<210> SEQ ID NO 44
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
atttaaatca cggatttatg cttgatcaca tgaccaatca taac             44

<210> SEQ ID NO 45
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
gtcgacggcc gatggggccc gcattcttct tgcttaataa acc              43

<210> SEQ ID NO 46
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
atttaaatgg tgccagtgac attcttgtct ttgagatcag                  40

<210> SEQ ID NO 47
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
gtcgacggcc cagatggcca gagttgtaac caaatctctt attctcatac c     51

<210> SEQ ID NO 48
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
atttaaatca ggctaaataa atctaatcac gtattatagg cgagag           46

<210> SEQ ID NO 49
<211> LENGTH: 49
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 49
gtcgacggcc aaaatggcca tttatcagat taatgctata aaggtcatg                49

<210> SEQ ID NO 50
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
atttaaatct accacaggtt atcaaatcat ctacatagat aatc                     44

<210> SEQ ID NO 51
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gtcgacggcc ttagtggccc cactcacgga gtctaaaagt tgtc                     44

<210> SEQ ID NO 52
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
atttaaatga ttgctacctt agtttatagt taatagtaga ggg                      43

<210> SEQ ID NO 53
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gtcgacggcc aatctggcca ttcttttttg gcatccacct caaacc                   46

<210> SEQ ID NO 54
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gtttaaacca gttgagccag accgcgctaa acgcatacc                           39

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 55
gtttaaacga tgtcgtcact gtgtggtccg ctcc                                34

<210> SEQ ID NO 56
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
atttaaatgt gagcgatgag gagggcccac tgag                                34

<210> SEQ ID NO 57
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ctcgagggcc aaggaattct agagccatga cagc                                34

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
atttaaatgg gtgttatttt caagtaagag tcatttgagg                          40

<210> SEQ ID NO 59
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ctcgagcgga gccatctttc ttcttgcgga ttcgc                               35

<210> SEQ ID NO 60
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
atttaaatca agttgcgtcc ggtatacgta acgtctc                             37

<210> SEQ ID NO 61
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
agatctgcat caaaggacat ttatgtctct taacctgg                                    38

<210> SEQ ID NO 62
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
atttaaatcg attgctcatc ttcagaagaa gtcttcaaat g                                41

<210> SEQ ID NO 63
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ctcgagggtt gaagatatct ccatcaaata tggagtac                                    38

<210> SEQ ID NO 64
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
atttaaatgc aaaatgcttt ctggaactca agggtcttgt g                                41

<210> SEQ ID NO 65
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ctcgagccca aggatgacag cggtcatcca agtgagc                                     37

<210> SEQ ID NO 66
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ctattattgc cagcgacggc cgggac                                                 26

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 67
gtacaaacgc gtgtacgcat gtaac                                          25

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
cgttgagatt cagacaccaa aggaggagtc                                     30

<210> SEQ ID NO 69
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gccggtgtct caggaaactc tagatactg                                      29

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gtccgaagtc acagatagct catctcgaag                                     30

<210> SEQ ID NO 71
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ggttagggtg catattggtt aactggccc                                      29

<210> SEQ ID NO 72
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cgcggaagcg tagtcagaat acaaaccc                                       28

<210> SEQ ID NO 73
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
```
gttacaagag gtttcaacgg ctgtcgtatc                     30

<210> SEQ ID NO 74
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gcatcctatt aacgtaatct tctggcttct c                   31

<210> SEQ ID NO 75
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gggtgacatt gtggcagata gcaagagttg                     30

<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gtgcccggca gcattaagcc atccatcgtc                     30

<210> SEQ ID NO 77
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ggactcatat ggacaaaatc gagcaacgct c                   31

<210> SEQ ID NO 78
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cttcagtgtg ctccgggctg ccaaaagaag                     30

<210> SEQ ID NO 79
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79

-continued

```
gtttgaagag tcaccctagc cacaatgtac                              30

<210> SEQ ID NO 80
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80 gaaacccta aagcagaagt gcctccattg                               30

<210> SEQ ID NO 81
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gggtggttcc tcccaggtgg catacttgg                               29
```

US 7,479,389 B2

ARG1, ARG2, ARG3, HIS1, HIS2, HIS5, HIS6 GENES AND METHODS FOR STABLE GENETIC INTEGRATION

CROSS-REFERENCE TO RELATED APPLICATIONS

This application claims priority to U.S. provisional application Ser. No. 60/549,662 filed Mar. 2, 2004, which is incorporated by reference herein in its entirety.

FIELD OF THE INVENTION

This invention relates to novel genes isolated in yeast. The invention also relates to plasmids, which are particularly useful for stable genetic integration into the yeast genome. The present invention also relates to novel yeast strains in the expression of heterologous proteins and methods for generating novel host strains.

BACKGROUND OF THE INVENTION

Yeast strains, such as *Pichia pastoris*, are commonly used for the production of heterologous proteins. *P. pastoris* has become a popular model system for the study of peroxisome biogenesis (Gould et al., *Yeast* 8:613-628 (1992)), autophagy (Tuttle and Dunn, *J. Cell Sci.* 108:25-35 (1995); Sakai et al., *J. Cell Biol.* 141:625-636 (1998)) and the organization and biogenesis of the organelles of the secretory pathway (Rossanese et al., *J. Cell Biol.* 145:69-81 (1999)). The development of simple DNA transformation systems, (see Cregg et al., *Mol. Cell. Biol.* 5:3376-3385 (1985)) and the availability of selectable marker genes have been of great importance in conducting the above experiments. Currently, the biosynthetic marker genes ADE1, ARG4, HIS4 and URA3 are used in conjunction with the corresponding auxotrophic host strains to select for transformed cells. See Lin Cereghino et al., *Gene* 263:159-169 (2001). The use of dominant selectable markers to identify transformants is also possible, but markers are limited to the Sh ble gene from *Streptoalloteichus hindustanus*, which confers resistance to the drug Zeocin (Higgins et al., *Methods Mol. Biol.* 103:41-53 (1998)), and the blasticidin S deaminase gene from *Aspergillus terreus*, which confers resistance to the drug blasticidin (Kimura et al., *Mol. Gen. Genet.* 242:121-129 (1994)).

Stable integration of cloned DNA segments into the yeast genome through homologous recombination is well known in the art. See e.g., Orr-Weaver et al., *Proc. Natl. Acad. Sci. USA* 78:6364-6358 (1981). More recently, methods have been developed in *S. cerevisiae* to generate yeast strains containing DNA integrated at multiple unlinked sites by homologous recombination using molecular constructs containing the URA3 marker genes. See e.g., Alani et al., *Genetics* 116:541-545 (1987). In *Pichia pastoris*, yeast strains have been developed containing integrated DNA using constructs encoding the URA5 marker. See e.g., Nett and Gerngross, *Yeast* 20: 1279-1290 (2003).

Both the PpURA3 and the PpURA5 genes can be used repeatedly after counterselection on medium containing 5-fluoroorotic acid (5FOA). However, unlike ura auxotrophic strains in *Saccharomyces cerevisiae* (S.c.), the *P. pastoris* ura3 and ura5 auxotrophs have significantly reduced growth rates which are likely due to an inability of *P. pastoris* to take up uracil from the medium. See Lin Cereghino et al., *Gene* 263:159-169 (2001). These plasmid gene cassettes can potentially be reused indefinitely, however, another disadvantage of these as recyclable markers is the additional time required to recover the marker, thereby at least doubling the time necessary for one round of genetic modification.

Extensive genetic engineering projects, requiring the expression of several genes in parallel, necessitate the availability of counterselectable markers and plasmids for stable genetic integration of heterologous proteins into the host genome. Presently available auxotrophic strains of *P. pastoris* suffer the disadvantage of gene reversion. A high reversion rate decreases the usefulness of auxotrophic strains because revertant colonies are misidentified as false-positive transformants.

What is needed, therefore, is a method for stable genetic introduction of several heterologous genes into the genome of *Pichia pastoris* without the need for recyclable or multiple auxotrophic markers.

SUMMARY OF THE INVENTION

The present invention provides isolated polynucleotides comprising or consisting of nucleic acid sequences selected from the group consisting of the coding sequences of the *P. pastoris* ARG1, ARG2, ARG3, HIS1, HIS2, HIS5 and HIS6 genes; nucleic acid sequences that are degenerate variants of these sequences; and related nucleic acid sequences and fragments. The invention also provides vectors and host cells comprising the isolated polynucleotides.

The invention further provides isolated polypeptides comprising or consisting of polypeptide sequences selected from the group consisting of sequences encoded by the *P. pastoris* ARG1, ARG2, ARG3, HIS1, HIS2, HIS5 and HIS6 genes and related polypeptide sequences, fragments and fusions.

The invention also provides host cells comprising a disruption, deletion or mutation of a nucleic acid sequence selected from the group consisting of the coding sequence of the *P. pastoris* ARG1, ARG2, ARG3, HIS1, HIS2, HIS5 and HIS6 genes, a nucleic acid sequence that is a degenerate variant of the coding sequence of the *P. pastoris* ARG1, ARG2, ARG3, HIS1, HIS2, HIS5 and HIS6 genes and related nucleic acid sequences and fragments, in which the host cells have a reduced activity of the polypeptide encoded by the nucleic acid sequence compared to a host cell without the disruption, deletion or mutation.

The invention further provides methods for genetic integration of a heterologous nucleic acid sequence in a host cell. The methods include the step of disrupting a host gene encoding argininosuccinate synthase (ARG1), amino-acid N-acetyltransferase (ARG2), ornithine carbamoyltransferase (ARG3), ATP phosphoribosyltransferase (HIS1), histidinol-phosphatase (HIS2), histidinol-phosphatase transaminase (HIS5), or 1-[(5-phosphoribosyl-5-(5-phosphoribosylamino] imidazole 4-carboxamide isomerase (HIS6) by introduction of disrupted, deleted or mutated nucleic acid sequences of the *P. pastoris* ARG1, ARG2, ARG3, HIS1, HIS2, HIS5 and HIS6 genes, nucleic acid sequences that are degenerate variants of the coding sequences of the *P. pastoris* ARG1, ARG2, ARG3, HIS1, HIS2, HIS5 and HIS6 genes and/or related nucleic acid sequences and fragments. In addition, the invention provides methods for the genetic integration of a heterologous nucleic acid sequence in a host cell lacking ARG1, ARG2, ARG3, HIS1, HIS2, HIS5 and HIS6 activities. The methods comprise the step of introducing a sequence or gene of interest into a host cell linked with a sequence encoding ARG1, ARG2, ARG3, HIS1, HIS2, HIS5 and HIS6 activities selected from the group consisting of the coding sequence of the *P. pastoris* ARG1, ARG2, ARG3, HIS1, HIS2, HIS5 and HIS6 genes.

BRIEF DESCRIPTION OF THE DRAWINGS

FIG. 1 (A) shows the open reading frame (ORF) of *P. pastoris* ARG1 (Genbank: AY532165) (SEQ ID NO: 1) and the amino acid sequence. (B) shows the amino acid alignment of P.p. ARG1 (SEQ ID NO: 2) with S.c. ARG1 (SEQ ID NO: 3).

FIG. 2 (A) shows the open reading frame (ORF) of *P. pastoris* ARG2 (Genbank: AY532166) (SEQ ID NO: 4) and the amino acid sequence. (B) shows the amino acid alignment of P.p. ARG2 (SEQ ID NO: 5) with S.c. ARG2 (SEQ ID NO: 6)

FIG. 3 (A) shows the open reading frame (ORF) of *P. pastoris* ARG3 (Genbank: AY532167) (SEQ ID NO: 7) and the amino acid sequence. (B) shows the amino acid alignment of P.p. ARG3 (SEQ ID NO: 8) with S.c. ARG3 (SEQ ID NO: 9).

FIG. 4 (A) shows the open reading frame (ORF) of *P. pastoris* HIS1 (Genbank: AY532168) (SEQ ID NO: 10) and the amino acid sequence. (B) shows the amino acid alignment of P.p. HIS1 (SEQ ID NO: 11) with S.c. HIS1 (SEQ ID NO: 12).

FIG. 5 (A) shows the open reading frame (ORF) of *P. pastoris* HIS2 (Genbank: AY532169) (SEQ ID NO: 13) and the amino acid sequence. (B) shows the amino acid alignment of P.p. HIS2 (SEQ ID NO: 14) with S.c. HIS2 (SEQ ID NO: 15).

FIG. 6 (A) shows the open reading frame (ORF) of *P. pastoris* HIS5 (Genbank: AY532170) (SEQ ID NO: 16) and the amino acid sequence. (B) shows the amino acid alignment of P.p. HIS5 (SEQ ID NO: 17) with S.c. HIS5 (SEQ ID NO: 18).

FIG. 7 (A) shows the open reading frame (ORF) of *P. pastoris* HIS6 (Genbank: AY532171) (SEQ ID NO: 19) and the amino acid sequence. (B) shows the amino acid alignment of P.p. HIS6 (SEQ ID NO: 20) with S.c. HIS6 (SEQ ID NO: 21).

FIG. 8 (A) shows the common structural elements of the disruption vectors derived from plasmid pJN653 and (B) shows the common structural elements of the knock-in vectors.

DETAILED DESCRIPTION OF THE INVENTION

Figure 9:
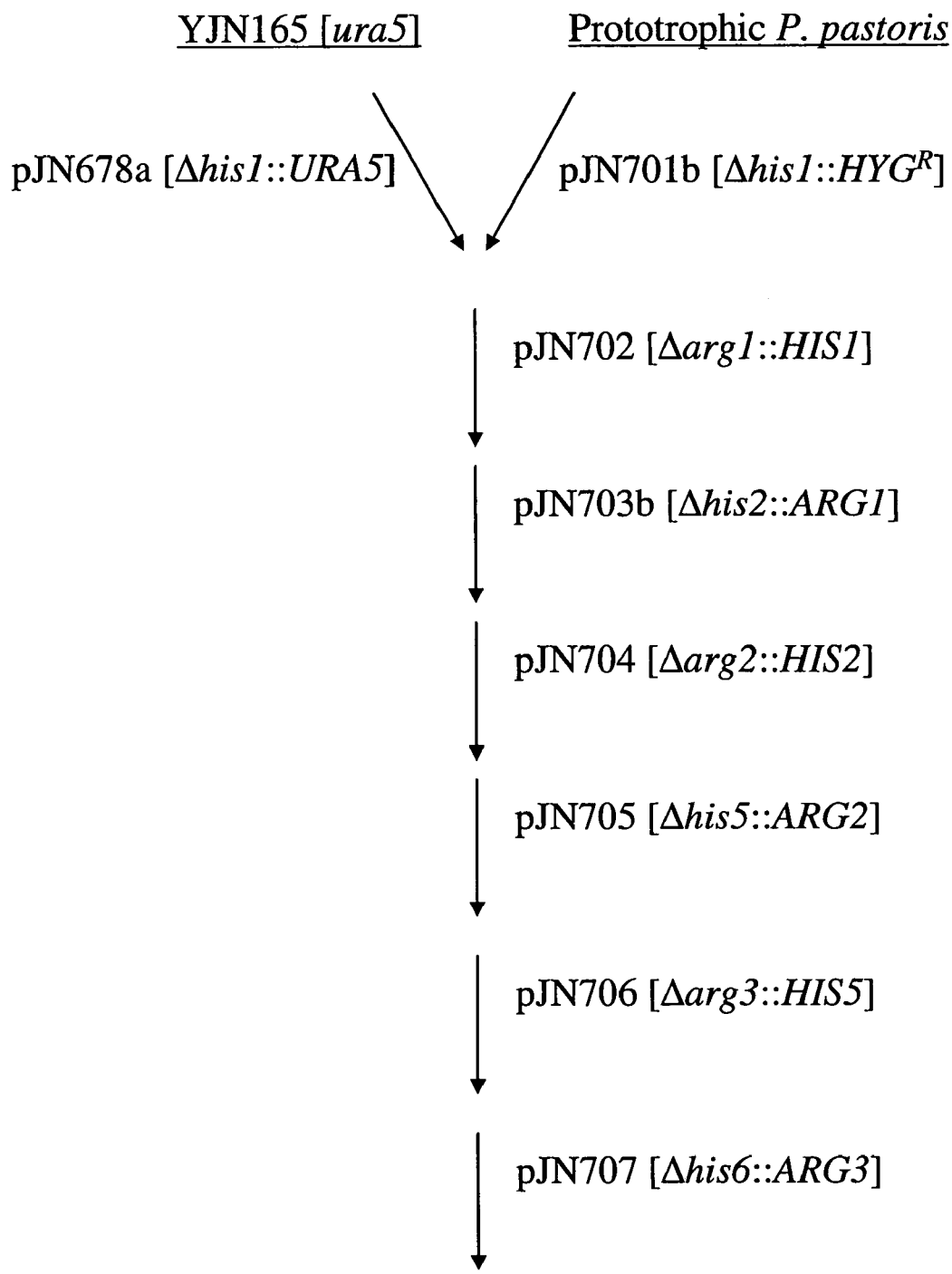
FIG. 9 outlines the strategy presented in the present invention for enabling the consecutive use of the ARG1, ARG2, ARG3, HIS1, HIS2, HIS5 and HIS6 cloned genes as auxotrophic markers.

Unless otherwise defined herein, scientific and technical terms used in connection with the present invention shall have the meanings that are commonly understood by those of ordinary skill in the art. Further, unless otherwise required by context, singular terms shall include the plural and plural terms shall include the singular. In general, nomenclatures used in connection with the techniques of biochemistry, enzymology, molecular and cellular biology, microbiology, genetics, protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. *Molecular Cloning: A Laboratory Manual*, 2d ed., Cold Spring Harbor Laboratory Press, Cold Spring Harbor, N.Y. (1989); Ausubel et al., *Current Protocols in Molecular Biology*, Greene Publishing Associates (1992, and Supplements to 2002); Harlow and Lane, *Antibodies: A Laboratory Manual*, Cold Spring Harbor Laboratory Press, Cold Spring Harbor, N.Y. (1990); Taylor and Drickamer, *Introduction to Glycobiology*, Oxford Univ. Press (2003); *Worthington Enzyme Manual*, Worthington Biochemical Corp., Freehold, N.J.; *Handbook of Biochemistry: Section A Proteins*, Vol I, CRC Press (1976); *Handbook of Biochemistry: Section A Proteins*, Vol II, CRC Press (1976); *Essentials of Glycobiology*, Cold Spring Harbor Laboratory Press (1999).

All publications, patents and other references mentioned herein are hereby incorporated by reference in their entireties.

The following terms, unless otherwise indicated, shall be understood to have the following meanings:

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation.

Unless otherwise indicated, a "nucleic acid comprising SEQ ID NO:X" refers to a nucleic acid, at least a portion of which has either (i) the sequence of SEQ ID NO:X, or (ii) a sequence complementary to SEQ ID NO:X. The choice between the two is dictated by the context. For instance, if the nucleic acid is used as a probe, the choice between the two is dictated by the requirement that the probe be complementary to the desired target.

An "isolated" or "substantially pure" nucleic acid or polynucleotide (e.g., an RNA, DNA or a mixed polymer) is one which is substantially separated from other cellular components that naturally accompany the native polynucleotide in its natural host cell, e.g., ribosomes, polymerases and genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, or (4) does not occur in nature. The term "isolated" or "substantially pure" can also be used in reference to recombinant or cloned DNA isolates, chemically synthesized polynucleotide analogs, or polynucleotide analogs that are biologically synthesized by heterologous systems.

However, "isolated" does not necessarily require that the nucleic acid or polynucleotide so described has itself been physically removed from its native environment. For instance, an endogenous nucleic acid sequence in the genome of an organism is deemed "isolated" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "isolated" because it is separated from at least some of the sequences that naturally flank it.

A nucleic acid is also considered "isolated" if it contains any modifications that do not naturally occur to the corresponding nucleic acid in a genome. For instance, an endogenous coding sequence is considered "isolated" if it contains an insertion, deletion or a point mutation introduced artificially, e.g., by human intervention. An "isolated nucleic acid" also includes a nucleic acid integrated into a host cell chromosome at a heterologous site and a nucleic acid construct present as an episome. Moreover, an "isolated nucleic acid" can be substantially free of other cellular material, or substantially free of culture medium when produced by recombinant techniques, or substantially free of chemical precursors or other chemicals when chemically synthesized.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, *Methods Enzymol.* 183:63-98 (1990) (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 50%, more preferably 60% of the nucleotide bases, usually at least about 70%, more usually at least about 80%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., *Molecular Cloning: A Laboratory Manual*, 2d ed., Cold Spring Harbor Laboratory Press, Cold Spring Harbor, N.Y. (1989), page 9.51, hereby incorporated by reference. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

The nucleic acids (also referred to as polynucleotides) of this invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product; see, e.g., Leung et al., *Technique*, 1:11-15 (1989) and Caldwell and Joyce, *PCR Methods Applic.* 2:28-33 (1992)); and "oligonucleotide-directed mutagenesis" (a process which enables the generation of site-specific mutations in any cloned DNA segment of interest; see, e.g., Reidhaar-Olson and Sauer, *Science* 241:53-57 (1988)).

The term "vector" as used herein is intended to refer to a nucleic acid molecule capable of transporting another nucleic acid to which it has been linked. One type of vector is a "plasmid", which refers to a circular double stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply, "expression vectors").

As used herein, the term "sequence of interest" or "gene of interest" refers to a nucleic acid sequence, typically encoding a protein, which is not normally produced in the host cell. The methods disclosed herein allow one or more sequences of interest or genes of interest to be stably integrated into a host cell genome. Non-limiting examples of sequences of interest include sequences encoding one or more polypeptides having an enzymatic activity, e.g., an enzyme which affects N-glycan synthesis in a host such as mannosyltransferases, N-acetylglucosaminyltransferases, UDP-N-acetylglucosamine transporters, galactosyltransferases and sialyltransferases. Still other sequences encode proteins of interest such as kringle domains of the human plasminogen, erythropoietin, cytokines such as interferon-α, interferon-β, interferon-γ, interferon-ω, and granulocyte-CSF, coagulation factors such as factor VIII, factor IX, and human protein C, soluble IgE receptor α-chain, IgG, IgG fragments, IgM, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1 antitrypsin, DNase II and α-feto proteins.

The term "marker sequence" or "marker gene" refers to a nucleic acid sequence capable of expressing an activity that allows either positive or negative selection for the presence or absence of the sequence within a host cell. For example, the *P. pastoris* URA5 gene is a marker gene because its presence can be selected for by the ability of cells containing the gene to grow in the absence of uracil. Its presence can also be selected against by the inability of cells containing the gene to grow in the presence of 5-FOA. Marker sequences or genes do not necessarily need to display both positive and negative selectability. Markers include dominant selectable markers that confer resistance to antibiotic such as HYG, nutritional markers that enable growth of cells on special media and auxotrophic markers. Pronk, Appl Environ Microbiol. 2002 May; 68(5): 2095-2100. Non-limiting examples of marker sequences or genes from *P. pastoris* include ADE1, ARG4, HIS4 and URA3.

"Operatively linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities. The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

The term "polypeptide fragment" as used herein refers to a polypeptide that has a deletion, e.g., an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "modified derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, and various enzymatic modifications, as will be readily appreciated by those skilled in the art. A variety of methods for labeling polypeptides and of substituents or labels useful for such purposes are well known in the art, and include radioactive isotopes such as $^{125}$I, $^{32}$P, $^{35}$S, and $^3$H, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al., *Current Protocols in Molecular Biology*, Greene Publishing Associates (1992, and Supplements to 2002) (hereby incorporated by reference).

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusions that include the entirety of the proteins of the present invention have particular utility. The heterologous polypeptide included within the fusion protein of the present invention is at least 6 amino acids in length, often at least 8 amino acids in length, and usefully at least 15, 20, and 25 amino acids in length. Fusions that include larger polypeptides, such as an IgG Fc region, and even entire proteins, such as the green fluorescent protein ("GFP") chromophore-containing proteins, have particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

The term "non-peptide analog" refers to a compound with properties that are analogous to those of a reference polypeptide. A non-peptide compound may also be termed a "peptide mimetic" or a "peptidomimetic". See, e.g., Jones, *Amino Acid and Peptide Synthesis*, Oxford University Press (1992); Jung, *Combinatorial Peptide and Nonpeptide Libraries: A Handbook*, John Wiley (1997); Bodanszky et al., *Peptide Chemistry—A Practical Textbook*, Springer Verlag (1993); *Synthetic Peptides: A Users Guide*, (Grant, ed., W. H. Freeman and Co., 1992); Evans et al., *J. Med. Chem.* 30:1229 (1987); Fauchere, *J. Adv. Drug Res.* 15:29 (1986); Veber and Freidinger, *Trends Neurosci.*, 8:392-396 (1985); and references sited in each of the above, which are incorporated herein by reference. Such compounds are often developed with the aid of computerized molecular modeling. Peptide mimetics that are structurally similar to useful peptides of the invention may be used to produce an equivalent effect and are therefore envisioned to be part of the invention.

A "polypeptide mutant" or "mutein" refers to a polypeptide whose sequence contains an insertion, duplication, deletion, rearrangement or substitution of one or more amino acids compared to the amino acid sequence of a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. A mutein may have the same but preferably has a different biological activity compared to the naturally-occurring protein.

A mutein has at least 65% overall sequence homology to its wild-type counterpart. Even more preferred are muteins having at least 70%, 75%, 80%, 85% or 90% overall sequence homology to the wild-type protein. In an even more preferred embodiment, a mutein exhibits at least 95% sequence identity, even more preferably 98%, even more preferably 99% and even more preferably 99.9% overall sequence identity. Sequence homology may be measured by any common sequence analysis algorithm, such as Gap or Bestfit.

Amino acid substitutions can include those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the twenty conventional amino acids and their abbreviations follow conventional usage. See *Immunology—A Synthesis* (Golub and Gren eds., Sinauer Associates, Sunderland, Mass., 2$^{nd}$ ed. 1991), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, N-methylarginine, and other similar amino acids and imino acids (e.g., 4-hydroxyproline). In the polypeptide notation used herein, the left-hand end corresponds to the amino terminal end and the right-hand end corresponds to the carboxy-terminal end, in accordance with standard usage and convention.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences.) In a preferred embodiment, a homologous protein is one that exhibits at least 65% sequence homology to the wild type protein, more preferred is at least 70% sequence homology. Even more preferred are homologous proteins that exhibit at least 75%, 80%, 85% or 90% sequence homology to the wild type protein. In a yet more preferred embodiment, a homologous protein exhibits at least 95%, 98%, 99% or 99.9% sequence identity. As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, *Methods Mol. Biol.* 24:307-31 and 25:365-89 (herein incorporated by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

A preferred algorithm when comparing a particular polypeptide sequence to a database containing a large number of sequences from different organisms is the computer program BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, *Methods Enzymol.* 183:63-98 (1990) (herein incorporated by reference). For example, percent sequence identity between amino acid sequences can be determined using FASTA with its default parameters (a word size of 2 and the PAM250 scoring matrix), as provided in GCG Version 6.1, herein incorporated by reference.

The term "region" as used herein refers to a physically contiguous portion of the primary structure of a biomolecule. In the case of proteins, a region is defined by a contiguous portion of the amino acid sequence of that protein.

The term "domain" as used herein refers to a structure of a biomolecule that contributes to a known or suspected function of the biomolecule. Domains may be co-extensive with regions or portions thereof; domains may also include distinct, non-contiguous regions of a biomolecule. Examples of protein domains include, but are not limited to, an Ig domain, an extracellular domain, a transmembrane domain, and a cytoplasmic domain.

As used herein, the term "molecule" means any compound, including, but not limited to, a small molecule, peptide, protein, sugar, nucleotide, nucleic acid, lipid, etc., and such a compound can be natural or synthetic.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Throughout this specification and claims, the word "comprise" or variations such as "comprises" or "comprising ", will be understood to imply the inclusion of a stated integer or group of integers but not the exclusion of any other integer or group of integers.

Nucleic Acid Sequences

The present invention provides isolated nucleic acid molecules that include the ARG1, ARG2, ARG3, HIS1, HIS, HIS5 and HIS6 genes from *P. pastoris* and variants thereof. The full-length nucleic acid sequence for these genes, which encode for the enzymes argininosuccinate synthase (ARG1) (SEQ ID NO: 1), amino-acid N-acetyltransferase (ARG2) (SEQ ID NO: 4), ornithine carbamoyltransferase (ARG3) (SEQ ID NO: 7), ATP phosphoribosyltransferase (HIS1)

(SEQ ID NO: 10), histidinol-phosphatase (HIS2) (SEQ ID NO: 13), histidinol-phosphatase transaminase (HIS5) (SEQ ID NO: 16), 1-[(5-phosphoribosyl-5-(5-phosphoribosylamino]imidazole 4-carboxamide isomerase (HIS6) (SEQ ID NO: 19), have been identified and sequenced as set forth in FIGS. 1-7. The encoded amino acid sequences are also set forth in FIGS. 1-7. These ARG1, ARG2, ARG3, HIS1, HIS2, HIS5, HIS6 genes (SEQ ID NOS: 1, 4, 7, 10, 13, 16, and 19, respectively) are particularly useful as selectable markers.

Provided herein are nucleic acid molecules capable of promoting the stable genetic integration of heterologous genes (i.e. genes of interest) into a host genome. The combination of these ARG1, ARG2, ARG3, HIS1, HIS2, HIS5, or HIS6 markers (SEQ ID NOS: 1, 4, 7, 10, 13, 16, or 19, respectively) and nucleic acids capable of promoting stable genetic integration enables extensive strain modification. It will be readily apparent to a skilled artisan that the repeated use of the methods disclosed herein allows multiple genes to be disrupted in various loci and further allows the insertion at these sites of any gene or genes of interest. Genes inserted by the disclosed approaches become stably integrated at a selected region in the genomic DNA of the host cells.

In one embodiment, the invention provides an isolated nucleic acid molecule having a nucleic acid sequence comprising or consisting of a wild-type *P. pastoris* ARG1 coding sequence (SEQ ID NO: 1), and homologs, variants and derivatives thereof. The invention also provides a nucleic acid molecule comprising or consisting of a sequence which is a degenerate variant of the wild-type *P. pastoris* ARG1 gene. In a further embodiment, the invention provides a nucleic acid molecule comprising or consisting of a sequence which is a variant of the *P. pastoris* ARG1 gene (SEQ ID NO: 1) having at least 65% identity to the wild-type gene. The nucleic acid sequence can preferably have at least 70%, 75% or 80% identity to the wild-type gene. Even more preferably, the nucleic acid sequence can have 85%, 90%, 95%, 98%, 99.9% or even higher identity to the wild-type gene.

In another embodiment, the nucleic acid molecule of the invention encodes a polypeptide having the amino acid sequence of SEQ ID NO:2. Also provided is a nucleic acid molecule encoding a polypeptide sequence that is at least 65% identical to SEQ ID NO:2. Typically the nucleic acid molecule of the invention encodes a polypeptide sequence of at least 70%, 75% or 80% identity to SEQ ID NO:2. Preferably, the encoded polypeptide is 85%, 90% or 95% identical to SEQ ID NO:2, and the identity can even more preferably be 98%, 99%, 99.9% or even higher.

In one embodiment, the invention provides an isolated nucleic acid molecule having a nucleic acid sequence comprising or consisting of a wild-type *P. pastoris* ARG2 coding sequence (SEQ ID NO:4), and homologs, variants and derivatives thereof. The invention also provides a nucleic acid molecule comprising or consisting of a sequence which is a degenerate variant of the wild-type *P. pastoris* ARG2 gene (SEQ ID NO:4). In a further embodiment, the invention provides a nucleic acid molecule comprising or consisting of a sequence which is a variant of the *P. pastoris* ARG2 (SEQ ID NO:4) gene having at least 65% identity to the wild-type gene. The nucleic acid sequence can preferably have at least 70%, 75% or 80% identity to the wild-type gene. Even more preferably, the nucleic acid sequence can have 85%, 90%, 95%, 98%, 99.9% or even higher identity to the wild-type gene.

In another embodiment, the nucleic acid molecule of the invention encodes a polypeptide having the amino acid sequence of SEQ ID NO:5. Also provided is a nucleic acid molecule encoding a polypeptide sequence that is at least 65% identical to SEQ ID NO:5. Typically the nucleic acid molecule of the invention encodes a polypeptide sequence of at least 70%, 75% or 80% identity to SEQ ID NO:5. Preferably, the encoded polypeptide is 85%, 90% or 95% identical to SEQ ID NO:5, and the identity can even more preferably be 98%, 99%, 99.9% or even higher.

In one embodiment, the invention provides an isolated nucleic acid molecule having a nucleic acid sequence comprising or consisting of a wild-type *P. pastoris* ARG3 coding sequence (SEQ ID NO:7), and homologs, variants and derivatives thereof. The invention also provides a nucleic acid molecule comprising or consisting of a sequence which is a degenerate variant of the wild-type *P. pastoris* ARG3 gene (SEQ ID NO: 7). In a further embodiment, the invention provides a nucleic acid molecule comprising or consisting of a sequence which is a variant of the *P. pastoris* ARG3 gene (SEQ ID NO: 7) having at least 65% identity to the wild-type gene. The nucleic acid sequence can preferably have at least 70%, 75% or 80% identity to the wild-type gene. Even more preferably, the nucleic acid sequence can have 85%, 90%, 95%, 98%, 99.9% or even higher identity to the wild-type gene.

In another embodiment, the nucleic acid molecule of the invention encodes a polypeptide having the amino acid sequence of SEQ ID NO:8. Also provided is a nucleic acid molecule encoding a polypeptide sequence that is at least 65% identical to SEQ ID NO:8. Typically the nucleic acid molecule of the invention encodes a polypeptide sequence of at least 70%, 75% or 80% identity to SEQ ID NO:8. Preferably, the encoded polypeptide is 85%, 90% or 95% identical to SEQ ID NO:8, and the identity can even more preferably be 98%, 99%, 99.9% or even higher.

In one embodiment, the invention provides an isolated nucleic acid molecule having a nucleic acid sequence comprising or consisting of a wild-type *P. pastoris* HIS1 coding sequence (SEQ ID NO: 10), and homologs, variants and derivatives thereof. The invention also provides a nucleic acid molecule comprising or consisting of a sequence which is a degenerate variant of the wild-type *P. pastoris* HIS1 gene (SEQ ID NO: 10). In a further embodiment, the invention provides a nucleic acid molecule comprising or consisting of a sequence which is a variant of the *P. pastoris* HIS1 gene (SEQ ID NO: 10) having at least 65% identity to the wild-type gene. The nucleic acid sequence can preferably have at least 70%, 75% or 80% identity to the wild-type gene. Even more preferably, the nucleic acid sequence can have 85%, 90%, 95%, 98%, 99.9% or even higher identity to the wild-type gene.

In another embodiment, the nucleic acid molecule of the invention encodes a polypeptide having the amino acid sequence of SEQ ID NO: 11. Also provided is a nucleic acid molecule encoding a polypeptide sequence that is at least 65% identical to SEQ ID NO: 11. Typically the nucleic acid molecule of the invention encodes a polypeptide sequence of at least 70%, 75% or 80% identity to SEQ ID NO: 11. Preferably, the encoded polypeptide is 85%, 90% or 95% identical to SEQ ID NO: 11, and the identity can even more preferably be 98%, 99%, 99.9% or even higher.

In one embodiment, the invention provides an isolated nucleic acid molecule having a nucleic acid sequence comprising or consisting of a wild-type *P. pastoris* HIS2 coding sequence (SEQ ID NO:13), and homologs, variants and derivatives thereof. The invention also provides a nucleic acid molecule comprising or consisting of a sequence which is a degenerate variant of the wild-type *P. pastoris* HIS2 gene (SEQ ID NO: 13). In a further embodiment, the invention provides a nucleic acid molecule comprising or consisting of a sequence which is a variant of the *P. pastoris* HIS2 gene (SEQ ID NO: 13) having at least 65% identity to the wild-type gene. The nucleic acid sequence can preferably have at least 70%, 75% or 80% identity to the wild-type gene. Even more preferably, the nucleic acid sequence can have 85%, 90%, 95%, 98%, 99.9% or even higher identity to the wild-type gene.

In another embodiment, the nucleic acid molecule of the invention encodes a polypeptide having the amino acid sequence of SEQ ID NO: 14. Also provided is a nucleic acid molecule encoding a polypeptide sequence that is at least 65% identical to SEQ ID NO: 14. Typically the nucleic acid molecule of the invention encodes a polypeptide sequence of at least 70%, 75% or 80% identity to SEQ ID NO: 14. Preferably, the encoded polypeptide is 85%, 90% or 95% identical to SEQ ID NO: 14, and the identity can even more preferably be 98%, 99%, 99.9% or even higher.

In one embodiment, the invention provides an isolated nucleic acid molecule having a nucleic acid sequence comprising or consisting of a wild-type *P. pastoris* HIS5 coding sequence (SEQ ID NO: 16), and homologs, variants and derivatives thereof. The invention also provides a nucleic acid molecule comprising or consisting of a sequence which is a degenerate variant of the wild-type *P. pastoris* HIS5 gene (SEQ ID NO: 16). In a further embodiment, the invention provides a nucleic acid molecule comprising or consisting of a sequence which is a variant of the *P. pastoris* HIS5 gene (SEQ ID NO: 16) having at least 65% identity to the wild-type gene. The nucleic acid sequence can preferably have at least 70%, 75% or 80% identity to the wild-type gene. Even more preferably, the nucleic acid sequence can have 85%, 90%, 95%, 98%, 99.9% or even higher identity to the wild-type gene.

In another embodiment, the nucleic acid molecule of the invention encodes a polypeptide having the amino acid sequence of SEQ ID NO: 17. Also provided is a nucleic acid molecule encoding a polypeptide sequence that is at least 65% identical to SEQ ID NO: 17. Typically the nucleic acid molecule of the invention encodes a polypeptide sequence of at least 70%, 75% or 80% identity to SEQ ID NO:17. Preferably, the encoded polypeptide is 85%, 90% or 95% identical to SEQ ID NO: 17, and the identity can even more preferably be 98%, 99%, 99.9% or even higher.

In one embodiment, the invention provides an isolated nucleic acid molecule having a nucleic acid sequence comprising or consisting of a wild-type *P. pastoris* HIS6 coding sequence (SEQ ID NO:19), and homologs, variants and derivatives thereof. The invention also provides a nucleic acid molecule comprising or consisting of a sequence which is a degenerate variant of the wild-type *P. pastoris* HIS6 gene (SEQ ID NO: 19). In a further embodiment, the invention provides a nucleic acid molecule comprising or consisting of a sequence which is a variant of the *P. pastoris* HIS6 gene (SEQ ID NO: 19) having at least 65% identity to the wild-type gene. The nucleic acid sequence can preferably have at least 70%, 75% or 80% identity to the wild-type gene. Even more preferably, the nucleic acid sequence can have 85%, 90%, 95%, 98%, 99.9% or even higher identity to the wild-type gene.

In another embodiment, the nucleic acid molecule of the invention encodes a polypeptide having the amino acid sequence of SEQ ID NO:20. Also provided is a nucleic acid molecule encoding a polypeptide sequence that is at least 65% identical to SEQ ID NO:20. Typically the nucleic acid molecule of the invention encodes a polypeptide sequence of at least 70%, 75% or 80% identity to SEQ ID NO:20. Preferably, the encoded polypeptide is 85%, 90% or 95% identical to SEQ ID NO:20, and the identity can even more preferably be 98%, 99%, 99.9% or even higher.

The invention also provides nucleic acid molecules that hybridize under stringent conditions to the above-described nucleic acid molecules. As defined above, and as is well known in the art, stringent hybridizations are performed at about 25° C. below the thermal melting point ($T_m$) for the specific DNA hybrid under a particular set of conditions, where the $T_m$ is the temperature at which 50% of the target sequence hybridizes to a perfectly matched probe. Stringent washing is performed at temperatures about 5° C. lower than the $T_m$ for the specific DNA hybrid under a particular set of conditions.

Nucleic acid molecules comprising a fragment of any of the above-described nucleic acid sequences are also provided. These fragments preferably contain at least 20 contiguous nucleotides. More preferably the fragments of the nucleic acid sequences contain at least 25, 30, 35, 40, 45, 50, 60, 70, 80, 90, 100 or even more contiguous nucleotides.

The nucleic acid sequence fragments of the present invention display utility in a variety of systems and methods. For example, the fragments may be used as probes in various hybridization techniques. Depending on the method, the target nucleic acid sequences may be either DNA or RNA. The target nucleic acid sequences may be fractionated (e.g., by gel electrophoresis) prior to the hybridization, or the hybridization may be performed on samples in situ. One of skill in the art will appreciate that nucleic acid probes of known sequence find utility in determining chromosomal structure (e.g., by Southern blotting) and in measuring gene expression (e.g., by Northern blotting). In such experiments, the sequence fragments are preferably detectably labeled, so that their specific hybridization to target sequences can be detected and optionally quantified. One of skill in the art will appreciate that the nucleic acid fragments of the present invention may be used in a wide variety of blotting techniques not specifically described herein.

It should also be appreciated that the nucleic acid sequence fragments disclosed herein also find utility as probes when immobilized on microarrays. Methods for creating microarrays by deposition, fixation and/or immobilization of nucleic acids onto support substrates are well known in the art. A method for immobilization on membranes is detailed in Springer et al., *J. Biomol Tech,* 14, 183-190, (2003). A review of microarrays and related techniques is detailed in *DNA Microarrays: A Practical Approach* (*Practical Approach Series*), Schena (ed.), Oxford University Press (1999) (ISBN: 0199637768); *Nature Genet.* 21(1) (suppl): 1-60 (1999); *Microarray Biochip: Tools and Technology*, Schena (ed.), Eaton Publishing Company/BioTechniques Books Division (2000) (ISBN: 1881299376), the disclosures of which are incorporated herein by reference in their entireties. For example, analysis of gene expression using microarrays comprising nucleic acid sequence fragments, such as the nucleic acid sequence fragments disclosed herein, is a well-established utility for sequence fragments in the field of cell and molecular biology. Other uses for sequence fragments immobilized on microarrays are described in Gerhold et al., *Trends Biochem. Sci.* 24:168-173 (1999) and Zweiger, *Trends Biotechnol.* 17:429-436 (1999); *DNA Microarrays: A Practical Approach* (*Practical Approach Series*), Schena (ed.), Oxford University Press (1999) (ISBN: 0199637768); *Nature Genet.* 2 1(1)(suppl): 1-60 (1999); *Microarray Biochip: Tools and Technology*, Schena (ed.), Eaton Publishing Company/Bio-Techniques Books Division (2000) (ISBN: 1881299376), the disclosures of each of which is incorporated herein by reference in its entirety.

The invention provides recombinant DNA molecules comprising a cassette containing the *P. pastoris* ARG1, ARG2, ARG3, HIS1, HIS2, HIS5, or HIS6 genes (SEQ ID NOS: 1, 4, 7, 10, 13, 16, or 19, respectively), or a homolog, variant or derivative thereof. In order to make use of these arginine and histidine biosynthesis genes, it was essential to clone each of the seven genes. The *P. pastoris* orthologues (SEQ ID NOS: 2, 5, 8, 11, 14, 17, or 20, respectively) to the *S. cerevisiae* ARG1, ARG2, ARG3, HIS1, HIS2, HIS5 and HIS6 (SEQ ID NOS: 3, 6, 9, 12, 15, 18, or 21, respectively) were cloned by comparison of the translations of the respective *S. cerevisiae* open reading frames to a partial *P. pastoris* genomic sequence provided by Integrated Genomics Inc. using the BLAST program (Altschul et al., *J. Mol. Biol.* 215: 403-410 (1990)). (Example 1).

Vectors

Also provided are vectors, including expression vectors, which comprise the above nucleic acid molecules of the invention, as described further herein. In a first embodiment, the vectors include the isolated nucleic acid molecules described above. In an alternative embodiment, the vectors of the invention include the above-described nucleic acid molecules operably linked to one or more expression control sequences. The vectors of the present invention may thus be used to express a polypeptide having any of the following activities: argininosuccinate synthase (ARG1), amino-acid N-acetyltransferase (ARG2), ornithine carbamoyltransferase (ARG3), ATP phosphoribosyltransferase (HIS1), histidinol-phosphatase (HIS2), histidinol-phosphatase transaminase (HIS5), 1-[(5-phosphoribosyl-5-(5-phosphoribosylamino]imidazole 4-carboxamide isomerase (HIS6).

The vectors of the invention may also include an element which ensures that they are stably maintained at a single copy in each cell (e.g., a centromere-like sequence such as "CEN"). Alternatively, the autonomously replicating vector may optionally comprise an element which enables the vector to be replicated to higher than one copy per host cell (e.g., an autonomously replicating sequence or "ARS"). *Methods in Enzymology*, Vol. 350: *Guide to yeast genetics and molecular and cell biology*, Part B., Guthrie and Fink (eds.), Academic Press (2002).

In a preferred embodiment of the invention, the vectors are non-autonomously replicating, integrative vectors designed to function as gene disruption or replacement cassettes. An example of an integrative vector of this type comprises at least at portion of a heterologous target gene linked to *P. pastoris* argininosuccinate synthase (ARG1) (SEQ ID NO: 1), amino-acid N-acetyltransferase (ARG2) (SEQ ID NO: 4), ornithine carbamoyltransferase (ARG3) (SEQ ID NO: 7), ATP phosphoribosyltransferase (HIS1) (SEQ ID NO: 10), histidinol-phosphatase (HIS2) (SEQ ID NO: 13), histidinol-phosphatase transaminase (HIS5) (SEQ ID NO: 16), or 1-[(5-phosphoribosyl-5-(5-phosphoribosylamino]imidazole 4-carboxamide isomerase (HIS6) (SEQ ID NO: 19)-encoding sequences. The vectors thus allow the targeted integration of the sequences to be selected for by the expression of ARG1, ARG2, ARG3, HIS1, HIS2, HIS5 or HIS6 activity in cells carrying the integrated vectors.

In other embodiments, the integrative vectors of the invention may include additionally heterologous sequences encoding proteins having desirable properties, e.g., those encoding glycosylation enzymes, so that the desired sequences can be introduced into the host cell genome as a result of the integration.

Isolated Polypeptides

According to another aspect of the invention, isolated polypeptides (including muteins, allelic variants, fragments, derivatives, and analogs) encoded by the nucleic acid molecules of the invention are provided. In one embodiment, the isolated polypeptide comprises the polypeptide sequence corresponding to SEQ ID NOs: 2, 5, 8, 11, 14, 17, or 20. In an alternative embodiment of the invention, the isolated polypeptide comprises a polypeptide sequence at least 65% identical to SEQ ID NOs: 2, 5, 8, 11, 14, 17, or 20. Preferably the isolated polypeptide of the invention has at least 70%, 75% or 80% identity to SEQ ID NOs: 2, 5, 8, 11, 14, 17, or 20. More preferably, the identity is 85%, 90% or 95%, but the identity to SEQ ID NOs: 2, 5, 8, 11, 14, 17, or 20 can be 98%, 99%, 99.9% or even higher.

According to other embodiments of the invention, isolated polypeptides comprising a fragment of the above-described polypeptide sequences are provided. These fragments preferably include at least 20 contiguous amino acids, more preferably at least 25, 30, 35, 40, 45, 50, 60, 70, 80, 90, 100 or even more contiguous amino acids.

The polypeptides of the present invention also include fusions between the above-described polypeptide sequences and heterologous polypeptides. The heterologous sequences can, for example, include heterologous sequences designed to facilitate purification and/or visualization of recombinantly-expressed proteins. Other non-limiting examples of protein fusions include those that permit display of the encoded protein on the surface of a phage or a cell, fusions to intrinsically fluorescent proteins, such as green fluorescent protein (GFP), and fusions to the IgG Fc region.

Host Cells

In another aspect of the invention, host cells transformed with the nucleic acid molecules or vectors of the invention, and descendants thereof, are provided. In some embodiments of the invention, these cells carry the nucleic acid sequences of the invention on vectors, which may but need not be freely replicating vectors. In other embodiments of the invention, the nucleic acids have been integrated into the genome of the host cells. In a preferred embodiment, the host cells of the invention have been mutated by recombination with a disruption, deletion or mutation of the isolated nucleic acid of the invention so that the argininosuccinate synthase (ARG1), amino-acid N-acetyltransferase (ARG2), ornithine carbamoyltransferase (ARG3) ATP phosphoribosyltransferase (HIS1), histidinol-phosphatase (HIS2) histidinol-phosphatase transaminase (HIS5) or 1-[(5-phosphoribosyl-5-(5-phosphoribosylamino]imidazole 4-carboxamide isomerase (HIS6) activity in the host cell is reduced compared to a host cell lacking the mutation. The host cell of the invention is preferably *Pichia pastoris* or *Pichia methanolica*, but other host cells, especially yeast cells, are also encompassed within the scope of the invention.

In other embodiments of the invention, host cells defective in argininosuccinate synthase (ARG1), amino-acid N-acetyltransferase (ARG2), ornithine carbamoyltransferase (ARG3), ATP phosphoribosyltransferase (HIS1), histidinol-phosphatase (HIS2), histidinol-phosphatase transaminase (HIS5), or 1-[(5-phosphoribosyl-5-(5-phospho-ribosylamino]imidazole 4-carboxamide isomerase (HIS6) activity are used to integrate one or more sequences or genes of interest into the host cell genome using nucleic acid molecules and/or methods of the invention. In some embodiments, the sequences or genes of interest are integrated so as to disrupt an endogenous gene of the host cell. Cells containing the integration are identified by the recovery of arginine or histidine prototrophy due to the concomitant integration of a gene encoding *P. pastoris* argininosuccinate synthase (ARG1), amino-acid N-acetyltransferase (ARG2), ornithine carbamoyltransferase (ARG3), ATP phosphoribosyltransferase (HIS1), histidinol-phosphatase (HIS2), histidinol-phosphatase transaminase (HIS5), or 1-[(5-phosphoribosyl-5-(5-phosphoribosylamino]imidazole 4-carboxamide isomerase (HIS6) activity. In a further embodiment of the invention, arginine or histidine auxotrophs of the modified host cells are provided by selection of cells in which the *P. pastoris* argininosuccinate synthase (ARG1) (SEQ ID NO: 1), amino-acid N-acetyltransferase (ARG2) (SEQ ID NO: 4), ornithine carbamoyltransferase (ARG3) (SEQ ID NO: 7), ATP phosphoribosyltransferase (HIS1) (SEQ ID NO: 10), histidinol-phosphatase (HIS2), histidinol-phosphatase transaminase (HIS5) (SEQ ID NO: 13), or 1-[(5-phosphoribosyl-5-(5-phosphoribosylamino]imidazole 4-carboxamide isomerase (HIS6) (SEQ ID NO: 19) gene has been excised by homologous recombination.

Methods for the Genetic Integration of Nucleic Acid Sequences: Disruption of a Host Gene Encoding ARG1 (Argininosuccinate Synthase); ARG2 (amino-acid N-acetyltransferase); ARG3 (Ornithine Carbamoyltransferase), HIS1 (ATP Phosphoribosyltransferase), HIS2 (Histidinol-Phosphatase), HIS5 (Histidinol-Phosphatase Transaminase), or HIS6 1-[(5-phosphoribosyl-5-(5-phosphoribosylamino]imidazole 4-carboxamide isomerase, According to one embodiment of the present invention, a method for the genetic integration of several separate heterologous nucleic acid sequences into the genome of a host cell is provided. In one aspect of this embodiment, seven genes of the host cell are disrupted by homologous recombination using integrating vectors. The integrating vectors carry an auxotrophic marker flanked by targeting sequences for the gene to be disrupted along with the desired heterologous gene to be stably integrated. The order in which these plasmids are integrated is fundamental for the auxotrophic selection of the marker genes. In order for the host cell to metabolically require a specific marker gene provided by the plasmid, the specific gene has to have been disrupted by a preceding plasmid.

According to another embodiment of the present invention, a method for the genetic integration of a heterologous nucleic acid sequence into the genome of a host cell is provided. In one aspect of this embodiment, a host gene encoding argininosuccinate synthase (ARG1) (SEQ ID NO: 1), amino-acid N-acetyltransferase (ARG2) (SEQ ID NO: 4), ornithine carbamoyltransferase (ARG3) (SEQ ID NO: 7), ATP phosphoribosyltransferase (HIS1) (SEQ ID NO: 10) histidinol-phosphatase (HIS2) (SEQ ID NO: 13), histidinol-phosphatase transaminase (HIS5) (SEQ ID NO: 16), or 1-[(5-phosphoribosyl-5-(5-phosphoribosylamino]imidazole 4-carboxamide isomerase (HIS6) (SEQ ID NO: 19) is disrupted by the introduction of a disrupted, deleted or otherwise mutated nucleic acid sequence derived from the *P. pastoris* ARG1, ARG2, ARG3, HIS1, HIS2, HIS5 or HIS6 gene disclosed herein (SEQ ID NOS: 1, 4, 7, 10, 13, 16 or 19). Accordingly, disrupted host cells having a point mutation, rearrangement, insertion or preferably a deletion (including a "marked deletion", in which a heterologous selectable sequence has replaced the deleted ARG1, ARG2, ARG3, HIS1, HIS2, HIS5 or HIS6 sequence) are provided. Host cells disrupted in the URA5 gene and consequently lacking in orotate-phosphoribosyl transferase activity serve as suitable hosts for further embodiments of the invention in which heterologous sequences may be introduced into the host cell genome by targeted integration.

In a preferred embodiment, the cloned genes are initially disrupted individually using a series of knockout vectors, which delete large parts of the open reading frames and replace them with a PpGAPDH promoter/ScCYC1 terminator expression cassette and utilize the previously described PpURA5-blaster (Nett and Gerngross, *Yeast* 20: 1279-1290 (2003)) as an auxotrophic marker cassette. By knocking out each gene individually, the utility of these knockouts could be assessed prior to attempting the serial integration of all seven knockout vectors. All gene disruptions occurred at high frequencies (68%-90%), and had the expected non-leaky auxotrophic phenotypes except the Δhis2 which grew slowly on histidine.

In a preferred embodiment, the individual disruption of the genes encoding ARG1, ARG2, ARG3, HIS1, HIS2, HIS5 and HIS6 (SEQ ID NO: 1, 4, 7, 10, 14, 16 and 19) of the host cell with specific integrating plasmids is provided. In one aspect of this embodiment, either a ura5 auxotrophic strain or any prototrophic strain is transformed with a plasmid that disrupts a HIS gene using the URA5-blaster selection marker in the ura5 strain or the hygromicin resistance gene as a selection marker in any prototrophic strain. A second HIS gene is then used as an auxotrophic marker in the second transformation for the disruption of an ARG gene. In the third transformation, another ARG gene is used as an auxotrophic marker for the disruption of a different HIS gene. For the fourth, fifth, sixth and seventh transformations, disruption is alternated between the HIS and ARG genes until all available HIS and ARG genes are exhausted. A diagram of this alternating pathway is shown in FIG. 9. In another embodiment, the initial gene to be disrupted can be any of the ARG or HIS genes, as long as the marker gene encodes for a protein of a different amino acid synthesis pathway than that of the disrupted gene. Furthermore, this alternating method needs only to be carried for as many markers and gene disruptions required for any given desired strain. For each transformation, one or multiple heterologous genes can be integrated into the genome and expressed using the constitutively active GAPDH promoter (Waterham et al. *Gene* 186: 37-44 (1997)) or any expression cassette that can be cloned into the plasmids using the unique restriction sites.

In a preferred embodiment, the vector is a non-autonomously replicating, integrative vector which is designed to function as a gene disruption or replacement cassette. An integrative vector of the invention comprises one or more regions containing "target gene sequences" (sequences which can undergo homologous recombination with sequences at a desired genomic site in the host cell) linked to one of the seven genes (ARG1, ARG2, ARG3, HIS1, HIS2, HIS5 or HIS6) (SEQ ID NOS: 1, 4, 7, 10, 13, 16 or 19) cloned in *P. pastoris*.

In a preferred method of the invention, a host gene that encodes an undesirable activity, (e.g., an enzymatic activity) may be mutated (e.g., interrupted) by targeting a *P. pastoris*—argininosuccinate synthase (ARG1), amino-acid N-acetyltransferase (ARG2), ornithine carbamoyltransferase (ARG3), ATP phosphoribosyltransferase (HIS1), histidinol-phosphatase (HIS2), histidinol-phosphatase transaminase (HIS5), 1-[(5-phosphoribosyl-5-(5-phosphoribosylamino] imidazole 4-carboxamide isomerase (HIS6)-encoding replacement or disruption cassette of the invention into the host gene by homologous recombination. In a preferred embodiment, an undesired glycosylation enzyme activity (e.g., an initiating mannosyltransferase activity such as OCH1) is disrupted in the host cell to alter the glycosylation of polypeptides produced in the cell.

Methods for the Genetic Integration of Nucleic Acid Sequences: Introduction of a Sequence of Interest in Linkage with a Marker Sequence The isolated nucleic acid molecules of the present invention may additionally include a sequence or gene of interest. A sequence or gene of interest typically encodes a protein that is not normally produced in the host cell. The sequence or gene of interest may be preferably linked to one or more expression control sequences, so that the protein encoded by the sequence can be expressed under appropriate conditions in host cells that contain the isolated nucleic acid molecule.

In another aspect of the present invention, a heterologous nucleic acid sequence is introduced into a yeast host cell lacking argininosuccinate synthase (ARG1), amino-acid N-acetyltransferase (ARG2), ornithine carbamoyltransferase (ARG3), ATP phosphoribosyltransferase (HIS1), histidinol-phosphatase (HIS2), histidinol-phosphatase transaminase (HIS5), or 1-[(5-phosphoribosyl-5-(5-phosphoribosylamino] imidazole 4-carboxamide isomerase (HIS6). The heterologous nucleic acid sequences introduced using this method are linked to a nucleic acid sequence that encodes the P. pastoris argininosuccinate synthase (ARG1) (SEQ ID NO: 1), amino-acid N-acetyltransferase (ARG2) (SEQ ID NO: 4), ornithine carbamoyltransferase (ARG3) (SEQ ID NO: 7), ATP phosphoribosyltransferase (HIS1) (SEQ ID NO: 10), histidinol-phosphatase (HIS2) (SEQ ID NO: 13), histidinol-phosphatase transaminase (HIS5) (SEQ ID NO: 16) or 1-[(5-phosphoribosyl-5-(5-phosphoribosylamino]imidazole 4-carboxamide isomerase (HIS6) (SEQ ID NO: 19) activity, preferably on a vector. Upon transformation of the vector into competent arg1, arg2, arg3, his1, his2, his5 and/or his6 host cells, cells containing heterologous sequences linked to the argininosuccinate synthase (ARG1), amino-acid N-acetyltransferase (ARG2), ornithine carbamoyltransferase (ARG3), ATP phosphoribosyltransferase (HIS1), histidinol-phosphatase (HIS2), histidinol-phosphatase transaminase (HIS5), or 1-[(5-phosphoribosyl-5-(5-phosphoribosylamino] imidazole 4-carboxamide isomerase (HIS6) encoding sequences (SEQ ID NOS: 1, 4, 7, 10, 13, 16 or 19, respectively) of the invention may be selected based on their ability to grow in the absence of supplemental arginine or histidine.

In one embodiment, the method comprises the step of introducing into a competent arg1, arg2, arg3, his1, his2, his5 and/or his6 host cell an autonomously replicating vector which is passed from mother to daughter cells during cell replication. The autonomously replicating vector comprises heterologous nucleic acid sequences of interest linked to P. pastoris argininosuccinate synthase (ARG1), amino-acid N-acetyltransferase (ARG2), ornithine carbamoyltransferase (ARG3), ATP phosphoribosyltransferase (HIS1), histidinol-phosphatase (HIS2), histidinol-phosphatase transaminase (HIS5), or 1-[(5-phosphoribosyl-5-(5-phosphoribosylamino] imidazole 4-carboxamide isomerase (HIS6)-encoding sequences (SEQ ID NOS: 1, 4, 7, 10, 13, 16, or 19 respectively) and optionally comprises an element which ensures that it is stably maintained at a single copy in each cell (e.g., a centromere-like sequence such as "CEN"). In another embodiment, the autonomously replicating vector may optionally comprise an element which enables the vector to be replicated to higher than one copy per host cell (e.g., an autonomously replicating sequence or "ARS").

In a preferred embodiment, the vector is a non-autonomously replicating, integrative vector which is designed to function as a gene disruption or replacement cassette. An integrative vector of the invention comprises one or more regions comprising "target gene sequences" (sequences which can undergo homologous recombination with sequences at a desired genomic site in the host cell) linked to P. pastoris argininosuccinate synthase (ARG1), amino-acid N-acetyltransferase (ARG2), ornithine carbamoyltransferase (ARG3), ATP phosphoribosyltransferase (HIS1), histidinol-phosphatase (HIS2), histidinol-phosphatase transaminase (HIS5), or 1-[(5-phosphoribosyl-5-(5-phosphoribosylamino] imidazole 4-carboxamide isomerase (HIS6)-encoding sequences (SEQ ID NOS: 1, 4, 7, 10, 13, 16 or 19, respectively) of the invention. The argininosuccinate synthase (ARG1), amino-acid N-acetyltransferase (ARG2), ornithine carbamoyltransferase (ARG3), ATP phosphoribosyltransferase (HIS1), histidinol-phosphatase (HIS2), histidinol-phosphatase transaminase (HIS5), or 1-[(5-phosphoribosyl-5-(5-phosphoribosylamino]imidazole 4-carboxamide isomerase (HIS6)-encoding sequences (SEQ ID NOS: 1, 4, 7, 10, 13, 16 or 19, respectively) may be adjacent to the target gene sequences (e.g., a gene replacement cassette) or may be engineered to disrupt the target gene sequences (e.g., a gene disruption cassette). The presence of target gene sequences in the replacement or disruption cassettes targets integration of the cassette to specific genomic regions in the host by homologous recombination.

In a preferred method of the invention, a host gene that encodes an undesirable activity, (e.g., an enzymatic activity) may be mutated (e.g., interrupted) by targeting a P. pastoris argininosuccinate synthase (ARG1), amino-acid N-acetyltransferase (ARG2), ornithine carbamoyltransferase (ARG3), ATP phosphoribosyltransferase (HIS1), histidinol-phosphatase (HIS2), histidinol-phosphatase transaminase (HIS5), or 1-[(5-phosphoribosyl-5-(5-phosphoribosylamino] imidazole 4-carboxamide isomerase (HIS6) (SEQ ID NOS: 1, 4, 7, 10, 13, 16 or 19, respectively)-encoding replacement or disruption cassette of the invention into the host gene by homologous recombination. In a preferred embodiment, a gene encoding for an undesired glycosylation enzyme activity (e.g., an initiating mannosyltransferase activity such as Och1p) is disrupted in the host cell to alter the glycosylation of polypeptides produced in the cell.

In yet a further embodiment of the invention, a gene encoding a heterologous protein is engineered with linkage to P. pastoris ARG1, ARG2, ARG3, HIS1, HIS2, HIS5 or HIS6 genes (SEQ ID NOS: 1, 4, 7, 10, 13, 16 or 19, respectively) within the gene replacement or disruption cassette. In a preferred embodiment, the cassette is integrated into a locus of the host genome which encodes an undesirable activity, such as an enzymatic activity. For example, in one preferred embodiment, the cassette is integrated into a host gene which encodes an initiating mannosyltransferase activity such as the OCH1 gene.

In an alternative embodiment, the method comprises the step of introducing into a competent arg, his, ura (uracil), ade (adenine), met (methionine), lys (lysine) and/or pro (proline) mutant host cell an autonomously replicating vector which is passed from mother to daughter cells during cell replication. The autonomously replicating vector comprises P. pastoris genes participating in the biosynthetic pathway of amino acids including, but not limited to: methionine (MET), adenine (ADE), uracil (URA), lysine (LYS), arginine (ARG), histidine (HIS) and proline (PRO).

Accordingly, the present invention provides a method for inactivating alternately at least two biosynthetic pathways in a methylotrophic yeast comprising:

(a) inactivating a first yeast gene in a pathway involved in synthesizing an amino acid or a nucleotide selected from the group consisting of adenine, arginine, histidine, lysine, methionine, proline and uracil with a first selectable marker thereby rendering the host auxotrophic for the amino acid or nucleotide; and (b) inactivating a second yeast gene not from the same pathway that was inactivated in (a) involved in synthesizing an amino acid or a nucleotide selected from the group consisting of adenine, arginine, histidine, lysine, methionine, proline and uracil using the yeast gene that was inactivated in (a) as a second selectable marker. Preferably, 2 biosynthetic pathways selected alternately inactivate arginine biosynthesis and histidine biosynthesis.

The engineered cassette is also useful for "knocking-in" genes encoding such glycosylation enzymes and other sequences of interest in strains of yeast cells to produce glycoproteins with human-like glycosylations and other useful proteins of interest. In a more preferred embodiment, the cassette further comprises one or more genes encoding desirable glycosylation enzymes, including but not limited to mannosidases, N-acetylglucosaminyltransferases (GnTs), UDP-N-acetylglucosamine transporters, galactosyltransferases (GalTs), sialytransferases (STs) and protein-mannosyltransferases (PMTs).

In another embodiment, the cassette comprises one or more genes encoding useful therapeutic proteins, e.g. including but not limited to the kringle domain of human plasminogen, erythropoietin, cytokines such as interferon-α, interferon-β, interferon-γ, interferon-ω, TNF-α, granulocyte-CSF, GM-CSF, interleukins such as IL-1ra, coagulation factors such as factor VIII, factor IX, human protein C, antithrombin III and thrombopoeitin antibodies; IgG, IgA, IgD, IgE, IgM and fragments thereof, Fc and Fab regions, soluble IgE receptor α-chain, urokinase, chymase, and urea trypsin inhibitor, IGF-binding protein, epidermal growth factor, growth hormone-releasing factor, FSH, annexin V fusion protein, angiostatin, vascular endothelial growth factor-2, myeloid progenitor inhibitory factor-1, osteoprotegerin, α-1 antitrypsin, DNase II, α-feto proteins and glucocerebrosidase.

The following examples are for illustrative purposes and are not intended to limit the scope of the invention.

EXAMPLE 1

General Materials and Methods

Escherichia coli strain DH5α (Invitrogen, Carlsbad, Calif.) was used for recombinant DNA work. P. pastoris strain YJN165 (ura5) (Nett and Gerngross, Yeast 20: 1279-1290 (2003)) was used for construction of yeast strains. PCR reactions were performed according to supplier recommendations using ExTaq (TaKaRa, Madison, Wis.), Taq Poly (Promega, Madison, Wis.) or Pfu Turbo® (Stratagene, Cedar Creek, Tex.). Restriction and modification enzymes were from New England Biolabs (Beverly, Mass.).

Yeast strains were grown in YPD (1% yeast extract, 2% peptone, 2% dextrose and 1.5% agar) or synthetic defined medium (1.4% yeast nitrogen base, 2% dextrose, $4 \times 10^{-5}$% biotin and 1.5% agar) supplemented as appropriate. Plasmid transformations were performed using chemically competent cells according to the method of Hanahan (Hanahan et al., Methods Enzymol. 204: 63-113 (1991)). Yeast transformations were performed by electroporation according to a modified procedure described in the Pichia Expression Kit Manual (Invitrogen). In short, yeast cultures in logarithmic growth phase were washed twice in distilled water and once in 1M sorbitol. Between 5 and 50 μg of linearized DNA in 10 μl of TE was mixed with 100 μl yeast cells and electroporated using a BTX electroporation system (BTX, San Diego, Calif.). After addition of 1 ml recovery medium (1% yeast extract, 2% peptone, 2% dextrose, $4 \times 10^{-5}$% biotin, 1M sorbitol, 0.4 mg/ml ampicillin, 0.136 mg/ml chloramphenicol), the cells were incubated without agitation for 4 h at room temperature and then spread onto appropriate media plates.

PCR analysis of the modified yeast strains was as follows. A 10 ml overnight yeast culture was washed once with water and resuspended 400 μl breaking buffer (100 mM NaCl, 10 mM Tris, pH 8.0, 1 mM EDTA, 1% SDS, 2% Triton X-100). After addition of 400 mg of acid washed glass beads and 400 μl phenol-chloroform, the mixture was vortexed for 3 minutes. Following addition of 200 μl TE (Tris/EDTA) and centrifugation in a microcentrifuge for 5 minutes at maximum speed, 500 μl of the supernatant was transferred to a fresh tube and the DNA was precipitated by addition of 1 ml ice-cold ethanol. The precipitated DNA was isolated by centrifugation, resuspended in 400 μl TE, with 1 mg RNase A, and the mixture was incubated for 10 minutes at 37° C. Then 1 μl of 4M NaCl, 20 μl of a 20% SDS solution and 10 μl of Qiagen Proteinase K solution was added and the mixture was incubated at 37° C. for 30 minutes. Following another phenol-chloroform extraction, the purified DNA was precipitated using sodium acetate and ethanol and washed twice with 70% ethanol. After air drying, the DNA was resuspended in 200 μl TE, and 200 ug was used per 50 μl PCR reaction.

EXAMPLE 2

Cloning of P. pastoris ARG1, ARG2, ARG3, HIS1, HIS2, HIS5, and HIS6 Genes

The P. pastoris orthologues to the S. cerevisiae ARG1, ARG2, ARG3, HIS1, HIS2, HIS5 and HIS6 genes were cloned by comparison of the translations of the respective S. cerevisiae open reading frames to a partial P. pastoris genomic sequence provided by Integrated Genomics Inc. using the BLAST program (Altschul et al., J. Mol. Biol. 215: 403-410 (1990)). Using the S. cerevisiae ARG1 ORF (SEQ ID NO: 3) as bait we identified a P. pastoris ORF of 416 amino acids (SEQ ID NO: 2) with 72.9% identity (FIG. 1). The ARG2 orthologue encoded an ORF of 590 amino acids (SEQ ID NO: 5) with 29.8% identity to ScARG2 (SEQ ID NO: 6) (FIG. 2). The ARG3 orthologue encoded an ORF of 342 amino acids (SEQ ID NO: 8) with 57.3% identity to ScARG3 (SEQ ID NO: 9)(FIG. 3). Using the ORF encoded by ScHIS1 (SEQ ID NO: 12) as bait we identified a P. pastoris gene sequence consisting of two exons of 51 and 843 nucleotides separated by an intron of 81 nucleotides (SEQ ID NO: 10). The two exons encoded an ORF of 297 amino acids (SEQ ID NO: 11) with 68.4% identity to ScHIS1 (SEQ ID NO: 12) (FIG. 4). The HIS2 orthologue encoded an ORF of 308 amino acids (SEQ ID NO: 14) with 34.3% identity to ScHIS2 (SEQ ID NO: 15) (FIG. 5). The HIS5 orthologue encoded an ORF of 390 amino acids (SEQ ID NO: 17) with 50.4% identity to ScHIS5 (SEQ ID NO: 18) FIG. 6). Using the ORF encoded by ScHIS6 (SEQ ID NO: 21) as bait we identified an ORF of 263 amino acids (SEQ ID NO: 20) with 60.5% identity (FIG. 7).

EXAMPLE 3

Construction of Disruption Vectors and Strains

All disruption vectors were derived from plasmid pJN653 (FIG. 8), which was constructed using a method previously described for pJN267 (Nett and Gerngross, Yeast 20: 1279-1290 (2003)). For amplification of the PpGAPDH promoter and the PpCYC1 transcriptional terminator, the oligos GAP5 clean (SEQ ID NO:22), GAP3 clean (SEQ ID NO:23), CYC5 clean (SEQ ID NO:24) and CYC3 clean (SEQ ID NO:25) were used to amplify genomic DNA from *P. pastoris* strain NRRL Y-11430 for the GAPDH promoter and *S. cerevisiae* strain W303 for the CYC1 terminator. The plasmid consists of two fragments of the 5' and 3' regions of the PpKEX1 gene, flanking the GAPDH/CYC1 expression cassette and a ScURA3-auxotrophic marker cassette which was isolated as a BamHI/BglII fragment from pNKY51 (ATCC). The restriction sites flanking all segments allow for the convenient replacement to generate disruption vectors for the gene of choice. To generate disruption vectors for the cloned ARG and HIS genes, first regions 5' of the start codons of ARG1, ARG2, ARG3, HIS1, HIS2, HIS5 and HIS6 were amplified with flanking restriction sites using oligonucleotides ARG155, ARG153, ARG255, ARG253, ARG355dis, ARG353dis, HIS 155, HIS 153, HIS255, HIS253, HIS555, HIS553, HIS655, HIS653 (SEQ ID NOS:26-39, respectively) and NRRL Y-11430 genomic DNA as template, and the isolated DNA fragments were cloned into vector pCR2.1 (Invitrogen). This resulted in plasmids pJN589, pJN591, pJN593, pJN595, pJN597, pJN599 and pJN601, respectively. The 5' regions were then excised using EcoRI and PmeI for pJN589, pJN591, pJN597 and pJN601, and using SacI and PmeI for pJN593, pJN595 and pJN599, and cloned into pJN653 that had been cut with the same restriction enzymes. This resulted in plasmids pJN654 (ARG1-5'), pJN655 (ARG2-5'), pJN656 (ARG3-5'), pJN657 (HIS1-5'), pJN658 (HIS2-5'), pJN659 (HIS5-5') and pJN660 (HIS6-5'). Subsequently, the regions 3' of the stop codons were amplified with flanking restriction sites using oligonucleotides ARG135, ARG133, ARG235, ARG233, ARG335, ARG333, HIS135, HIS133, HIS235, HIS233, HIS535, HIS533, HIS635, HIS633 (SEQ ID NOS: 40-53, respectively) and NRRL Y-11430 genomic DNA as template, and the isolated DNA fragments were cloned into vector pCR2.1 (Invitrogen). This resulted in plasmids pJN590, pJN592, pJN594, pJN596, pJN598, pJN600 and pJN602, respectively. Subsequently, the 3' regions were excised using SwaI and SphI for pJN590 and SwaI and SalI for pJN592, pJN594, pJN596, pJN598, pJN600 and pJN602 and cloned into the respective 5'-region containing plasmids that had been cut with the same enzymes. This yielded the ScURA3-blaster knockout plasmids pJN665 (ARG1), pJN666 (ARG2), pJN667 (ARG3), pJN668 (HIS1), pJN669 (HIS2), pJN670 (HIS5) and pJN671 (HIS6).

It is known that the heterologous ScURA3 marker does not fully complement the ura3 strains of *P. pastoris* (Lin Cereghino et al., *Gene* 263:159-169 (2001); Nett and Gerngross, *Yeast* 20: 1279-1290 (2003)), therefore we replaced the auxotrophic marker cassette with the PpURA5-blaster cassette (Nett and Gerngross, *Yeast* 20: 1279-1290 (2003)) in the following way—the plasmid, pJN665 was cut with SwaI and BglII, and plasmids pJN666, pJN667, pJN668, pJN669, pJN670 and pJN671 were cut with SwaI and XhoI to release the ScURA3 marker cassette. The isolated plasmid backbones were then made blunt using T4 DNA polymerase and ligated with a blunt EcoRI-SphI DNA fragment containing the PpURA5-blaster cassette from pJN396 (Nett and Gerngross, Yeast 20: 1279-1290 (2003)). This resulted in the PpURA5-blaster knockout plasmids pJN675 (ARG1), pJN676 (ARG2), pJN677 (ARG3), pJN678 (HIS1), pJN679 (HIS2), pJN680 (HIS5) and pJN681 (HIS6).

In order to generate arg1, arg2, arg3, his1, his2, his5 or his6 knockouts, the PpURA5-blaster marked knockout plasmids were linearized using SfiI and individually transformed into the ura5 *P. pastoris* strain YJN165 (Nett and Gerngross, Yeast 20: 1279-1290 (2003)). Positive clones were selected on defined minimal medium lacking uracil, and for each transformation 50 individual colonies were restreaked for continued growth. After overnight growth, the potential arg1, arg2 and arg3 knockout clones were replicated onto defined minimal medium lacking arginine, and the potential his1, his2, his5, and his6 knockout clones were replicated onto defined minimal medium lacking histidine. In all cases more than 44% of the clones showed the expected auxotrophy. Only the yeast strain that had the Δhis2 deletion was able to grow slowly on medium lacking histidine, whereas all others displayed non-leaky phenotypes. Proper integration of the knockout vectors was then confirmed by PCR using oligonucleotides internal to the knockout vectors (GCGAP-Seq1, SEQ ID NO:66 and GCCYC-Seq1, SEQ ID NO:67) and upstream or downstream of the 5'- and 3'-regions (Oligos-Pre5' and Post-3', SEQ ID NOS:68-81). The auxotrophic strains were designated YJN408 (arg1), YJN409 (arg2), YJN410 (arg3), YJN411 (his1), YJN412 (his2), YJN413 (his5) and YJN414 (his6).

EXAMPLE 4

Use of ARG1, ARG2, ARG3, HIS1, HIS2, and HIS5 as Auxotrophic Markers

To use the cloned genes as auxotrophic markers and to enable their consecutive use in multiple genetic engineering steps, we devised the strategy outlined in FIG. 9. In this approach either a ura5 auxotrophic strain or any prototrophic strain of *P. pastoris* is transformed with a plasmid that disrupts HIS1 using either the URA5-blaster or the Hygromycin resistance gene as markers. The HIS1 gene is then used as an auxotrophic marker in the second round to disrupt ARG1. In the third step the ARG1 gene is used to disrupt HIS2, and so on (see FIG. 9). During each round of transformation one or multiple heterologous genes can be integrated into the genome and expressed using the constitutively strong GAPDH promoter (Waterham et al., *Gene* 186: 37-44 (1997)) or any other expression cassette that can be added into the plasmids using the unique restriction sites.

For construction of the knock-in vectors, the open reading frames of ARG1, ARG2, ARG3, HIS1, HIS2 and HIS5 and their respective 5'- and 3'-untranslated regions were PCR amplified using oligonucleotides ARG15, ARG13, ARG25, ARG23, ARG35, ARG33, HIS15, HIS13, HIS25, HIS23, HIS55 and HIS53 (SEQ ID NOS:54-65, respectively), and cloned into plasmid pCR2.1 (Invitrogen) to create plasmids pJN603 (ARG1), pJN604 (ARG2), pJN605 (ARG3), pJN606 (HIS1), pJN607 (HIS2) and pJN608 (HIS5). The ARG or HIS ORFs were then excised using the introduced restriction sites and cloned into the following markerless plasmid backbones. The HIS1 marker cassette was released with SwaI and BglII and cloned into the arg1 knockout plasmid pJN665 that had been cut with the same enzymes to yield pJN702. The ARG1 marker cassette was released with PmeI and cloned into the his2 knockout plasmid pJN669 that had been cut with SwaI and XhoI and blunt ended, resulting in pJN703. The HIS2 marker cassette was released using SwaI and XhoI and cloned into the arg2 knockout plasmid pJN666 that had been cut with the same enzymes creating pJN704. Following a similar procedure—the ARG2 marker cassette was cloned into the his5 knockout plasmid pJN670 to yield pJN705; the HIS5 marker cassette was cloned into the arg3 knockout plasmid pJN667 to create pJN706, and the ARG3 knockout cassette was cloned into the his6 knockout plasmid pJN671 to yield pJN707. To generate a plasmid that disrupts his1 using the Hygromycin resistance gene, we isolated the Hygromycin resistance cassette from plasmid pAG32 (Goldstein and McCusker, *Yeast* 15: 1541-1553 (1999)) as a SacI, BglII fragment. After T4 DNA polymerase treatment a blunt Hygromycin resistance gene fragment was ligated into the blunt-ended his1 knockout plasmid pJN668 cut with SwaI and XhoI. This resulted in plasmid pJN701b. The common structural elements of the knock-in vectors are depicted in FIG. 8B.

To confirm the functionality of the marker cassettes and to individually mimic the steps of the strategy outlined in FIG. 9, the linearized plasmids pJN701, pJN702, pJN703, pJN704, pJN705, pJN706 and pJN707 were transformed into the series of yeast strains YJN408 through YJN413 in the following order: plasmids pJN701b (Δhis1::HYGR) and pJN703 (Δhis2::ARG1) were transformed into YJN408 (Δarg1) and transformants were selected on YPD containing 150 μg/ml Hygromycin or a defined minimal medium lacking arginine, respectively. Plasmid pJN705 (Δhis5::ARG2) was transformed into YJN409 (Δarg2) and pJN707 (Δhis6::ARG3) was transformed into YJN410 (Δarg3), and colonies were selected on defined medium lacking arginine. Finally plasmid pJN702 (arg1::HIS1) was transformed into YJN411 (Δhis1), pJN704 (arg2::HIS2) was transformed into YJN412 (his2) and pJN706 (arg3::HIS5) was transformed into YJN413 (Δhis5), and colonies were selected on defined medium lacking histidine. From each transformation 50 colonies were replicated onto defined medium lacking the appropriate amino acid to determine which clones had integrated the plasmids at the correct locus resulting in gene disruptions. The disruption frequency obtained using the cloned ARG or HIS genes as markers is comparable to what was seen with the URA5-blaster, with 68% to 94% of the transformants showing gene disruption.

We claim:

1. A method for alternately inactivating two or more biosynthetic pathways in a *P. pastoris* host, comprising the steps of:
   (a) inactivating a first gene from a first biosynthetic pathway in the *P. pastoris* host, wherein said first gene is involved in the synthesis of a first amino acid or a nucleotide selected from the group consisting of adenine, arginine, histidine, methionine and uracil, by deleting or disrupting the first gene with a first nucleic acid encoding a first selectable marker, thereby rendering the *P. pastoris* host auxotrophic for the first amino acid or nucleotide whose synthesis the first gene is involved in; and
   (b) inactivating a second gene from a second biosynthetic pathway in the *P. pastoris* host from step (a), wherein said second gene is involved in the synthesis of a second amino acid or a nucleotide selected from the group consisting of adenine, arginine, histidine, methionine, and uracil, by deleting or disrupting the second gene with a second nucleic acid, wherein said second nucleic acid is the gene that was inactivated in step (a), wherein the second gene is not involved in the synthesis of the first nucleotide or amino acid whose synthesis the first gene of step (a) is involved in, thereby rendering the *P. pastoris* host auxotrophic for the second amino acid or nucleotide whose synthesis the second gene is involved in, and no longer auxotrophic for the first amino acid or nucleotide of step (a).

2. The method of claim 1, wherein the at least two biosynthetic pathways are the arginine biosynthesis and histidine biosynthesis pathways.

3. The method of claim 1, wherein the first marker is a dominant selectable marker, an auxotrophic marker, or a nutritional marker.

4. The method of claim 1, wherein the inactivation step includes integrating and expressing one or more heterologous genes into the *Pichia pastoris* host genome.

5. The method of claim 1, wherein said method further comprises the inactivation of an additional gene in the *P. pastoris* host from step (b), wherein said additional gene is involved in the synthesis of the first amino acid or nucleotide of step (a), or another amino acid or nucleotide selected from the group consisting of adenine, arginine, histidine, methionine, and uracil, by deleting or disrupting the additional gene with a nucleic acid, wherein said nucleic acid is the gene that was inactivated in step (b), wherein the additional gene is not involved in the synthesis of the second nucleotide or amino acid of step (b), thereby rendering the *P. pastoris* host (1) auxotrophic for the first amino acid or nucleotide of step (a), or auxotrophic for the amino acid or nucleotide whose synthesis the additional gene is involved in, and (2) no longer auxotrophic for the second amino acid or nucleotide of step (b).

* * * * *